(12) United States Patent
Klinman et al.

(10) Patent No.: US 7,666,674 B2
(45) Date of Patent: Feb. 23, 2010

(54) USE OF STERICALLY STABILIZED CATIONIC LIPOSOMES TO EFFICIENTLY DELIVER CPG OLIGONUCLEOTIDES IN VIVO

(75) Inventors: Dennis M. Klinman, Potomac, MD (US); Ihsan Gursel, Rockville, MD (US); Ken J. Ishii, Osaka (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 846 days.

(21) Appl. No.: 10/484,991

(22) PCT Filed: Jul. 29, 2002

(86) PCT No.: PCT/US02/24235

§ 371 (c)(1),
(2), (4) Date: Jun. 4, 2004

(87) PCT Pub. No.: WO03/040308

PCT Pub. Date: May 15, 2003

(65) Prior Publication Data

US 2005/0214355 A1    Sep. 29, 2005

Related U.S. Application Data

(60) Provisional application No. 60/308,283, filed on Jul. 27, 2001.

(51) Int. Cl.
*C12N 5/00* (2006.01)
*C12N 5/02* (2006.01)
*A61K 9/127* (2006.01)
*A61K 31/70* (2006.01)
*A01N 43/04* (2006.01)

(52) U.S. Cl. .................. 435/375; 424/450; 435/325; 514/44

(58) Field of Classification Search .............. None
See application file for complete search history.

(56) References Cited

U.S. PATENT DOCUMENTS

| | | | |
|---|---|---|---|
| 2,215,233 A | 9/1940 | Ruskin | |
| 3,906,092 A | 9/1975 | Hilleman et al. | |
| 3,911,117 A | 10/1975 | Ender | |
| 3,914,450 A | 10/1975 | Robbins et al. | |
| 4,469,863 A | 9/1984 | Ts'o et al. | |
| 4,544,559 A | 10/1985 | Gil et al. | |
| 4,741,914 A | 5/1988 | Kimizuka et al. | |
| 4,758,553 A | 7/1988 | Ogoshi | |
| 4,806,376 A | 2/1989 | Saeki et al. | |
| 4,956,296 A | 9/1990 | Fahnestock | |
| 4,963,387 A | 10/1990 | Nakagawa et al. | |
| 4,994,442 A | 2/1991 | Gil et al. | |
| 5,023,243 A | 6/1991 | Tullis | |
| 5,066,500 A | 11/1991 | Gil et al. | |
| 5,231,085 A | 7/1993 | Alexander et al. | |
| 5,234,811 A | 8/1993 | Beutler et al. | |
| 5,248,670 A | 9/1993 | Draper et al. | |
| 5,268,365 A | 12/1993 | Rudolph et al. | |
| 5,288,509 A | 2/1994 | Potman et al. | |
| 5,488,039 A | 1/1996 | Masor et al. | |
| 5,492,899 A | 2/1996 | Masor et al. | |
| 5,585,479 A | 12/1996 | Hoke et al. | |
| 5,591,721 A | 1/1997 | Agrawal et al. | |
| 5,602,109 A | 2/1997 | Masor et al. | |
| 5,612,060 A | 3/1997 | Alexander | |
| 5,614,191 A | 3/1997 | Puri et al. | |
| 5,650,156 A | 7/1997 | Grinstaff et al. | |
| 5,663,153 A | 9/1997 | Hutcerson et al. | |
| 5,679,397 A | 10/1997 | Kuroda et al. | |
| 5,684,147 A | 11/1997 | Agrawal et al. | |
| 5,700,590 A | 12/1997 | Masor et al. | |
| 5,712,256 A | 1/1998 | Kulkarni et al. | |
| 5,723,335 A | 3/1998 | Hutcerson et al. | |

(Continued)

FOREIGN PATENT DOCUMENTS

EP    0 286 224    10/1988

(Continued)

OTHER PUBLICATIONS

Bei et al. Journal of Immunotherapy, 1998, vol. 21, No. 3, pp. 159-169.*
Adya, et al., "Expansion of CREB's DNA recognition specificity by Tax results from interaction with Ala-Ala-Arg at positions 282-284 near the conserved DNA-binding domain of CREB". Proc. Natl. Acad. Sci. USA 91(12):5642-5646 (1994).
Agrawal, et al., "Pharmacokinetics of Oligonucleotides". Ciba. Found. Symp. 209:60-78 (1997), abstract.
Agrawal, et al., "Pharmacokinetics and Bioavailability of Antisense Oligonucleotides Following Oral and Colorectal Adminstration of Experimental Animals". Handb. Exp. Pharmacol.: Antisense Research and Application 131:525-543 (1998).

(Continued)

*Primary Examiner*—Janet L. Epps-Smith
(74) *Attorney, Agent, or Firm*—Klarquist Sparkman, LLP

(57) ABSTRACT

Sterically stabilized cationic liposomes (SSCL) encapsulating a K type oligodeoxynucleotide (ODN) including a CpG motif are disclosed. These SSCL encapuslating a K type ODN can be used to effectively deliver the ODN to a cell. A novel method is also disclosed for producing the SSCL encapsulating the K type ODN. Administration of the SSCL encapsulating a K type ODN and a chemotherapeutic agent, such as a chimeric molecule comprising a targeting molecule selected from the group consisting of an IL-13, and an anti-IL-13 receptor antibody; and an effector molecule selected from the group consisting of a *Pseudomonas* exotoxin, a Diphtheria toxin, and a radionuclide, can be used to dramatically reduce the growth of solid tumors.

25 Claims, 22 Drawing Sheets

U.S. PATENT DOCUMENTS

| | | |
|---|---|---|
| 5,786,189 A | 7/1998 | Loct et al. |
| 5,804,566 A | 9/1998 | Carson et al. |
| 5,840,705 A | 11/1998 | Tsukuda |
| 5,849,719 A | 12/1998 | Carson et al. |
| 5,895,652 A | 4/1999 | Giampapa |
| 5,919,456 A | 7/1999 | Puri et al. |
| 5,922,766 A | 7/1999 | Acosta et al. |
| 5,976,580 A | 11/1999 | Ivey et al. |
| 5,980,958 A | 11/1999 | Naylor et al. |
| 5,994,126 A | 11/1999 | Stienman et al. |
| 6,008,202 A * | 12/1999 | Huang et al. .................. 514/44 |
| 6,022,853 A | 2/2000 | Kuberasampath et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 * | 4/2001 | Krieg et al. .................. 514/44 |
| 6,239,116 B1 | 5/2001 | Krieg et al. |
| 6,339,068 B1 | 1/2002 | Krieg et al. |
| 6,406,705 B1 | 6/2002 | Davis et al. |
| 6,423,539 B2 | 7/2002 | Fong et al. |
| 6,428,788 B1 | 8/2002 | Debinski et al. |
| 6,429,199 B1 | 8/2002 | Krieg et al. |
| 6,498,148 B1 | 12/2002 | Raz |
| 6,514,948 B1 | 2/2003 | Raz et al. |
| 6,534,062 B2 | 3/2003 | Krieg et al. |
| 6,552,006 B2 | 4/2003 | Raz et al. |
| 6,562,798 B1 | 5/2003 | Schwartz |
| 6,589,940 B1 | 7/2003 | Raz et al. |
| 6,610,661 B1 | 8/2003 | Carson et al. |
| 6,613,751 B2 | 9/2003 | Raz et al. |
| 6,653,292 B1 | 11/2003 | Krieg et al. |
| 2001/0034330 A1 | 10/2001 | Kensil |
| 2001/0036462 A1 | 11/2001 | Fong et al. |
| 2001/0044416 A1 | 11/2001 | McCluskie et al. |
| 2001/0046967 A1 | 11/2001 | Van Nest |
| 2002/0006403 A1 | 1/2002 | Yu et al. |
| 2002/0028784 A1 | 3/2002 | Van Nest |
| 2002/0042383 A1 | 4/2002 | Yew et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0065236 A1 | 5/2002 | Yew et al. |
| 2002/0086295 A1 | 7/2002 | Raz et al. |
| 2002/0086839 A1 | 7/2002 | Raz et al. |
| 2002/0090724 A1 | 7/2002 | Taylor et al. |
| 2002/0091095 A1 | 7/2002 | Phillips et al. |
| 2002/0091097 A1 | 7/2002 | Bratzler et al. |
| 2002/0098199 A1 | 7/2002 | Van Nest et al. |
| 2002/0098205 A1 | 7/2002 | Choi et al. |
| 2002/0098980 A1 | 7/2002 | Choi et al. |
| 2002/0107212 A1 | 8/2002 | Van Nest et al. |
| 2002/0110569 A1 | 8/2002 | Granoff et al. |
| 2002/0111323 A1 | 8/2002 | Martin et al. |
| 2002/0136776 A1 | 9/2002 | Fang et al. |
| 2002/0137714 A1 | 9/2002 | Kandimalla et al. |
| 2002/0142974 A1 | 10/2002 | Kohn et al. |
| 2002/0142977 A1 | 10/2002 | Raz et al. |
| 2002/0142978 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0183272 A1 | 12/2002 | Johnston et al. |
| 2002/0197269 A1 | 12/2002 | Lingnau et al. |
| 2002/0198165 A1 | 12/2002 | Bratzler et al. |
| 2003/0003579 A1 | 1/2003 | Kadowaki et al. |
| 2003/0022849 A1 | 1/2003 | Chang |
| 2003/0022852 A1 | 1/2003 | Van Nest et al. |
| 2003/0026782 A1 | 2/2003 | Krieg |
| 2003/0026801 A1 | 2/2003 | Weiner et al. |
| 2003/0049266 A1 | 3/2003 | Fearon et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0052839 A1 | 3/2003 | Binley et al. |
| 2003/0055014 A1 | 3/2003 | Bratzler |
| 2003/0059773 A1 | 3/2003 | Van Nest et al. |
| 2003/0060440 A1 | 3/2003 | Klinman et al. |
| 2003/0064064 A1 | 4/2003 | Dina |
| 2003/0072762 A1 | 4/2003 | Van de Winkel et al. |
| 2003/0073142 A1 | 4/2003 | Chen et al. |
| 2003/0078223 A1 | 4/2003 | Raz et al. |
| 2003/0091599 A1 | 5/2003 | Davis et al. |
| 2003/0092663 A1 | 5/2003 | Raz |
| 2003/0096417 A1 | 5/2003 | Fischer |
| 2003/0100527 A1 | 5/2003 | Krieg et al. |
| 2003/0104044 A1 | 6/2003 | Semple et al. |
| 2003/0104523 A1 | 6/2003 | Lipford et al. |
| 2003/0109469 A1 | 6/2003 | Carson et al. |
| 2003/0119773 A1 | 6/2003 | Raz et al. |
| 2003/0119774 A1 | 6/2003 | Foldvari et al. |
| 2003/0119776 A1 | 6/2003 | Phillips et al. |
| 2003/0125284 A1 | 7/2003 | Raz et al. |
| 2003/0129251 A1 | 7/2003 | Van Nest et al. |
| 2003/0130217 A1 | 7/2003 | Raz et al. |
| 2003/0133988 A1 | 7/2003 | Fearon et al. |
| 2003/0135875 A1 | 7/2003 | Ehrhardt et al. |
| 2003/0138413 A1 | 7/2003 | Vicari et al. |
| 2003/0138453 A1 | 7/2003 | O'Hagan et al. |
| 2003/0139364 A1 | 7/2003 | Krieg et al. |
| 2003/0143213 A1 | 7/2003 | Raz et al. |
| 2003/0143743 A1 | 7/2003 | Schuler et al. |
| 2003/0144229 A1 | 7/2003 | Klinman et al. |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0148983 A1 | 8/2003 | Fontoura et al. |
| 2003/0157717 A1 | 8/2003 | Draghia-Akli |
| 2003/0158136 A1 | 8/2003 | Rice et al. |
| 2003/0165478 A1 | 9/2003 | Sokoll |
| 2003/0166001 A1 | 9/2003 | Lipford |
| 2003/0170273 A1 | 9/2003 | O'Hagan et al. |
| 2003/0171321 A1 | 9/2003 | Schmidt et al. |
| 2003/0175731 A1 | 9/2003 | Fearon et al. |
| 2003/0176373 A1 | 9/2003 | Raz et al. |
| 2003/0176389 A1 | 9/2003 | Raz et al. |
| 2003/0180320 A1 | 9/2003 | Darju et al. |
| 2003/0181406 A1 | 9/2003 | Schetter et al. |
| 2003/0185848 A1 | 10/2003 | Johnston et al. |
| 2003/0185900 A1 | 10/2003 | Choi et al. |
| 2003/0186921 A1 | 10/2003 | Carson et al. |
| 2003/0191079 A1 | 10/2003 | Krieg et al. |
| 2003/0199466 A1 | 10/2003 | Fearon et al. |
| 2003/0203861 A1 | 10/2003 | Carson et al. |
| 2003/0206967 A1 | 11/2003 | Choi et al. |
| 2003/0207287 A1 | 11/2003 | Short |
| 2003/0212026 A1 | 11/2003 | Krieg et al. |
| 2003/0212028 A1 | 11/2003 | Raz et al. |
| 2003/0216340 A1 | 11/2003 | Van Nest et al. |
| 2003/0219752 A1 | 11/2003 | Short |
| 2003/0220277 A1 | 11/2003 | Yew et al. |
| 2003/0224010 A1 | 12/2003 | Davis et al. |
| 2003/0225016 A1 | 12/2003 | Fearon et al. |
| 2003/0232780 A1 | 12/2003 | Carson et al. |
| 2004/0005588 A1 | 1/2004 | Cohen et al. |
| 2004/0006010 A1 | 1/2004 | Carson et al. |
| 2004/0006032 A1 | 1/2004 | Lopez |
| 2004/0006034 A1 | 1/2004 | Raz et al. |
| 2004/0009897 A1 | 1/2004 | Sokoll |
| 2004/0009942 A1 | 1/2004 | Van Nest |
| 2004/0009949 A1 | 1/2004 | Krieg |
| 2004/0013686 A1 | 1/2004 | Granoff et al. |
| 2004/0013688 A1 | 1/2004 | Wise et al. |

| | | |
|---|---|---|
| 2004/0028693 A1 | 2/2004 | Wu et al. |

FOREIGN PATENT DOCUMENTS

| | | |
|---|---|---|
| EP | 0 302 758 | 11/1989 |
| EP | 0 468 520 A2 | 1/1991 |
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 91/12811 | 9/1991 |
| WO | WO 92/03456 | 4/1992 |
| WO | WO 92/18522 | 10/1992 |
| WO | WO 92/21353 | 12/1992 |
| WO | WO 93/17115 | 9/1993 |
| WO | WO 94/19945 | 9/1994 |
| WO | WO 95/05853 | 3/1995 |
| WO | WO 95/18231 | 7/1995 |
| WO | WO 95/26204 | 10/1995 |
| WO | WO 96/02555 | 2/1996 |
| WO | WO 96/24380 | 2/1996 |
| WO | WO 96/35782 | 11/1996 |
| WO | WO 97/28259 | 1/1997 |
| WO | WO 98/11211 | 3/1998 |
| WO | WO 98/14210 | 4/1998 |
| WO | WO 98/16247 | 4/1998 |
| WO | WO 98/18810 | 5/1998 |
| WO | WO 98/29430 | 7/1998 |
| WO | WO 98/32462 | 7/1998 |
| WO | WO 98/37919 | 9/1998 |
| WO | WO 98/40100 | 9/1998 |
| WO | WO 98/49288 | 11/1998 |
| WO | WO 98/49348 | 11/1998 |
| WO | WO 98/52581 | 11/1998 |
| WO | WO 98/55495 | 12/1998 |
| WO | WO 99/11275 | 3/1999 |
| WO | WO 99/37151 | 7/1999 |
| WO | WO 99/51259 | 10/1999 |
| WO | WO 9951259 A2 * | 10/1999 |
| WO | WO 99/56755 | 11/1999 |
| WO | WO 99/58118 | 11/1999 |
| WO | WO 99/61056 | 12/1999 |
| WO | WO 99/62923 | 12/1999 |
| WO | WO 00/14217 | 3/2000 |
| WO | WO 00/20039 | 4/2000 |
| WO | WO 00/21556 | 4/2000 |
| WO | WO 00/06588 | 10/2000 |
| WO | WO 00/61151 | 10/2000 |
| WO | WO 00/62787 | 10/2000 |
| WO | WO 00/67023 | 11/2000 |
| WO | WO 00/67787 | 11/2000 |
| WO | WO 01/00232 | 1/2001 |
| WO | WO 01/02007 | 1/2001 |
| WO | WO 01/12223 | 2/2001 |
| WO | WO 01/12804 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |
| WO | WO 02/069369 | 9/2002 |

OTHER PUBLICATIONS

Agrawal, "Antisense Oligonucleotides: Toward Clinical Trials". Tibtech 14:376-387 (1996).
Agrawal, et al., "In Vivo Pharmacokinetics of Phosphorothioate Oligonucleotides Containing Contiguous Guanosines". Antisense & Nucleic Acid Drug Development 7:245-249 (1997).
Agrawal, et al., "Absorption, Tissue Distribution and In Vivo Stability in Rats of a Hybrid Antisense Oligonucleotide Following Oral Administration". Biochemical Pharmacology 50(4):571-576 (1995).
Agrawal, et al., "Pharmacokinetics of Antisense Oligonucleotides". Clin. Pharmacokinet 28(1):7 (1995).
Agrawal, et al., "Antisense therapeutics: is it as simple as complementary base recognition?". Molecular Med. Today 6(2):72-81 (2000), abstract.
Agrawal, et al., "Pharmacokinetics, biodistribution, and stability of oligodeoxynucleotide phosphorothioates in mice". Proc. Natl. Acad. Sci. USA 88:7595-7599 (1991).
Agrawal, "Medicinal Chemistry and Therapeutic Potential of CpG DNA". Trends in Molecular Medicine 8(3):114-121 (2002).
Alama, et al., "Antisense Oligonucleotides as Therapeutic Agents". Pharmacol. Res. 36:171-178 (1997).
Amaral, et al., "Leishmania amazonensis: The asian rhesus macaques (Macaca mulatta) as an experimental model for study of cutaneous leishmaniasis". Exp. Parasitol. 82(1):34-44 (1996).
Anderson, "Human Gene Therapy". Nature 392:25-30 (Apr. 1998).
Anderson, et al., "TH2 and 'TH2-like' cells in allergy and asthma; pharmacological perspectives". TiPS 15:324-332 (1994).
Anfossi, et al., "An oligomer complementary to c-myb-encoded mRNA inhibits proliferation of human myeloid leukemia cell lines". Proc. Natl. Acad. Sci. USA 86:3379-3383 (May 1989).
Angier, "Microbe DNA seen as alien by immune system". New York Times p. C1, 2 pages (1995).
Azad, et al., "Antiviral activity of a phosphorothioate oligonucleotide complementary to RNA of the human cytomegalovirus major immediate-early region". Amtimicrobial Agents and Chemotherapy 37:1945-1954 (1993).
Azuma, "Biochemical and immunological studies on cellular components of tubercle bacilli". Kekkaku 69(9):45-55 (1992).
Azzoni, et al., "Sustained Impairment of IFN-γ Secretion in Suppressed HIV-Infected Patients Despite Mature NK Cell Recovery: Evidence for a Defective Reconstruciton of Innate Immunity". J. Immunol. 168(11):5764-5770 (2002).
Ballas, et al., "Induction of NK activity in murine and human cells by CpG motifs in oligodeoxynucleotides and bacterial DNA". J. Immunol. 157(5):1840-1845 (1996).
Banchereau, et al., "Immunobiology of Dendritic Cells". Ann. Rev. Immunol. 18:767-811 (2000).
Banchereau & Steinman, "Dendritic Cells and the Control of Immunity". Nature 392:245-252 (1998).
Barouch, et al., "Control of Viremia and Prevention of Clinical AIDS in Rhesus Monkeys by Cytokine-Augmented DNA Vaccination". Science 290:486-492 (Oct. 2000).
Bauer, et al., "Bacterial CpG-DNA Triggers Activation and Maturation of Human CD11c-, CD123+ Dendritic Cells". J. Immunol. 166:5000-5007 (2001).
Bayever, "Systemic administration of a phosphorothioate oligonucleotide with a sequence complementary to p53 for acute myelogenous leukemia and myelodysplastic syndrome: initial results of a Phase I trial". Antisense Res. Dev. 3:383-390 (1993).
Benimetskaya, et al., "Formation of a G-tetrad and higher order structures correlates with biological activity of the ReIA (NF-kBp65) 'antisense' oligodeoxynucleotide". Nucleic Acids Research 25(13):2648-2656 (1997).
Bennett, et al., "DNA binding to human leukocytes: evidence for a recptor-mediated association, internalization, and degradation of DNA". J. Clin. Invest. 76(6):2182-2190 (1985).
Berg, et al., "Interleukin-10 is a central regulator fo the response to LPS in murine models of endotoxic shock and the Shwartzman reacton but not endotoxin tolerance". J. Clin. Invest. 96(5):2339-2347 (1995).
Biolabs, "1988-1989 Catalog, Random Primer #s 1230, 1601, 1602". ( ).
Bishop, et al., "Intramolecular G-quartet Motifs Confer Nuclease Resistance to a Potent Anti-HIV Oligonucleotide". The Journal of Biological Chemistry 271(10):5698-5703 (Mar. 1996).
Blanchard, et al., "Interferon-γ Induction by Lipopolysaccharide: Dependence of Interleukin 2 and Macrophages". The Journal of Immunology 136(3):963-970 (Feb. 1986).
Blanco, et al., "Induction of Dendritic Cell Differentiation by IFN-60 in Systemic Lupus Erythermatosus". Science 294:1540-1543 (2001).
Blaxter, et al., "Genes expressed in Brugia malayi infective third stage larvae". Mol. Biochem. Parasitol. 77:77-93 (1996).

Boggs, et al., "Characterization and modulation of immune stimulation by modified oligonucleotides". Antisense Nucl. Acid Drug Dev. 7(5):461-471 (1997).

Boiarkina, et al., "Dietary supplementals from ground fish meat with DNA for treatment and prophylaxis". Vopr. Pitan 1:29-31 (1998), abstract.

Branda, et al., "Immune stimulation by an antisense oligomer complementary to the rev gene of HIV-1". Biochem. Pharmacol. 45(10):2037-2043 (1993).

Branda, et al., "Amplification of antibody production by phosphorothioate oligodeoxynucleotides". J. Lab Clin. Med. 128(3):329-338 (1996).

Briskin, et al., "Lipopolysaccharide-unresponsive mutant pre-B-cell lines blocked in NF-kappa B activation". Mol. Cell Bio. 10(1):422-425 (1990).

Burgess, "The antiproliferative activity of c-myb and c-myc antisense oligonucleotides in smooth muscle cells is caused by a nonantisense mechanism". Proc. Natl. Acad. Sci. USA 92:4051-4055 (Apr. 1995).

Calarota, et al., "Immune Responses in Asymptomatic HIV-1 Infected Patients After HIV-DNA Immunization Followed by Highly Active Antiretroviral Threatment". J. Immunol. 163(4):2330-2338 (1999).

Chace, et al., "Regulation of differentiation in CD5+ and conventional B cells". Clin. Immunol. Immunopathol. 68(3):327-332 (1993).

Chang, et al., "The palindromic series I repeats in the simian cytomegalovirus major immediate-early promoter behave as both strong basal enhancers and cyclic AMP response elements". J. Virol. 64(1):264-277 (1990).

Chapuis, et al., "Differentiation of Human Dendritic Cells from Monocytes in vitro". Eur. J. Immunol. 27:431-441 (1997).

Chehimi, "Persistent Decreases in Blood Plasmacytoid Dendritic Cell Number and Function Despite Effective Highly Active Antiretroviral Therapy and Increased Blood Myeloid Dendritic Cells in HIV-Infected Individuals". J. Immunol. 168(9):4796-4801 (2002).

Chu, et al., "CpG oligodeoxynucleotides act as adjuvants that switch on T helper 1 (Th1) immunity". J. Exp. Med. 186(10):1623-1631 (1997).

Chun, et al., "Effect of interleukin-2 on the pool of latently infected, resting CD4+ T-cells in HIV-1-infected patients receiving highly active anti-retroviral therapy". Nature Med. 5(6):651-655 (1999).

Chun, et al., "Perspective: Latent reservoirs of HIV: Obstacles to the eradication of virus". Proc. Natl. Acad. Sci. USA 96:10958-10961 (1999).

Cohen, et al., "Exploring How to Get at—and Eradicate—Hidden HIV". Science 279:1854-1855 (1998).

Cohen & Fauci, et al., "HIV/AIDS in 1998—Gaining the Upper Hand?". JAMA 280(1):87-88 (1998).

Cook, et al., "Effect of a Single Ethanol Exposure on HIV Replication in Human Lymphocytes". J. Invest. Med. 45(5):265-271 (1997).

Cooper, et al., "Therapeutic Strategies for HIV Infection—Time To Think Hard". The New England Journal of Medicine 339(18):1319-1321 (1998).

Cowdery, et al., "Bacterial DNA induces NKcells to produce IFN-gamma in vivo and increases the toxici of lipopolysaccharides". J. Immunol. 156(12):4570-4575 (1996).

Crosby, et al., "The early responses gene NGFI-C encodes a zinc finger transcriptional activator and is a member of the GCGGGGGCG (GSG) element-binding protein family". Mol. Cell Bio. 2:3835-3841 (1991).

Crystal, "Transfer of genes to humans: early lessons and obstacles to success". Science 270:404-410 (1995).

Cryz, et al., "Vaccine Delivery System—European Commission COST/STD Initiative Report of the Expert Panel VII". Vaccine 14(7):665-690 (1996).

D'Andrea, et al., "Interleukin 10 (IL-10) inhibits human lymphocyte interferon gamma-production by suppressing natural killer cell stimulatory factor/IL-12 synthesis in accessory cells". J. Exp. Med. 178(3):1041-1048 (1993).

Davey, et al., "HIV-1 and T-Cell dynamics after interruption of highly antiretroviral therapy (HAART) in patients with a history of sustained viral suppression". Proc. Natl. Acad. Sci. USA 96(26):15109-15114 (1999).

Davis, et al., "CpG DNA is a Potent Enhancer of Specific Immunity in Mice Immunized with Recombinant Hepatitis B Surface Antigen". J. Immunol. 160(2):870-876 (1998).

Davis, "Plasmid DNA expression systems for the purpose of immunization". Curr. Opin. Biotechnol. 8(5):635-646 (Oct. 1997).

Dematos, et al., "Pulsing of Dendritic Cells with Cell Lysates from Either B16 Melanoma or MCA-106 Fibrosarcoma Yields Equally Effective Vaccines Against B16 Tumors in Mice". J. Surg. Oncol. 68:79-91 (1998).

Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).

Dias et al., "Antisense Oligonucleotides: Basic Concepts and Mechanisms," *Mol. Cancer Ther*. 1:317-355, 2002.

Doerfler, et al., "On the Insertion of Foreign DNA into Mammalian Genomes: Mechanism and Consequences". Gene 157(1-2):241-254 (1995), abstract.

Durham, et al., "Immunotherapy and Allergic Inflammation". Clin. Exp. Allergy 21 Suppl 1:206-210 (1991).

Eck, et al., "Chapter 5: Gene-Based Therapy". Goodman & Gilman's The Pharmacological Basis of Therapeutics 9th ed.:77-101 (1996).

Elkins, et al., "Bacterial DNA containing CpG motifs stimulates lymphocyte-dependent protection of mice against lethal infection with intracellular bacteria". J. Immunol. 162:2291-2298 (1999).

Englisch, et al., "Chemically modified oligonucleotides as probes and inhibitors". Angew. Chem. Int. Ed. Engl. 30:613-629 (1991).

Erb, et al., "Infection of mice with Mycobacterium bovis-badillus Calmette-Guerin (BCG) supresses allergen-induced airway eosinophilia". J. Exp. Med. 184(4):561-569 (1998).

Etlinger, "Carrier sequence selection—one key to successful vaccines". Immunology Today 13(2):52-55 (1992).

Fanslow, et al., "Effect of Nucleotide Restriction and Supplementation on Resistance to Experimental Murine Candidasis". J. Parenter. Enteral. Nutr. 12(1):49-52 Abstract (1988).

Fields, et al., "Murine Dendritic Cells Pulsed With Whole Tumor Lysates Mediate Potent Antitumor Immune Responses in vitro and in vivo". Proc. Natl. Acad. Sci. USA 95:9482-9487 (1998).

Filion, et al., "Major Limitations in the use of Cationic Liposomes for DNA Delivery". Int. J. Pharmaceuticals 162:159-170 (1998).

Fox, "Mechanism of actin of hydroxychloroquine as an antirheumatic drug". Chem. Abstracts 120:15, Abstract No. 182630 (1 page) (1994).

Freidag, et al., "CpG oligodeoxynucleotides and interleukin-12 improve the efficacy of Mycobacterium bovis BCG vaccination in mice challenged with M. tuberculosis". Infect. Immun. 68:2948-2953 (2000).

Gao, et al., "Phosphorothioate oligonucleotides are inhibitors of human DNA polymerases and Rnase H: Implications for antisense technology". Mol. Pharmacol. 41:223-229 (1992).

Garraud, "Regulation of Immunoglobin Production in Hyper-IgE (Job's) Syndrome". J. Allergy Clin. Immunol. 103(2 Pt 1):333-340 (Feb. 1999).

Gluckman, et al., "In Vitro Generation of Human Dendritic Cells and Cell Therapy". Cytokines Cell Mol. Ther. 3:187-196 (1997).

Gramzinski, et al., "Interleukin-12- and gamma interferon-dependent protection against malaria conferred by CpG oligodeoxynucleotide in mice". Infect. Immun. 69(3):1643-1649 (2001).

Gura, "Antisense has growing pains". Science 270:575-576 (1995).

Gursel, "Sterically Stabilized Cationic Liposomes Improve the Uptakeand Immunostimulatory Activity of CpG Oligonucleotides". J. Immunol. 167(6):3324-3328 (2001).

Gursel, et al., "Differential and Competitive Activation of Human Immune Cells by Distinct Classes of CpG Oligodeoxynucleotide". J. Leuko. Biol. 71:813-820 (2002).

Hadden, et al., "Immunopharmacology". JAMA 268(20):2964-2969 (1992).

Hadden, et al., "Immunostimulants". TiPS 141:169-174 (1993).

Halpern, et al., "Bacterial DNA induces murine interferon-gamma production by stimulation of interleukin-12 and tumor necrosis factor-alpha". Cell Immunol. 167(1):72-78 (1996).

Haslett, et al., "Strong Human Immunodificiency Virus (HIV) Specific CD4+ T Cell Responses in a Cohort of Chronically Infected Patients are Associated with Interruptions in Anti-HIV Chemotherapy". J. Infect. Diseases 181:1264-1272 (2000).

Hatzfeld, "Release of early human hematopoietic progenitors from quiescence by antisense transformin owth factor β1 or Rb oligonucleotides". J. Exp. Med. 174:925-929 (1991).

Havlir, et al., "Maintenance Antiretroviral Therapies in HIV-Infected Subjects with Undetectable Plasma HIV RNA after Triple-Drug Therapy". The New England Journal of Medicine 339(18):1261-1268 (1998).

Hayashi, et al., "Enhancement of innate immunity against Mycobacterium avium infection by immunostimutatory DNA is mediated by indoteamine 2,3-dioxygenase". Infect. Immun. 69:6156-6164 (2001).

Hertl, et al., "Inhibition of Interferon-γ-Induced Intercellular Adhesion Molecule-1 Expression on Human Keratinocytes by Phosphorothioate Antisense Oligodeoxynucleotides is the Consequence of Antisense-Specific and Antisense-Non-Specific Effects". The Journal of Investigative Dermatology 104(5):813-818 (May 1995).

Highfield, "Sepsis: the more, the murkier". Biotechnology 12:828 (1994).

Hoeffler, et al., "Identification of multiple nuclear factors that interact with cyclic adenosine 3',5'-monophosphate response element-binding protein and activating transcription factor-2 by protein-protein interactions". Mol. Endocrinol. 5(2):256-266 (1991).

Honess, et al., "Deviations from Expected Frequencies of CpG Dinucleotides in Herpesvirus DNAs May be Diagnostic of Differences in the States of Their Latent Genomes". J. Gen. Vir. 70(4):837-855 (1989).

Horspool, et al., "Nucleic acid vaccine-induces immune responses require CD28 costimulation and are regulated by CTLA4". J. Immunol. 160:2706-2714 (1998).

Hughes, et al., "Influence of Base Composition on Membrane Binding and Cellular Uptake of 10-mer Phosphorothioate Oligonucleotides in Chinese Hamster Ovary (CHRC5) Cells". Antisense Research and Development 4:211-215 (1994).

Iguchi-Ariga, et al., "CpG methylation of the cAMP-responsive enhancer/promoter sequence TGACGTCA abolishes specific factor binding as well as transcriptional activation". Genes Dev. 3(5):612-619 (1989).

Imami, et al., "Assessment of Type 1 and Type 2 Cytokines in HIV Type 1-Infected Individuals: Impact of Highly Active Antiretroviral Therapy". Aids Research and Human Retroviruses 15(17):1499-1508 (1999).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).

Ishikawa, et al., "IFN induction and associated changes in splenic leukocyte distribution". J. Immunol. 150(9):3713-3727 (1993).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).

Jakway, et al., "Growth regulation of the B lymphoma cell line WEHI-23 1 by anti-immunoglobulin, lipopolysaccharide, and other bacterial products". J. Immunol. 137(7):2225-2231 (1996).

Jaroszewski, et al., "Cellular uptake of antisense oligonucleotides". Adv. Drug Delivery Rev. 6(3):235-250 (1991).

Jilek, et al., "Antigen-Independent Suppression of the Allergic Immune Response to Bee Venom Phospholipase A2 by DNA Vaccination in CBA/J Mice". J. Immunol. 166:3612-3621 (2001).

Jones, et al., "Synthetic Oligonucleotides Containing CpG Motifs Enhance Immunogenicity of a Peptide Malaria Vaccine in Aotus Monkeys". Vaccine 17:3065-3071 (1999).

Juffermans, et al., "CpG oligodeoxynucleotides enhance host defense during murine tuberculosis". Infect. Immun. 70:147-152 (2002).

Kadowaki, et al., "Distinct CpG DNA and Polyinosinic-Polycytidylic Acid Double Stranded RNA, Respectively, Stimulate CD11c- Type 2 Dendritic Cell Precursoes and CD11c+ Dendritic cells to Produce Type I IFN". J. Immunol. 166:2291-2295 (2001).

Kataoka, et al., "Antitumor activity of synthetic oligonucleotides with sequences from cDNA encodin proteins of Mycobacterium bovis BCG". Jpn. J. Cancer Res. 83:244-247 (1992).

Kenney, et al., "Protective Immunity Using Recombinant Human IL-12 and Alum as Adjuvants in a Primate Model of Cutaneous Leishmaniasis". J. Immunol. 163(8):4481-4488 (1999).

Khaled, et al., "Multiple mechanisms may contribute to the cellular anti-adhesive effects of phosphorothioate oligodeoxynucleotides". Nucleic Acids Research 24(4):737-745 (1996).

Kimura, et al., "Binding of oligoguanylate to scavenger receptors is required for oligonucleotides to augment NK cell activity and induce IFN". J. Biochem 116(5):991-994 (1994).

Kline, et al., "CpG motif oligonucleotides are effective in prevention of eosinophilic inflammation in a murine model of asthma". J. Invest. Med. 44(7):380A (1 page) (1996).

Kline, et al., "CpG oligonucleotides can reverse as well as prevent TH2-mediated inflammation in a murine model of asthma". J. Invest. Med. 45(7):298A (1 page) (1997).

Kline, et al., "Immune redirection by CpG oligonucleotides, Conversion of a Th2 response to a Th1 response in a murine model of asthma". J. Invest. Med. 45(3):282A (1 page) (1997).

Klinman, et al., "Immune recognition of foreign DNA: a cure for bioterrorism?". Immunity 11:123 (1 page) (1999).

Klinman, et al., "Repeated administration of synthetic oligodeoxynucteotides expressing CpG motifs provides tong-term protection against bacterial infection". Infect. Immun. 67:5658-5663 (1999).

Klinman, et al., "CpG motifs present in bacteria DNA rapidly induce lymphocytes to secrete interleukin 6, interleukin 12, and interferon gamma". Proc. Natl. Acad. Sci. USA 93(7):2879-2883 (1996).

Klinman, et al., "Activation of the innate immune system by CpG oligodeoxynucleotides: immunoprotective activity and safety". Springer Semin. Immunopathol. 22:173-183 (2000).

Klinman, et al., "CpG Motids as Immune Adjuvants". Vaccine 17:19-25 (1999).

Kou, et al., "Analysis and Regulation of interferon-gamma production by peripheral blood lymphocytes from patients with bronchial asthma". Arerugi 43(3):483-491 (1994), abstract.

Krieg, et al., "CpG motifs in bacterial DNA and their immune effect". Annu. Rev. Immunol. 20:709-760 (2002).

Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).

Krieg, et al., "Phosphorothioate oligodeoxynucleotides: antisense or anti-protein?". Antisense Res. Dev. 5:241 (1 page) (1995).

Krieg, et al., "Uptake of oligodeoxyribonucleotides by lymphoid cells is heterogeneous and inducible". Antisense Res. Dev. 1(2):161-171 (1991).

Krieg, et al., "Leukocyte stimulation by oligodeoxynucleotides". Applied Antisense Oligonucleotide Tech. (Book):431-448 (1998).

Krieg, et al., "Causing a Commotion in the Blood: Immunotherapy Progresses from Bacteria to Bacterial DNA". Immunology Today 21(10):521-526 (2000).

Krieg, et al., "CpG DNA: A pathogenic factor in systemic lupus erythematosus?". J. Clin. Immunol. 15(6):284-292 (1995).

Krieg, et al., "CpG DNA induces sustained IL-12 expression in vivo and resistance to Listeria monocytogenes challenge". J. Immunol. 161:2428-2434 (1998).

Krieg, et al., "A role for endogenous retroviral sequences in the regulation of lymphocyte activation". J. Immunol. 143(8):2448-2451 (1989).

Krieg, "An innate immune defense mechanism based on the recognition of CpG motifs in microbial DNA". J. Lab. Clin. Med. 128(2):128-133 (Abstract) (1996).

Krieg, et al., "CpG motifs in bacterial DNA trigger direct B-cell activation". Nature 374:546-549 (1995).

Krieg, et al., "Modification of antisense phosphodiester oligodeoxynucleotides by a 5' cholesteryl moiety increases cellular association and improves efficacy". Proc. Natl. Acad. Sci. USA 90:1048-1052 (1993).

Krieg, et al., "The role of CpG dinucleotides in DNA vaccines". Trends in Microbiol. 6:23-27 (1998).

Krieger, et al., "Structures and Functions of Multiligand Lipoprotein Receptors: Macrophage Scavenger Receptors and LDL Receptor-Related Protein (LRP)". Annu. Rev. Biochem 63:601-637 (1994).

Krug, et al., "Identification of CpG Oligonucleotide Sequences with High Induction of IFN-α/β in Plasmacytoid Dendritic Cells". Eur. J. Immunol. 31:2154-2163 (2001).

Krug, et al., "Toll-like Receptor Expression Reveals CpG DNA as a Unigue Microbial Stimulus for Plasmacytoid Dendritic Cells Which Synergizes With CD40 Ligand to Induce High Amounts of IL-12". Eur. J. Immunol. 31:3026-3037 (2001).

Kuchan, et al., "Nucleotides in Infant Nutrition: Effects of Immune Function". Pediatr. Adolesc. Med. Basel. Karger 8:80-94 (1998).

Kulkarni, et al., "Effect of Dietary Nucleotides on Response to Bacterial Infection". J. Parenter. Enteral. Nutr. 10(2):169-171 Abstract (1986).

Kuramoto, et al., "Oligonucleotide sequences required for natural killer cell activation". Jpn. J. Cancer Res. 83:1128-1131 (1992).

Lagrange, et al., "Immune Responses Directed Against Infectious and Parasitic Agents". Immunology (Book—ISBN:0471017604) (Chapter of Book; Ed—Jean-François Bach): (1978).

Lang, et al., "Guanosine-rich oligodeoxynucleotides induce proliferation of macrophage progenitors in cultures of murine bone marrow cells". Eur. J. Immunol. 29:3496-3506 (1999).

Lapatschek, et al., "Activation of Macrophages and B Lymphocytes by an Oligonucleotide Derived from an Acutely Pathogenic Simian Immunodeficiency Virus". Antisense Nucleic Acid Drug Dev. 8(5):357-370 (Oct. 1998).

Ledergerber, et al., "Clinical Progression and Virological Failure on Highly Active Antiretroviral Therapy in HIV-1 Patients: a Prospective Cohort Study". The Lancet 353:863-868 (1999).

Lederman, et al., "Polydeoxyguanine Motifs in a 12-mer Phosphorothioate Oligodeooxynucleotide Augment Binding to the v3 Loop of the HIV-1 gp120 and Potency of HIV-1 Inhibition Independently of G-Tetrad Formation". Antisense & Nucleic Acid Drug Development 6:281-289 (1996).

Lee, et al., "An Oligonucleotide Blocks Interferon-γ Signal Transduction". Transplantation 62(9):1297-1301 (1996).

Leibson, et al., "Role of γ-interferon in antibody-producing responses". Nature 309:799-801 (1984).

Leonard, et al., "Conformation of guanine 8-oxoadenine base pairs in the crystal structure of d(CGCGAAT(O8A)GCG)". Biochemistry 31(36):8415-8420 (1992).

Li, et al., "Long-Lasting Recovery in CDR T-Cell Function and Viral-Load Reduction After Highly Active Antiretroviral Therapy in Advanced HIV-1 Disease". The Lancet 351:1682-1686 (1998).

Liang, et al., "Activation of Human B Cells by Phosphorothioate Oligodeoxynucleotides". J. Clin. Invest. 98:1119-1129 (1996).

Lipford, et al., "CpG-containing synthetic oligonucleotides promote B and cytotoxic T cell responses to protein antigen: a new class of vaccine adjuvants". Eur. J. Immunol. 27(9):2340-2344 (1997).

Lipford, et al., "Immunostimulatory DNA: sequence-dependent production of potentially harmful or useful cytokines". Eur. J. Immunol. 27(12):3420-3426 (1997).

Lönnberg, et al., "Towards Genomic Drug Therapy with Antisense Oligonucleotides". Ann. Med. 28:511-522 (1996).

Macaya, et al., "Thrombin-binding DNA aptamer forms a unimolecular quadruplex structure in solution". Proc. Natl. Acad. Sci. USA 90:3745-3749 (Apr. 1993).

MacFarlane, et al., "Antagonism of immunostimulatory CpG-oligodeoxynucleotides by quinacrine, chloroquine, and structurally related compounds". J. Immunol. 160(3):1122-1131 (1998).

Maddon, "The Isolation and Nucleotide Sequence of a cDNA Encoding the T Cell Surface Protein T4: A New Member of the Immunoglobin Gene Family". Cell 42(1):93-104 (1985).

Maltese, et al., "Sequence context of antisense RelA/NF-kB phohphorothioates determines specificity". Nucleic Acids Research 23(7):1146-1151 (1995).

Manzel, et al., "Lack of Immune Stimulation by Immobilized CpG-oligonucletide". Antisense & Nucleic Acid Drug Development 9(5):459-464 (1999).

Mastrangelo, et al., "Gene therapy for human cancer: an essay for clinicians". Seminars Oncology 23(1):4-21 (1996).

Matson, et al., "Nonspecific suppression of [3H]thymidine incorporation by control oligonucleotides". Antisense Res. Dev. 2(4):325-330 (1992).

McCluskie, et al., "Cutting Edge: CpG DNA Is a Potent Enhancer of Systemic and Mucosal Immune Responses Against Hepatitis B Surface Antigen with Intranasal Administration to Mice". J. Immun. 161:4463-4465 (1998).

McCluskie, et al., "Route and Method of DNA Vaccine Influence Immune Responses in Mice and Non-Human Primates". Molecular Med. 5(5):287-300 (1999).

McIntyre, et al., "A sense phosphorothioate oligonucleotide directed to the initiation codon of transcription factor NF-kappa B p65 causes sequence-specific immune stimulation". Antisense Res. Dev. 3(4):309-322 (1993).

McKenzie, "Nucleic Acid Vaccines". Immunologic Res. 24(3):225-244 (2001).

Merad, et al., "In vivo Manipulation of Dendritic Cells to Induce Therapeutic Immunity". Blood 99(5):1676-1682 (2002).

Messina, et al., "Stimulation of in vitro murine lymphocyte proliferation by bacterial DNA". Cell Immunol. 147(6):1759-1764 (1991).

Messina, et al., "The influence of DNA structure on the in vitro stimulation of murine lymphocytes by natural and synthetic polynucleotide antigens". J. Immunol. 147:148-157 (1993).

Mojcik, et al., "Administration of a phosphorothioate oligonucleotide antisense murine endogenous retroviral MCF env causes immune effect in vivo in a sequence-specific manner". Clin. Immunol. Immunopathol. 67(2):130-136 (1993).

Moss & Lederman, "Immunication of the Immunocompromised Host". Clinical Focus on Primary Immune Deficiencies 1(1):1-3 (1998).

Mottram, et al., "A novel CDC2-related protein kinase from leishmania mexicana, LmmCRK1, is post-translationally regulated during the life cycle". J. Biol. Chem. 268(28):21044-21052 (1993).

Nyce, et al., "DNA antisense therapy for asthma in an animal model". Nature 385:721-725 (1997).

Oberbauer, "Not nonsense but antisense—Applications of Antisense Oligonucleotides in Different Fields of Medicine". Wein Klin Wochenschr 109:40-46 (1997).

Ogg, et al., "Quantitation of HIV-1-Specific Cytotoxic T-Lymphocytes and Plasma Load of Viral RNA". Science 279:2103-2106 (1998).

Okada, et al., "Bone Marrow-Derived Dendritic Cells Pulsed With a Tumor-Specific Peptide Elicit Effective Anti-Tumor Immunity Against Intracranial Neoplasms". Int. J. Cancer 78:196-201 (1998).

Palucka, et al., "Dendritic Cells as the Terminal Stage of Monocyte Differentiation". J. Immunol. 160:4587-4595 (1999).

Papasavvas, et al., "Enhancement of Human Immunodeficiency Virus Type I-Specific CD4 and CD8 T Cell Responses in Chronically Infected Persons after Temporary Treatement Interruption". J. Infect. Diseases 182:766-775 (2000).

Pialoux, et al., "A Randomized Trial of Three Maintenance Regimens Given After Three Months of Induction Therapy with Zidovudine, Lamivudine, and Indinavie in Previously Untreated HIV-1-Infected Patients". The New England Journal of Medicine 339(18):1269-1276 (1998).

Piscitelli, "Immune-Based Therapies for Treatment of HIV Infection". The Annals of Pharmacotherapy 30:62-76 (1996).

Pisetsky, et al., "Immunological Properties of Bacterial DNA". Ann. NY Acad. Sci. 772:152-163 (1995).

Pisetsky, "Immunological consequences of nucleic acid therapy". Antisense Res. Dev. 5:219-225 (1995).

Pisetsky, "The immunological properties of DNA". J. Immunol. 156:421-423 (1996).

Pisetsky, et al., "Stimulation of murine lymphocyte proliferation by a phosphorothioate oligonucleotide with antisense activity for hepes simplex virus". Life Science 54:101-107 (1994).

Pisetsky, "Stimulation of in vitro proliferation of murine lymphocytes by synthetic oligodeoxyucleotides". Molecular Biol. Reports 18:217-221 (1993).

Plenat, "Animal models of antisense oligonucleotides: lessons for use in humans". J. Mol. Med. Today 2(6):250-257 (1996).

Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide". Antimicrobial Agents and Chemotherapy 43(11):2689-2696 (Nov. 1999).

Quddus, et al., "Treating activated CD4+ T cells with either of two distinct DNA methyltransferase inhibitors, 5-azacytidine or procaniamide, is sufficient to cause a lupus-like disease in syngeneic mice". J. Clin. Invest. 92(1):38-53 (1993).

Ramanathan, et al., "Characterization of the Oligodeoxynucleotide-mediated Inhibition of Interferon-γ-induced Major Histocompatibility Complex Class I and Intercellular Adhesion Molecule-1". The Journal of Biological Chemistry 269(40):24564-24574 (Oct. 1994).

Ramanathan, et al., "Inhibition of Interferon-γ-Induced Major Histocompatibility Complex Class I Expression by Certain Oligodeoxynucleotides". Transplantation 57(4):612-615 (Feb. 1994).

Raz, "Deviation of the Allergic IgE to an IgG Response by Gene Immunotherapy". Int. Rev. Immunol. 18(3):271-289 (1999).

Raz, et al., "Preferential Induction of a Th1 Immune Response and Inhibition of Specific IgE Antibody Formation by Plasmid DNA Immunization". Proc. Natl. Acad. Sci. USA 93:5141-5145 (1996).

Raz, et al., "Intradermal gene immunization: the possible role of DNA uptake in the induction of cellular immunity to viruses". Proc. Natl. Acad. Sci. USA 91:9519-9523 (1994).

Ricci, et al., "T cells, cytokines, IgE and allergic airways inflammation". J. Invest. Allergol Clin. Immunol. 4(5):214-220 (1994).

Rojanasakul, "Antisense oligonucleotide therapeutics: drug delivery and targeting". Drug Delivery Reviews 18:115-131 (1996).

Roman, et al., "Immunostimulatory DNA sequences function as T helper-1-promoting aduvants". Nature Med. 3(8):849-854 (1997).

Rosenberg, et al., "Immune Control of HIV-1 After Early Treatment of Acute Infection". Nature 407:523-526 (2000).

Rosenberg, et al., "Vigorous HIV-1-Specific CD4+ T-Cell Responses Associated with Control of Viremia". Science 278:1447-1450 (1997).

Ruiz, et al., "Structured Treatment Interruption in Chronically HIV-1 Infected Patients After Long-Term Viral Suppression". AIDS 14:397-403 (2000).

Santini, et al., "Type I Interferon as a Powerful Adjuvant for Monocyte-derived Dendritic Cell Development and Activity In Vitro and in Hu-PBL-SCID Mice". J. Exp. Med. 191:1777-1788 (2000).

Sato, et al., "Immunostimulatory DNA sequences necessary for effective intradermal gene immunization". Science 273:352-354 (1996).

Scanlon, et al., "Oligonucleotide-mediated Modulation of Mammalian Gene Expression". FASEB J. 9:1288-1295 (1995).

Schnell, et al., "Identification and characterization of a Saccharomyces cerevisiae gene (PAR 1) conferring resistance to iron chelators". Eur. J. Biochem. 200:487-493 (1991).

Schoofs, "Small Steps—A Limited Experiment Opens New Approach in Fight Against HIV". Wall Street Journal (Sep. 28, 2000).

Schubbert, et al., "Ingested Foreign (phage M13) DNA Survives Transiently in the Gastrointestinal Tract and Enters the Bloodstream of Mice". Mol. Gen. Genet. 242:495-504 (1994).

Schwartz, et al., "Endotoxin responsiveness and grain dust-induced inflammation in the lower respiratory tract". Am. J. Physiol. 267(5):609-617 (1994).

Schwartz, et al., "The role of endotoxin in grain dust-induced lung disease". Am. J. Respir. Crit. Care Med. 152(2):603-608 (1995).

Schwartz, et al., "CpG motifs in bacterial DNA cause inflammation in the lower respiratory tract". J. Clin. Invest. 100(1):68-73 (1997).

Sedegah, et al., "Intertukin 12 induction of interferon g-dependent protection against malaria". Proc. Natl. Acad. Sci. USA 91:10700-10792 (1994).

Sethi, et al., "Postexposure prophytaxis against prion disease with a stimulator of innate immunity". Lancet 360:229-230 (2002).

Shafer, et al., "Highly Active Antiretroviral Therapy (HAART) for the Treatment of Infection With Human Immunodeficiency Virus Type 1". Biomed. & Pharmachther. 53:73-86 (1999).

Shirakawa, et al., "The inverse association between tuberculin responses and atopic disorder". Science 275(5296):77-79 (1997).

Sidman, et al., "γ-Interferon is one of several direct B cell-maturing lymphokines". Nature 309:801-804 (1984).

Sparwasser, et al., "Macrophages sense pathogens via DNA motifs: induction of tumor necrosis factor-alpha-mediated shock". Eur. J. Immunol. 27(7):1671-1679 (1997).

Sparwasser, et al., "Bacterial DNA and immunostimulatory CpG oligonuceotides trigger maturation and activation of murine dendritic cells". Eur. J. Immunol. 28:2045-2054 (1998).

Spiegelberg, et al., "Recognition of T Cell Epitopes and Lymphokine Secretion by Rye Grass Allergen Lolium perenne I-Specific Human T Cell Clones". J. of Immunology 152:4706-4711 (1994).

Stacey, et al., "Immunostimulatory DNA as an adjuvant in vaccination against Leishmania major". Infect. Immun. 67:3719-3726 (1999).

Stein, et al., "Oligodeoxynucleotides as inhibitors of gene expression: a review". Cancer Res. 48:2659-2668 (1998).

Stull, et al., "Antigene, ribozyme, and aptamer nucleic acid drugs: progress and prospects". Pharm. Res. 12(4):465-483 (1995).

Su, et al., "Vaccination against Chlamydial Genital Tract Infection after Immunization with Dendritic Cells Pulsed Ex Vivo with Non-viable Chlamydiae". J. Exp. Med. 188:809-818 (1998).

Subramanian, et al., "Theoretical considerations on the 'spine of hydration' in the minor groove of d(CGCGAATTCGCG) d(CGGCT-TAAGCGC): Monte Carlo computer simulation". Proc. Natl. Acad. Sci. USA 85:1836-1840 (1988).

Syme, et al., "Generation of Dendritic Cells ex vivo: Differences in Steady State versus Mobilized Blood from Patients with Breast Cancer, with Lymphoma, and from Normal Donors". J. Hematother. Stem Cell Res. 10:621-630 (2001).

Tanaka, et al., "An antisense oligonucleotide complementary to a sequence in I gamma 2b increases gamma 2b germhine transcripts, stimulates B cell DNA synthesis and inhibits immunoglobulin secretion". J. Exp. Med. 175:597-607 (1992).

Tarte, et al., "Extensive characterization of dendritic cells generated in serum-free conditions: regulation of soluble antigen uptake, apoptotic tumor cell phagocytosis, chemotaxis and T cell activation during maturation in vitro". Leukemia 14:2182-2192 (2000).

Thorne, "Experimental grain dust atmospheres generated by wet and dry aerosolization techniques". Am. J. Ind. Med. 25(1):109-112 (1994).

Tighe, et al., "Conjunction of Protein to Immunostimulatory DNA results in a Rapid Long-Lasting and Potent Induction of Cell-Mediated and Humoral Immunity". Eur. J. Immunol. 30:1939-1947 (2000).

Tokunaga, et al., "A synthetic single-stranded DNA, poly(dG, dC), induces interferon-α/β and -γ, augments natural killer activity and suppresses tumor growth". Jpn. J. Cancer Res. 79:682-686 (1988).

Tokunaga, et al., "Synthetic oligonucleotides with particular base sequences from the cDNA encoding proteins of Mycobacterium bovis BCG induce interferons and activate natural killer cells". Microbiol. Immunol. 36(1):55-66 (1992).

Uhlmann, et al., "Antisense oligonucleotides: a new therapeutic principle". Chem. Rev. 90:543-584 (1990).

Verdijk, et al., "Polyriboinosinic Polyribocytidylic Acid (Poly(I:C)) Induces Stable Maturation of Functionally Active Human Dendritic Cells". J. Immunol. 163:57-61 (1999).

Verma, et al., "Gene therapy—promises, problems and prospects". Nature 389:239-242 (Sep. 1997).

Verthelyi, et al., "Human Peripheral Blood Cells Differentially Recognize and Respond to Two Distinct CpG Motifs". J. Immunol. 166:2372-2377 (2001).

Verthelyi, et al., "CpG Oligodeoxynucleotides as Vaccine Adjuvants in Primates". J. Immunol. 168:1659-1663 (2002).

Vil'ner, "Effect of Amphotericin B on the interferonogenic activity of poly(G).poly (C) and poly(G,I).poly(C) in mice and their resistance to infection by the tick-borne encephalitis virus". Antibiotiki 27(11):827-830 (Nov. 1982), abstract.

Vil'ner, et al., "Effect of virazole on the antiviral activity of poly(G) X poly© and other polyribonucleotide interferongens". Antibiotiki 29(6):450-453 (1984), abstract.

Vil'ner, et al., "Evaluation of the size of the continuous poly(G) site necessary for the biological activity of the poly(G).poly(C) complex". Vopr Virusol 30(3):337-340 (1985), abstract.

Vil'ner, "Effect of the size of the continuous poly(G) site in poly(G,A).poly(C) complexes on their interferon-inducing activity and their capacity to stimulate the development of the immunity". Vopr Virusol 31(6):697-700 (1986), abstract.

Vil'ner, et al., "Dependence of the antiviral activity of the poly(G).poly(C) complex on the size of the continuous poly(C) segments". Vopr Virusol 33(3):331-335 (1988), abstract.

Wagner, "Bacterial CpG DNA Activates Immune Cells to Signal Infectious Danger". Adv. Immunol. 73:329-368 (1999).

Wagner, "Gene inhibition using antisense oligodeoxynucleotides". Nature 372:333-335 (1994).

Walker, et al., "Activated T Cells and Cytokines in Bronchoalveolar Lavages from Patients with Various Lung Diseases Associated with Eosinophilia". Am. J. Respir. Crit. Care Med. 150:1038-1048 (1994).

Walker, et al., "Immunostimulatory oligodeoxynucleotides promote protective immunity and provide systemic therapy for leishmaniasis via IL-12- and IFN-g-dependent mechanisms". Proc. Natl. Acad. Sci. USA 96:6970-6975 (1999).

Wallace, et al., "Oligonucleotide probes for the screening of recombinant DNA libraries". Methods Enzymol. 152:432-442 (1987).

Weiner, "The immunobiology and clinical potential of immunostimulatory CpG oligodeoxynucleotides". Leukocyte Bio. 68:455-463 (2000).

Weiner, et al., "Immunostimulatory oligodeoxynucleotides containing the CpG motif are effective as immune adjuvants in tumor antigen immunization". Proc. Natl. Acad. Sci. USA 94:10833-10837 (1997).

Weiss, "Upping the antisense ante: scientists bet on profits from reverse genetics". Science 139:108-109 (1991).

Whalen, et al., "DNA-Mediated Immunization to the Helatitis B Surface Antigen: Activation and Entrainment of the Immune Response". Ann. NY Acad. Sci. 772:64-76 (1995).

Whalen, "DNA vaccines for emerging infection diseases: what if?". Emerg. Infect. Dis. 2(3):168-175 (1996).

Wloch, et al., "The influence of DNA sequence on the immunostimulatory properties of plasmid DNA vectors". Hum. Gene Ther. 9(10):1439-1447 (Jul. 1998).

Woolridge, et al., "Immunostimulatory oligodeoxynucleotides containing CpG motifs enhance the efficacy of monoclonal antibody therapy of lymphoma". Blood 89:2994-2998 (1997).

Wu, et al., "Receptor-mediated gene delivery and expression in vivo". J. Biol. Chem. 263:14621-14624 (1988).

Wu-Pong, "Oligonucleotides: opportunities for drug therapy and research". Pharmaceutical Tech. 18:102-114 (1994).

Wyatt, et al., "Combinatorially selected guanosine-quartet structure is a potent inhibitor of human immundeficiency virus envelope-mediated cell fusion". Proc. Natl. Acad. Sci. USA 91:1356-1360 (Feb. 1994).

Yamamoto, et al., "Ability of oligonucleotides with certain palindromes to induce interferon production and augment natural killer cell activity is associated with their base length". Antisense Res. Dev. 4:119-123 (1994).

Yamamoto, "Unique palindromic sequences in synthetic oligonucleotides are required to induce inf and augment INF-mediated natural killer activity". J. Immunol. 148(12):4072-4076 (1992).

Yamamoto, et al., "In vitro augmentation of natural killer cell activity and production of interferon-alpha/beta and -gamma with deoxyribonucleic acid fraction from Mycobacterium bovis BCG". Jpn. J. Cancer Res. 79:866-873 (1988).

Yamamoto, et al., "Synthetic oligonucleotides with certain palindromes stimulate interferon production of human peripheral blood lymphocytes in vitro". Jpn. J. Cancer Res. 85:775-779 (1994).

Yamamoto, et al., "Mode of action of oligonucleotide fraction extracted from Mycobacterium bovis BeG". Kekkaku 69(9):29-32 (1994).

Yamamoto, et al., "DNA from bacteria, but not vetebrates, induces interferons, activates natural killer cells, and inhibits tumor growth". Microbiol. Immunol. 36(9):983-997 (1992).

Yamamoto, et al., "Lipofection of synthetic oligodeoxyribonucleotide having a palindromic sequence AACGTT to murine splenocytes enhances interferon production and natural killer activity". Microbiol. Immunol. 38(10):831-836 (1994).

Yaswen, et al., "Effects of Sequence of Thioated Oligonucleotides on Cultured Human Mammary Epithelial Cells". Antisense Research and Development 3:67-77 (1993).

Yew, et al., "Contribution of Plasmid DNA to Inflammation in the Lung After Administration of Cationic Lipid: pDNA Complexes". Hum. Gene Ther. 10(2):223-234 (1999).

Yi, et al., "IFN-γ promotes IL-6 and lgM secretion in response to CpG motifs in bacterial DNA and oligonucleotides". J. Immunol. 156:558-564 (1996).

Yi, et al., "Rapid immune activation by CpG motifs in bacterial DNA". J. Immunol. 157:5394-5402 (1996).

Zelphati, et al., "Inhibition of HIV-1 Replication in Cultured Cells with Antisense Oligonucleotides Encapsulated in Immunoliposomes". Antisense Res. Dev. 3:323 (1993).

Zhang, et al., "Antigen- and Isotype-Specific Immune Responses to a Recombinant Antigen-Allergen Chimeric (RAAC) Protein". J. Immunol. 151:791-799 (1993).

Zhao, et al., "Comparison of cellular binding and uptake of antisense phosphodiester, phosphorothioate, and mixed phosphorothioate and methylphosphonate oligonucleotides". Antisense Res. Dev. 3(1):53-66 (1993).

Zhao, et al., "Stage-specific oligonucleotide uptake in murine bone marrow B-cell precursors". Blood 84(11):3660-3666 (1994).

Zheng, et al., "Contribution of Vascular Endothelial Growth Factor in the Neovascularization Process During the Pathogenesis of Herpetic Stromal Keratitis". J. Vriol. 75(20):9828-9835 (2001).

Zhu, et al., "Macaque blood-derived antigen-presenting cells elicit SIV-specific immune responses". J. Med. Primatol 29:182-192 (2000).

Zimmermann, et al., "CpG oligodeoxynucleotides trigger protective and curative Th1 responses in lethal murine leishmaniasis". J. Immunol. 160:3627-3630 (1998).

Bei et al., *Journal of Immunotherapy* 21(3):159-169, 1998.

Freimark et al., *The Journal of Immunology* 160:4580-4586, 1998.

Gursel et al., *The Journal of Immunology* 167:3324-3328, 2001.

* cited by examiner

TABLE I

EFFICIENCY OF ODN ENCAPSULATION BY DIFFERENT TYPES OF LIPOSOME

| Liposome type | Liposome composition [molar ratio] | % ODN Encapsulation ($OD_{260}$) | % ODN Encapsulation ($^{32}P$) |
|---|---|---|---|
| Neutral | $PC^a$:Chol [1:1] | 46.2 ± 2.3 | 44.7 ± 4.2 |
| Anionic | PC:DOPE:PS [1:0.5:0.25] | 33.5 ± 4.8 | 38.1 ± 2.5 |
| Cationic | DC-Chol:PC:DOPE [4:6:0.06] | 63.5 ± 3.6 | 61.0 ± 4.2 |
| Stealth | Chol:DOPE:PEG-PE [4:6:0.06] | 51.7 ± 6.6 | 53.6 ± 3.7 |
| Cationic-Stealth | DC-Chol:DOPE:PEG-PE [4:6:0.06] | 88.5 ± 5.3 | 90.1 ± 3.4 |

Results show the mean ± SD of 3-5 independent tested preparations. % ODN encapsulation is i) calculated based on the amount of ODN remaining in the supernatant using UV-spectroscopy, and ii) from liposome pellet directly by $^{32}P$-radioactivity. [a] PC: Phosphatidyl choline, Chol: Cholesterol, DOPE: Dioleyl phosphatidyl choline, PS: Phosphatidyl serine, DC-CHOL: Dimethylaminoethane-carbamol-cholesterol, PEG-PE: Polyethylene glycol$_{2000}$-phosphatidyl ethanolamine

Figure 6

TABLE II

CSL ENCAPSULATION ENHANCES CpG ODN UPTAKE IN VIVO

| TREATMENT | SPLEEN | | PEC | | LN | |
|---|---|---|---|---|---|---|
| | 2h | 24h | 2h | 24h | 2h | 24h |
| PBS | 0.38 ± 0.23 | 0.40 ± 0.13 | 0.47 ± 0.21 | 0.68 ± 0.19 | 0.15 ± 0.06 | 0.25 ± 0.16 |
| CpG ODN | 0.63 ± 0.11 | 1.12 ± 0.33 | 23.02 ± 8.42 | 29.86 ± 6.19 | 0.18 ± 0.07 | 0.83 ± 0.34 |
| (CpG ODN)$_{SSCL}$ | 6.43 ± 1.48 | 8.66 ± 2.30 | 88.76 ± 7.17 | 84.81 ± 10.41 | 0.19 ± 0.08 | 4.69 ± 1.10 |

Balb/c mice (3/group) were injected IP with 50 μg of FITC-labeled free or liposome encapsulated CpG ODN. Animals were sacrificed after 2 or 24 h, and ODN uptake in the spleen, PEC, and LN assessed by FACS.

Figure 7

TABLE III

LIPOSOME ENCAPSULATED CpG ODN ENHANCES CYTOKINE PRODUCTION IN VIVO

| Time post treatment (h) | Treatments | IL 6 [ng/ml] | IL 12 [ng/ml] | IFNγ [pg/ml] | CD40 expressing cells (%) |
|---|---|---|---|---|---|
| 2 | PBS | 0.08 ± 0.02 | 0.21 ± 0.02 | 3.08 ± 0.22 | ND |
|  | CpG ODN | 0.31 ± 0.01 | 0.58 ± 0.28 | 27.28 ± 11.02 | ND |
|  | (CpG ODN)$_{SSCL}$ | 1.87 ± 0.12 | 6.43 ± 1.19 | 178.42 ± 12.32 | ND |
| 24 | PBS | 0.08 ± 0.02 | 0.21 ± 0.02 | 3.08 ± 0.22 | 0.00 |
|  | CpG ODN | 0.16 ± 0.05 | 0.45 ± 0.11 | 13.16 ± 9.65 | 0.01 |
|  | (CpG ODN)$_{SSCL}$ | 1.43 ± 0.42 | 7.69 ± 0.86 | 224.30 ± 16.33 | 0.78 |
| 48 | PBS | 0.08 ± 0.02 | 0.21 ± 0.02 | 3.08 ± 0.22 | ND |
|  | CpG ODN | 0.18 ± 0.07 | 0.32 ± 0.23 | 5.31 ± 2.07 | ND |
|  | (CpG ODN)$_{SSCL}$ | 1.32 ± 0.35 | 5.69 ± 1.26 | 186.12 ± 19.85 | ND |

Balb/c mice (3/group) were injected IP with 50 µg of ODN. Spleen cells ($10^7$/ml) were isolated 2 - 48 h later. Incubated in vitro for 36 h. Cytokine production was detected by ELISA. Results represent the mean ± SD. CD40 expressing cells were isolated 24h after FITC-ODN injection. They were fixed and stained with PE-labeled anti-CD40 Mab and studied by FACS.

Figure 8

Table IV

CO-ENCAPSULATION OF OVA PLUS CpG ODN IN SSCL IMPROVES IMMUNOGENICITY

| Treatments | IgG | IgG1 | IgG2a | IFNγ [pg/ml] |
|---|---|---|---|---|
| PBS | 35 ± 5 | 62 ± 15 | 11 ± 5 | 29 ± 2 |
| Ova | 530 ± 50 | 320 ± 20 | 72 ± 20 | 47 ± 5 |
| Ova + CpG ODN | 1650 ± 350 | 200 ± 5 | 450 ± 90 | 56 ± 5 |
| (CpG ODN)$_{SSCL}$ + Ova | 9300 ± 3100 | 4600 ± 700 | 6200 ± 1740 | 386 ± 40 |
| (CpG ODN+Ova)$_{SSCL}$ | 19000 ± 2300 | 2220 ± 750 | 29000 ± 4600 | 700 ± 90 |

Balb/C mice (3/group) were injected I.P with 2 μg ovalbumin plus 10 μg CpG ODN. They were boosted on day 14 and sacrificed on day 28. Results show mean ± SD serum anti-Ova titers and spleen cell supernatant INFγ (pg/ml) at day 28. To detect IFNγ spleen cells were incubated in vitro for 36 h and supernatants studied by ELISA.

Figure 9

TABLE V The sequence of CpG ODN potentially useful for encapsulating in SSCL

A) K Class ODN

| ODN | Sequence (5'→3') |
|-----|------------------|
| K1 | A G C T G T C G T T T T C T G T C G T T C T C |
| K2 | A T C G A C T C T C G A G C G T T C T C |
| K3 | A T C G G C A C T C G T G C G T T C T C |
| K4 | A T G C G C T C T C G A G C G T T C T C |
| K5 | A T C C G C A C T C G T G C G T T C T C |
| K6 | A T C G G C T C T C G A G C G T T C T C |
| K7 | A T C G G C T C T C G A G C G T T C T C |
| K9 | A   G   C T C G A G C G T T C T C |
| K16 |     T C G T C G T T T T G T C G T T T T G T C G T T |
| K17 |     T C G T C G T T T T G T C G T T T T G T C G T T |
| K18 |     T C G T C G T T T T G T C G T T T T G T C G T T |
| K19 |     T C G T C G T T T T G T C G T T T T G T C G T T |
| K20 |     T C G T C G T T T T G T C G T T T T G T C G T T |
| K21 |     T C G T C G T T T T G T C G T T T T G T C G T T |
| K22 |     T C G T C G T T T T G T C G T T T T G T C G T T |
| K23 |     T C G T C G T T T T G T C G T T T T G T C G T T |
| K31 |     T C G T C G T T T T G T C G T T T T G T C G T T |
| K34 |     T C G T C G T T T T G T C G T T T T G T C G T T |
| K39 |     T G G G G G G G G G T C G T T T T G G G G G T C |
| K40 |     T G G G G G G G G G T C G T T T T G G G G G T C |
| K41 |     T G G G G G G G G G T C G T T T T G G G G G T C |
| K42 |     T G G G G G G G G G A C G A T T T G G G G G T A |
| K43 |     T G G G G G G G G G A C G A T T T G G G G G T A |
| K44 |     T G G G G G G G G G A C G A T T T G G G G G T A |
| K45 |     T G G G G G G G G G A C G A T T T G G G G G T A |
| K46 |     T G G G G G G G G G A C G A T T T G G G G G T A |
| K47 |     T G G G G G G G G G A C G A T T T G G G G G T A |
| K48 | T T G A G G G G G G G A C G A T T T G G G G G T A |
| K49 | T T G A G G G G G G G A C G A T T T G G G G G T A |

Sequence alignment table for positions K50–K80:

| Pos | Row1 | Row2 | Row3 | Row4 | Row5 | Row6 | Row7 | Row8 | Row9 | Row10 | Row11 | Row12 | Row13 |
|-----|------|------|------|------|------|------|------|------|------|-------|-------|-------|-------|
| K50 |      |      |      | A | G | C | T | G | C | A | A | C | T |
| K51 |      |      |      | A | G | T | C | G | C | A | A | C | T |
| K52 |      |      |      | A | G | C | T | G | C | G | A | C | T |
| K53 |      |      |      | A | G | T | C | G | C | G | A | C | T |
| K54 |      |      |      | A | G | T | T | G | C | G | A | C | T |
| K55 |      |      |      | A | G | C | C | G | C | G | G | C | T |
| K56 |      |      |      | A | G | T | C | G | C | A | A | C | T |
| K57 |      |      |      | A | G | C | C | G | C | G | G | C | T |
| K58 |      |      |      | A | G | C | C | G | C | A | G | C | T |
| K59 |      |      |      | A | G | C | C | G | C | G | G | C | T |
| K60 |      |      |      | A | G | C | C | G | C | A | G | C | T |
| K61 |      |      |      | A | G | T | T | G | C | G | T | T | G |
| K62 |      |      |      | G | C | C | G | T | G | C | T | G |   |
| K63 |      |      |      | T | T | T | T | T | G | C | T | G |   |
| K64 |      |      |      | T | A | C | G | T | G | C | T | G |   |
| K65 |      | A    |      | T | G | C | T | T | G | C | T | G |   |
| K66 | C    | T    |      | C | T | C | T | T | G | A | G | G |   |
| K67 | C    | G    | A    | G | A | C | T | A | G | C | G | G |   |
| K68 | C    | G    | T    | T | C | G | T | A | G | C | A | A | C |
| K69 |      |      | G    | A | C | G | T | T | G | A | A | A | G |
| K70 |      |      |      | C | C | G | T | T | G | C | T | C | T |
| K71 |      |      |      | A | A | G | T | T | G | C | G | G | A |
| K72 |      |      |      | C | C | G | T | A | G | A | T | G | C |
| K73 |      |      |      | G | A | G | T | A | G | A | A | T | G |
| K77 |      |      |      | T | G | G | T | T | G | A | C | A | T |
| K78 |      |      |      | A | T | T | T | T | G | A | T | C | A |
| K79 |      |      |      | C | A | A | T | T | G | A | G | G | C |
| K80 |      |      |      |   | C | C | T | T | G | A | T | C |   |

Figure 10B

B) D class ODN

| ID | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| DV17 | | | | | G | G | G | T | G | C | A | C | G | T | T | G | A | C | G | T | T | | | | | | | | | | | | | | |
| DV19 | | | | | G | G | T | G | G | C | A | T | C | C | A | A | A | G | A | A | | | | | | | | | | | | | | |
| dv25 | | | | | G | G | T | G | G | C | A | T | C | C | A | A | A | G | A | A | | | | | | | | | | | | | | |
| DV27 | | | | | G | G | T | G | G | C | A | T | C | C | A | A | A | G | A | A | | | | | | | | | | | | | | |
| DV28 | | | | | G | G | T | G | G | C | A | T | C | C | A | A | A | G | A | A | | | | | | | | | | | | | | |
| DV29 | | | | | G | G | T | G | G | C | A | T | C | C | A | A | A | G | A | A | | | | | | | | | | | | | | |
| DV30 | | | | | G | G | T | G | G | C | A | T | C | C | A | A | A | G | A | A | | | | | | | | | | | | | | |
| DV32 | | | | | G | A | T | G | G | C | A | G | C | C | A | A | T | G | A | A | | | | | | | | | | | | | | |
| DV35 | | | | | G | G | T | G | G | C | A | T | C | C | A | A | A | G | A | A | | | | | | | | | | | | | | |
| DV39 | | | | A | G | G | T | G | G | C | A | T | C | C | A | A | A | G | A | A | | | | | | | | | | | | | | |
| DV51 | | | | | G | G | T | G | G | C | A | T | C | C | A | A | A | G | A | A | | | | | | | | | | | | | | |
| DV52 | | | | | G | G | T | G | G | C | A | T | C | C | A | A | A | G | A | A | | | | | | | | | | | | | | |
| DV53 | | | | | G | G | T | G | G | C | A | T | C | C | A | A | A | G | A | A | | | | | | | | | | | | | | |
| DV54 | | | | | G | | T | G | G | C | A | T | C | C | A | A | A | G | A | A | | | | | | | | | | | | | | |
| DV116 | | | | | | | | | | | | | | | | | | | | | T | G | G | G | G | G | G | A | G | G | G | G | G | G | G |
| DV129 | G | T | G | G | G | C | A | G | G | C | C | C | G | G | G | C | G | G | A | G | G | G | G | G | G | G | A | G | G | G | G | G | G | | |
| DV130 | | G | G | G | | A | G | T | G | G | G | C | G | G | A | G | G | G | G | G | G | G | A | G | G | G | G | G | T | G | T | T | T | | |
| DV131 | | | | | | A | G | T | G | G | G | C | G | G | A | G | G | G | G | G | G | G | A | G | G | G | G | G | C | G | G | G | | | |
| DV132 | | G | G | G | | A | G | T | G | G | G | C | G | G | A | G | G | G | G | G | G | G | A | G | G | G | G | G | T | G | G | G | | | |
| DV133 | | G | G | G | | A | G | T | G | G | G | C | G | G | A | G | G | G | G | G | G | G | A | G | G | G | G | G | A | G | G | G | | | |
| dv134 | | | | | | | | | | | | | | | | | | | | | G | A | A | A | A | A | A | A | A | A | A | A | A | | | |
| DV135 | | | | | | T | C | A | A | A | T | G | C | C | G | G | G | T | T | T | A | C | C | C | C | C | C | C | C | G | C | C | C | A | G | C |
| DV136 | | | | | | | | T | T | T | G | C | G | G | G | G | G | G | G | G | A | C | C | C | C | C | C | C | C | G | G | G | G | A | T | G |
| DV137 | | | | | | | | T | T | T | C | C | A | A | T | C | C | C | C | C | A | C | C | C | C | C | C | C | C | G | A | T | T | C | T | T |
| DV138 | | | | | T | T | T | T | C | G | G | G | G | A | C | C | C | C | C | C | C | C | C | C | G | T | G | G | G | G | T | T | T | T | T | T |
| DV139 | | | | | T | T | T | T | C | G | G | G | G | A | C | C | C | C | C | C | C | C | C | C | G | T | G | G | G | G | T | T | T | T | T | T |
| DV140 | | | | | T | T | T | T | C | G | G | G | G | A | C | C | C | C | C | C | C | C | C | C | G | T | G | G | G | G | T | T | T | T | T | T |
| DV141 | | | | | T | T | T | T | C | G | G | G | G | A | C | C | C | C | C | C | C | C | C | C | G | T | G | G | G | G | T | T | T | T | T | T |

Figure 10C

| | | | | | | | | | | | | | | | | | | | |
|---|---|---|---|---|---|---|---|---|---|---|---|---|---|---|---|---|---|---|---|
| DV142 | | | G | G | T | A | T | A | T | C | G | G | A | A | G | G | G | G | G |
| dv143 | | | G | G | T | G | C | A | T | C | G | T | A | G | G | G | G | G | G |
| dv144 | | | G | A | T | G | C | A | T | G | T | C | A | G | G | G | G | G | G |
| dv145 | | | G | G | T | G | C | A | T | G | G | C | G | G | G | G | G | G | G |
| dv146 | T | C | G | G | C | G | T | T | G | T | c | A | c | T | C | C | T | G | G |
| dv147 | T | C | G | A | C | G | C | T | g | T | g | A | G | g | T | T | C | C | C |
| D148 | | | G | G | T | G | C | A | T | C | G | c | G | G | G | G | G | G | G |
| D149 | | | G | G | G | G | A | T | T | C | T | A | C | G | G | G | G | G | G |
| D149MB | | | G | G | T | C | G | T | T | C | T | C | C | G | G | G | G | G | G |

USE OF STERICALLY STABILIZED CATIONIC LIPOSOMES TO EFFICIENTLY DELIVER CPG OLIGONUCLEOTIDES IN VIVO

CROSS REFERENCE TO RELATED APPLICATIONS

This is the §371 U.S. National Stage of International Application No. PCT/US02/24235, filed Jul. 29, 2002, which was published in English under PCT Article 21(2), which claims priority to U.S. application Ser. No. 10/206,407, filed Jul. 25, 2002 (now abandoned), and claims the benefit of U.S. Provisional Application No. 60/308,283, filed Jul. 27, 2001. Priority to both U.S. application Ser. No. 10/206,407 and U.S. Provisional Application No. 60/308,283 is claimed, and U.S. Provisional Application No. 60/308,283 is incorporated herein by reference.

FIELD

This application relates to the field of oligodeoxynucleotides including a CpG motif, specifically to the use of stabilized cationic liposomes to deliver oligodeoxynucleotides including a CpG motif, and the use of these liposomes to deliver oligodeoxynucleotides including a CpG motif in a variety of clinical applications.

BACKGROUND

Bacterial DNA contains unmethylated "CpG motifs" that strongly stimulate the mammalian immune system. Synthetic oligodeoxynucleotides (ODN) expressing CpG motifs patterned after those found in bacteria trigger cells of the immune system to proliferate, mature, and produce cytokines, chemokines and immnunoglobulin (Ig) Krieg et al., *Nature* 374:546, 1995; Yamamoto et al., *J. Immunol.* 148:407, 1992; Klinman et al., *Proc. Natl. Acad. Sci. USA* 93:2879, 1996; Takeshita et al., *Cell Immunology* 206:101, 2000). These immunostimulatory activities are being harnessed therapeutically. CpG ODN show promise as immune adjuvants, significantly improving the immune response to co-administered antigens (Roman et al., *Nature Medicine* 3:849, 1997; Davis et al., *J. Immunol.* 160:870, 1998; Chu et al., *J. Exp. Med.* 186:1623, 1997; Klinman et al., *Springer Semin Immunopathol* 22:173, 2000; Tighe et al., *J Allergy Clin Immunol* 106:124, 2000). The strong Th1 response elicited by CpG ODN down-regulates Th2 mediated IgE and cytokine production, thereby interfering with allergic asthma (Sur et al., *J. Immunol.* 162:6284, 1999; Broide et al., *J. Immunol.* 161:7054, 1998; Kline et al., *J. Immunol.* 160:2555, 1998). Finally, by pre-activating the innate immune system, CpG ODN can protect naive animals against a variety of microbial and parasitic pathogens (Krieg et al., *J. Immunol.* 161:2428, 1998; Elkins et al., *J. Immunol.* 162:2291, 1999; Klinman, *Antisense awed Nuc Acid Drug Dev* 8:181, 1998; Klinman et al., *Infect Immun* 67:5658, 1999; Klinman et al., *Immunity* 11:123, 1999).

Prolonging the bioavailability and duration of action of CpG ODN may improve their therapeutic efficacy. Unfortunately, phosphorothioate CpG ODN used in vivo are rapidly eliminated from the circulation due to adsorption onto serum proteins and degradation by serum nucleases (Litzinger et al., *Biochim. Biophys. Acta* 1281:139, 1996; Soni et al., *Hepatology* 28:1402, 1998; Gregoriadis, *Pharm. Res* 15:661, 1998). One potential method for protecting CpG ODN from degradation while increasing their uptake by cells of the immune system involves liposome encapsulation (MacDonald et al., *Biochim. Biophys. Acta* 1061:297, 1991; Takeshita et al., *Eur. J. Immunol.* 30:108, 2000).

SUMMARY

As disclosed herein, sterically stabilized cationic liposomes (SSCL) encapsulating a K type oligodeoxynucleotide (ODN) including a CpG motif can be used to effectively deliver the ODN to a cell. A novel method is disclosed for producing SSCL that encapsulate the K type ODN. When combined with other targeted biological agents, such as a chimeric molecule comprising a targeting molecule selected from the group consisting of an IL-13, and an anti-IL-13 receptor antibody; and an effector molecule selected from the group consisting of a *Pseudomonas* exotoxin, a Diphtheria toxin, a chemotherapeutic agent, and a radionucleotide, the SSCL encapsulating a K type ODN act synergistically to dramatically reduce the growth of solid tumors.

A sterically stabilized cationic liposome (SSCL) composition is disclosed herein that includes a cationic lipid, a co-lipid, and a stabilizing agent. The SSCL encapsulates an oligodeoxynucleotide of at least ten nucleotides in length comprising a CpG motif, wherein the oligodeoxynucleotide comprising a CpG motif comprises a sequence represented by the formula 5' $N_1N_2N_3$Q-CpG-WN$_4$N$_5$N$_6$ 3' (SEQ ID NO: 97), wherein Q is a T, G, or A, W is A or T, and $N_1$, $N_2$, $N_3$, $N_4$, $N_5$, and $N_6$ are any nucleotide, and wherein the lipid:co-lipid ratio is from about 3:7 to about 7:3, and wherein stabilizing agent comprises about 1 percent to about 5 percent of the co-lipid composition. Methods for using these SSCL encapsulating a K type ODN to stimulate a cell of the immune system are also disclosed.

In one embodiment, a method is disclosed for inducing an immune response in a subject. The method includes contacting immune cells in vitro with a sterically stabilized cationic liposome encapsulating an oligodeoxynucleotide of at least ten nucleotides in length comprising a CpG motif, wherein the oligodeoxynucleotide comprising a CpG motif comprises a sequence represented by the formula 5' $N_1N_2N_3$Q-CpG-WN$_4$N$_5$N$_6$ 3' (SEQ ID NO: 97), wherein Q is a T, G, or A, W is A or T, and $N_1$, $N_2$, $N_3$, $N_4$, $N_5$, and $N_6$ are any nucleotide; and contacting the immune cells with an antigen for a time sufficient to generate antigen specific immune cells. These antigen specific immune cells are administered to the subject in an amount sufficient to induce an immune response.

In another embodiment, a method is disclosed for producing a SSCL encapsulating an agent of interest. The method includes contacting a unilamellar vesicle with an agent of interest, dehydrating the unilamellar vesicle and the agent of interest; and rehydrating the unilamellar vesicle and the agent of interest to produce the sterically stabilized cationic liposome encapsulating the agent of interest. In one embodiment, the agent of interest is a K type ODN.

In a further embodiment, a method is disclosed for impairing growth of a solid tumor cell bearing an IL-13 receptor in a subject. The method includes administering to the subject a therapeutically effective amount of a recombinant chimeric molecule comprising a targeting molecule selected from the group consisting of an IL-13, and an anti-IL-13 receptor antibody; and an effector molecule selected from the group consisting of a *Pseudomonas* exotoxin, a Diphtheria toxin, a chemotherapeutic agent and a radionucleotide, wherein the effector molecule is genetically fused or covalently linked to the targeting molecule or is linked to the targeting molecule by a linker. The method also includes administering to the subject a therapeutically effective amount of an SSCL encapsulating a K type ODN.

The foregoing and other features and advantages will become more apparent from the following detailed description of several embodiments, which proceeds with reference to the accompanying figures.

BRIEF DESCRIPTION OF THE DRAWINGS

FIG. 6: is a table (Table I) of data on the efficiency of ODN encapsulation by different types of liposomes.

FIG. 7 is a table (Table II) of data demonstrating CSL encapsulation enhances CpG uptake in vivo.

FIG. 8 is a table (Table III) demonstrating liposome encapsulated CpG ODN enhances cytokine production in vivo.

FIG. 9 is a table (Table IV) of data demonstrating of the co-encapsulation of ova plus CpG ODN in SSCL improves immunogenicity.

FIG. 10 is a table (Table V) showing the sequence of CpG ODN. FIGS. 10A and 10B are K class ODN sequences. FIGS. 10C and 10D are D class ODN sequences. K1 is SEQ ID NO: 3, K2 is SEQ ID NO: 4, K3 is SEQ ID NO: 5, K4 is SEQ ID NO: 6, K5 is SEQ ID NO: 7, K6 is SEQ ID NO: 8, K7 is SEQ ID NO: 9, K9 is SEQ ID NO: 10, K16 is SEQ ID NO: 11, K17 is SEQ ID NO: 12, K18 is SEQ ID NO: 13, K19 is SEQ ID NO: 14, K20 is SEQ ID NO: 15, K21 is SEQ ID NO: 16, K22 is SEQ ID NO: 17, K23 is SEQ ID NO: 18, K31 is SEQ ID NO: 19, K34 is SEQ ID NO: 20, K39 is SEQ ID NO: 21, K40 is SEQ ID NO: 22, K41 is SEQ ID NO: 23, K42 is SEQ ID NO: 24, K43 is SEQ ID NO: 25, K44 is SEQ ID NO: 26, K45 is SEQ ID NO: 27, K46 is SEQ ID NO: 28, K47 is SEQ ID NO: 29, K48 is SEQ ID NO: 30, K49 is SEQ ID NO: 31, K50 is SEQ ID NO: 32, K51 is SEQ ID NO: 33, K52 is SEQ ID NO: 34, K53 is SEQ ID NO: 35, K54 is SEQ ID NO: 36, K55 is SEQ ID NO: 37, K56 is SEQ ID NO: 38, K57 is SEQ ID NO: 39, K58 is SEQ ID NO: 40, K59 is SEQ ID NO: 41, K60 is SEQ ID NO: 42, K61 is SEQ ID NO: 43, K62 is SEQ ID NO: 44, K63 is SEQ ID NO: 45, K64 is SEQ ID NO: 46, K65 is SEQ ID NO: 47, K66 is SEQ ID NO: 48, K67 is SEQ ID NO: 49, K68 is SEQ ID NO: 50, K69 is SEQ ID NO: 51, K70 is SEQ ID NO: 52, K71 is SEQ ID NO: 53, K72 is SEQ ID NO: 54, K73 is SEQ ID NO: 55, K77 is SEQ ID NO: 56, K78 is SEQ ID NO: 57, K79 is SEQ ID NO: 58, K80 is SEQ ID NO: 59, DV17 is SEQ ID NO: 60, DV19 is SEQ ID NO: 61, DV25 is SEQ ID NO: 62, DV27 is SEQ ID NO: 63, DV28 is SEQ ID NO: 64, DV29 is SEQ ID NO: 65, DV30 is SEQ ID NO: 66, DV32 is SEQ ID NO: 67, DV35 is SEQ ID NO: 68, DV39 is SEQ ID NO: 69, DV51 is SEQ ID NO: 70, DV52 is SEQ ID NO: 71, DV53 is SEQ ID NO: 72, DV54 is SEQ ID NO: 73, DV116 is SEQ ID NO: 74, DV129 is SEQ ID NO: 75, DV130 is SEQ ID NO: 76, DV131 is SEQ ID NO: 77, DV132 is SEQ ID NO: 78, DV133 is SEQ ID NO: 79, DV134 is SEQ ID NO: 80, DV135 is SEQ ID NO: 81, DV136 is SEQ ID NO: 82, DV137 is SEQ ID NO: 83, DV138 is SEQ ID NO: 84, DV139 is SEQ ID NO: 85, DV140 is SEQ ID NO: 86, DV141 is SEQ ID NO: 87, DV142 is SEQ ID NO: 88, DV143 is SEQ ID NO: 89, DV144 is SEQ ID NO: 90, DV145 is SEQ ID NO: 91, DV146 is SEQ ID NO: 92, DV147 is SEQ ID NO: 93, D148 is SEQ ID NO: 94, D149 is SEQ ID NO: 95, D149MB is SEQ ID NO: 96.

FIG. 11 is a set of graphs and digital images showing the anti-tumor activity of recombinant IL-13-*Pseudomonas* exotoxin (IL13-PE) and (CpG ODN)$_{SSCL}$ The anti-tumor activity of IL13-PE and (CpG ODN)$_{SSCL}$ was examined in nude mice (4-6/group) transplanted with human squamous cell carcinoma cells (KCCT 873). Treatments of mice with IL13-PE, (CpG ODN)$_{SSCL}$, non (CpG ODN)$_{SSCL}$ or the combination at day 4, 6 and 8 are as indicated. FIG. 11a is a comparison of the anti-tumor effects of IL13-PE (50 μg/kg), (CpG ODN)$_{SSCL}$ (50 μg), non (CpG ODN)$_{SSCL}$ or the combination.

FIG. 12 is a set of graphs showing the cytotoxic activity of NK cells from mice treated with IL13-PE plus (CpG ODN)$_{SCCL}$.

SEQUENCE LISTING

Figure 1:
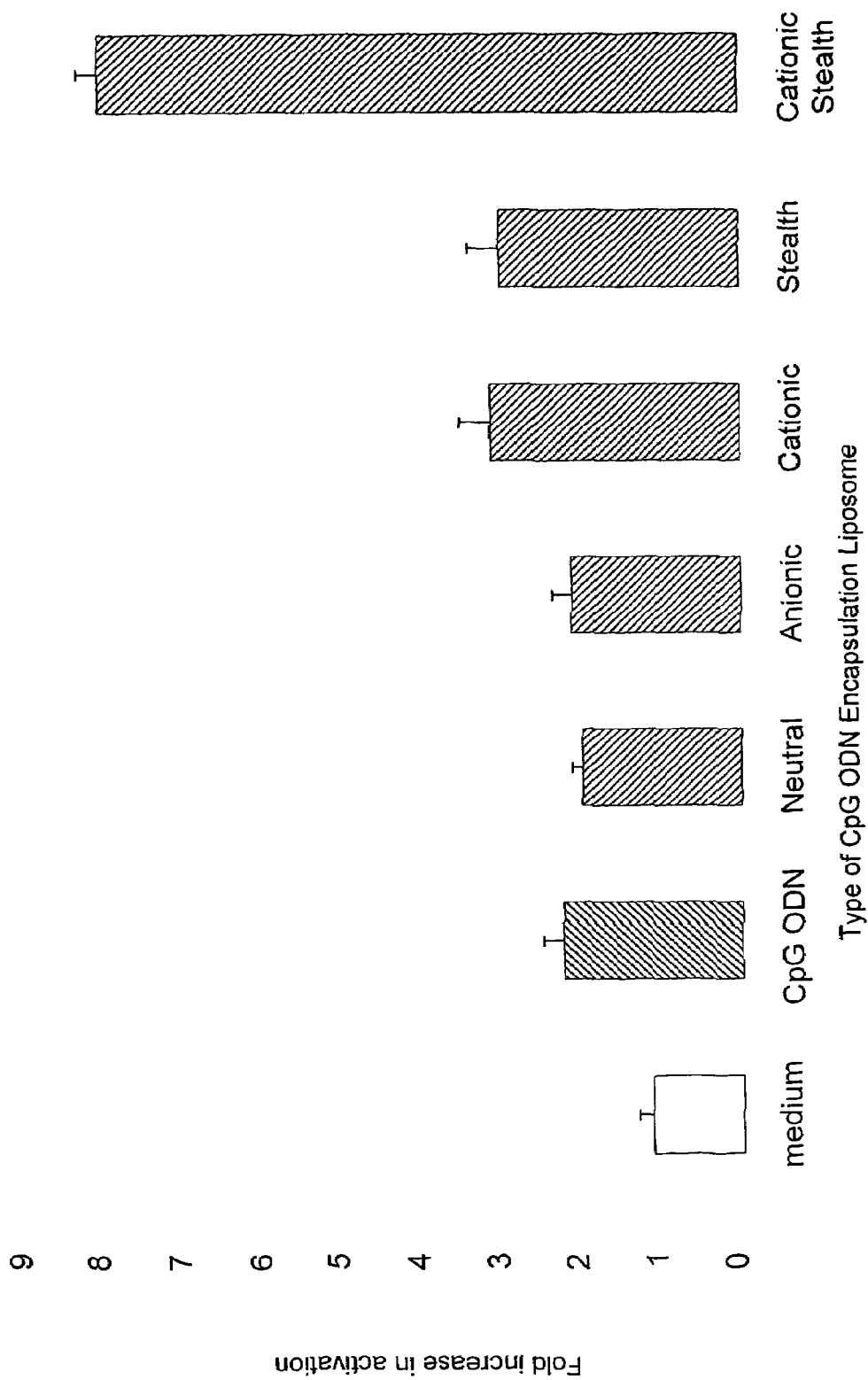
FIG. 1 is a bar graph demonstrating that IL-12 p40 expression is induced by CpG ODN encapsulated liposomes. RAW 264.7 cells were transfected with an IL-12 promoter-luciferase gene vector (pGL3 basic vector). $10^6$ transfected cells were stimulated for 24 hours with 0.5 μM of free or liposome encapsulated CpG ODN, and monitored for luciferase activity. Data show the fold increase in luciferase activity at 24 hours compared to medium alone, and represent the mean +SD of 3 independent experiments. * $p<0.01$ when compared to free CpG ODN.

The nucleic and amino acid sequences listed in the sequence listing are shown using standard letter abbreviations for nucleotide bases, and three letter code for amino acids, as defined in 37 C.F.R. 1.822.

DETAILED DESCRIPTION

I. Abbreviations
CHOL: cholesterol
CpG ODN: an oligodeoxynucleotide (either a D or a K type) including a CpG motif.
DC-CHOL: Dimethyaminoethane-carbamol-cholesterol
DOPE: Dioleoylphosphatidylethanolamine
IL: interleukin
IL13-PE: recombinant IL-13-*Pseudomonas* exotoxin
PEG: polyethylene glycol;
PEG-PE: polyethylene glycol derivatized phosphatidylethanolamine
Nm: nanometers
SSCL: sterically stabilized cationic liposome
SSCL-CpG ODN or (CpG ODN)$_{SCCL}$: sterically stabilized cationic liposome encapsulated K type CpG ODN
µM: micromolar II. Terms
Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments disclosed herein, the following explanations of specific terms are provided:

Allergen: A substance that can induce an allergic or asthmatic response in a susceptible subject. The list of allergens is enormous and can include pollens, insect venoms, animal dander dust, fungal spores and drugs (e.g. penicillin). Examples of natural, animal and plant allergens include proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia*); *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides*, *Juniperus virginiana*, *Juniperus communis* and *Juniperis ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus intermis*). The term "allergy" refers to acquired hypersensitivity to a substance (allergen). An "allergic reaction" is the response of an immune system to an allergen in a subject allergic to the allergen. Allergic conditions include eczema, allergic rhinitis or coryza, hay fever, bronchial asthma, urticaria (hives) and food allergies, and other atopic conditions.

Amphiphilic cationic lipid: Any amphiphilic lipid, including synthetic lipids and lipid analogs, having hydrophobic and polar head group moieties, a net positive charge, and which by itself can form spontaneously into bilayer vesicles or micelles in water, as exemplified by phospholipids. The term also includes any amphiphilic lipid that is stably incorporated into lipid bilayers in combination with phospholipids with its hydrophobic moiety in contact with the interior, hydrophobic region of the bilayer membrane, and its polar head group moiety oriented toward the exterior, polar surface of the membrane.

Antibody: A protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to be a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" includes both intact immunoglobulins as well as fragments produced by digestion with various peptidases. In one specific, non-limiting example, pepsin digests an antibody below the disulfide linkages in the hinge region to produce F(ab)'$_2$, a dimer of Fab' which itself is a light chain joined to $V_H$-$C_{H1}$ by a disulfide bond. The F(ab)'$_2$ may be reduced under mild conditions to break the disulfide linkage in the hinge region thereby converting the dimer into a Fab' monomer. The Fab' monomer is essentially a Fab with part of the hinge region (see Fundamental Immunology, W. E. Paul, ed., Raven Press, N.Y. (1993) for more antibody fragment terminology). While the Fab' fragment is defined in terms of the digestion of an intact antibody, one of skill will appreciate that such Fab' fragments may be synthesized de novo either chemically or by utilizing recombinant DNA methodology.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Anti-infectious agent: A substance (such as a chemical compound, protein, antisense oligonucleotide, or other molecule) of use in treating infection of a subject. Anti-infectious agents include, but are not limited to, anti-fungals, anti-virals, and antibiotics. These agents can be administered in conjunction (simultaneously or sequentially) with SSCL encapsulated K type CpG ODN.

Animal: Living multi-cellular vertebrate organisms, a category that includes, for example, mammals and birds. The term mammal includes both human and non-human mammals. Similarly, the term "subject" includes both human and veterinary subjects.

Asthma: A disorder of the respiratory system characterized by inflammation, narrowing of the airways and increased reactivity of the airways to inhaled agents. Asthma is frequently, although not exclusively associated with atopic or allergic symptoms.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer a significant part of the activity to the CpG oligodeoxynucleotide. A CpG oligodeoxynucleotide is an oligodeoxynucleotide that is at least about ten nucleotides in length and includes an unmethylated CpG. CpG oligodeoxynucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cancer: A malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived. Cancer includes, but is not limited to, solid tumors.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy,* Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Cytokine: Proteins made by cells that affect the behavior of other cells, such as lymphocytes. In one embodiment, a cytokine is a chemokine, a molecule that affects cellular trafficking. Specific non-limiting examples of cytokines are IFNγ, IL-6, and IL-10.

D Type Oligodeoxynucleotide (D ODN): An oligodeoxynucleotide including an unmethylated CpG motif that has a sequence represented by the formula:

5' RY-CpG-RY 3' wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D type ODN is at least about 16 nucleotides in length and includes a sequence represented by Formula III:

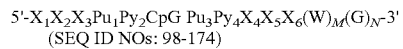

5'-$X_1X_2X_3Pu_1Py_2CpG\ Pu_3Py_4X_4X_5X_6(W)_M(G)_N$-3'
(SEQ ID NOs: 98-174)

wherein the central CpG motif is unmethylated, Pu is a purine nucleotide, Py is a pyrimidine nucleotide, X and W are any nucleotide, M is any integer from 0 to 10, and N is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular response. For example, D ODNs stimulate natural killer cells and the maturation of dendritic cells.

Figure 14:
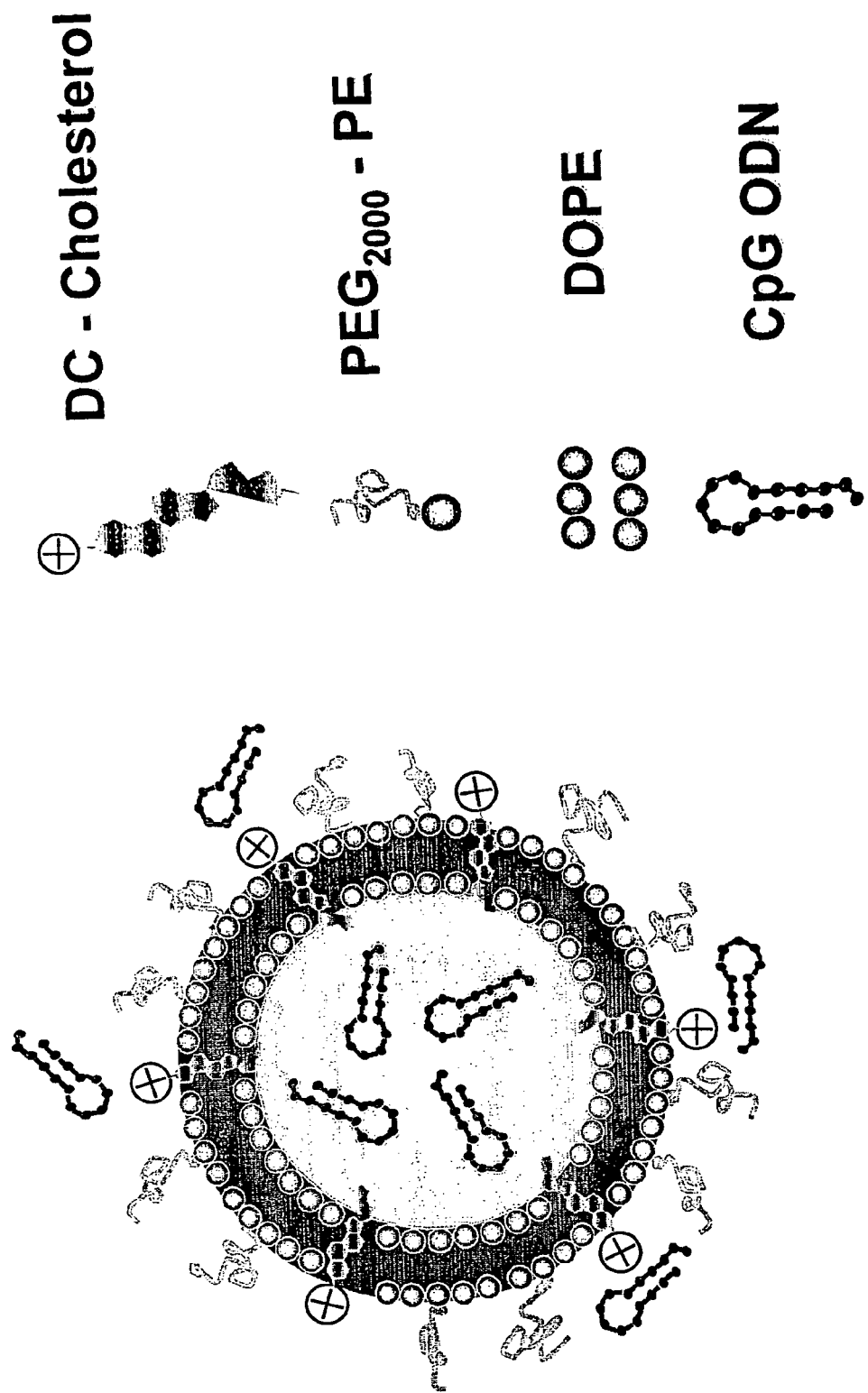
FIG. 14 is a schematic diagram of the generation of SSCL by the dehydration/rehydration method disclosed herein. As shown in the diagram the CpG ODN an encapsulated (interior) in the SSCL.

Encapsulated: To be included (in the interior of) a liposome. An exemplary diagram of CpG ODN encapsulated in a SSCL is shown in FIG. 14.

Epitope: An antigenic determinant. These are particular chemical groups or peptide sequences on a molecule that are antigenic, i.e. that elicit a specific immune response. An antibody binds a particular antigenic epitope.

Functionally Equivalent: Sequence alterations, for example in a K type ODN that yield the same results as described herein. Such sequence alterations can include, but are not limited to, deletions, base modifications, mutations, labeling, and insertions.

Growth Factor: A protein or polypeptide ligand that activates or stimulates cell division or differentiation or stimulates biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor beta (TGF-β), fibroblast growth factors (FGF), interleukin 2 (IL-2), nerve growth factor (NGF), interleukin 3 (IL-3), interleukin 4 (IL4), interleukin 1 (IL-1), interleukin 6 (IL-6), interleukin 7 (IL-7), granulocyte/macrophage colony-stimulating factor (GM-CSF), granulocyte colony-stimulating factor (G-CSF), macrophage colony-stimulating factor (M-CSF), erythropoietin, interleukin 13 receptor (IL-13R), amongst others. It should be noted that some cytokines act as growth factors.

Hydrophilic polymer: Long chain highly hydrated flexible neutral polymers attached to lipid molecules. Examples include, but are not limited to polyethylene glycol (PEG), polyethylene glycol derivatized with phosphatidyl ethanolamine (PEG-PE), polyethylene glycol derivatized with tween, polyethylene glycol derivatized with distearoylphosphatidylethanolamine (PEG-DSPE), ganglioside $G_{M1}$ and synthetic polymers. Such polymers typically have a molecular weight in the range of 1000-10,000. Preferably, the molecular weight for PEG is approximately 2000.

Immune response: A response of a cell of the immune system, such as a B cell, T cell to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFNγ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. One, specific, non-limiting example of a statistical test used to assess a substantial increase is the use of a Z test to compare the percent of samples that respond to SSCL encapsulating a K type CpG ODN as compared to the percent of samples that respond using the CpG alone (unencapsulated). A non-paramentric ANOVA can be used to compare differences in the magnitude of the response induced by SSCl encapsulating a K type CpG ODN as compared to the percent of samples that respond using the CpG ODN alone. In this example, p≦0.05 is significant, and indicates a substantial increase in the parameter of the immune response. One of skill in the art can readily identify other statistical assays of use.

Immune system deficiency: A disease or disorder in which the subject's immune system is not functioning in normal capacity or in which it would be useful to boost a subject's immune response. Immune system deficiencies include those diseases or disorders in which the immune system is not functioning at normal capacity, or in which it would be useful to boost the immune system response. In one specific, non-limiting example, a subject with an immune system deficiency has a tumor or cancer (e.g. tumors of the brain, lung (e.g. small cell and non-small cell), ovary, breast, prostate, colon, as well as other carcinomas and sarcomas).

Immunoliposome and immunolipid:nucleic acid complex: A liposome or lipid:nucleic acid complex bearing an antibody or antibody fragment that acts as a targeting moiety enabling the lipid:nucleic acid complex to specifically bind to a particular "target" molecule that may exist in solution or may be bound to the surface of a cell. Where the target molecule is one that is typically found in relative excess (e.g., >=10-fold) and in association with a particular cell type or alternatively in a multiplicity of cell types all expressing a particular physiological condition the target molecule is said to be a "characteristic marker" of that cell type or that physiological condition. Thus, for example, a cancer may be characterized by the overexpression of a particular marker such as the HER2 (c-erbB-2/neu) proto-oncogene in the case of breast cancer, or the IL-13 receptor in the case of head and neck carcinoma.

Infectious agent: An agent that can infect a subject, including, but not limited to, viruses, bacteria, and fungi. Many of these infectious agents are pathogenic, in that they cause disease in an infected host.

Examples of infectious virus include: *Retroviridae; Picornaviridae* (for example, polio viruses, hepatitis A virus; enteroviruses, human coxsackie viruses, rhinoviruses, echoviruses); *Calciviridae* (such as strains that cause gastroenteritis); *Togaviridae* (for example, equine encephalitis viruses, rubella viruses); *Flaviridae* (for example, dengue viruses, encephalitis viruses, yellow fever viruses); *Coronaviridae* (for example, coronaviruses); *Rhabdoviridae* (for example, vesicular stomatitis viruses, rabies viruses); *Filoviridae* (for example, ebola viruses); *Paranyxoviridae* (for example, parainfluenza viruses, mumps virus, measles virus, respiratory syncytial virus); *Orthomyxoviridae* (for example, influenza viruses); *Bungaviridae* (for example, Hantaan viruses, bunga viruses, phleboviruses and Nairo viruses); *Arena viridae* (hemorrhagic fever viruses); *Reoviridae* (e.g., reoviruses, orbiviurses and rotaviruses); *Birnaviridae; Hepadnaviridae* (Hepatitis B virus); *Parvoviridae* (parvoviruses); *Papovaviridae* (papilloma viruses, polyoma viruses); *Adenioviridae* (most adenoviruses); *Herpesviridae* (herpes simplex virus (HSV) 1 and HSV-2, varicella zoster virus, cytomegalovirus (CMV), herpes viruses); *Poxviridae* (variola viruses, vaccinia viruses, pox viruses); and *Iridoviridae* (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (such as *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps), *Streptococcus pneumoniae,* pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira,* and *Actinomyces israelli.*

Examples of infectious fungi include, but are not limited to, *Cryptococcus neoformans, Histoplasma capsulatum, Coccidioides immitis, Blastomyces dermatitidis, Chlamydia trachomatis, Candida albicans.*

Other infectious organisms (such as protists) include: *Plasmodium falciparum* and *Toxoplasma gondii.*

Interferon gamma: IFNγ is a dimeric protein with subunits of 146 amino acids. The protein is glycosylated at two sites, and the pI is 8.3-8.5. IFNγ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFNγ with respect to molecular mass and charge are due to variable glycosylation patterns. 40-60 kDa forms observed under non-denaturing conditions are dimers and tetramers of IFNγ. The human gene has a length of approximately 6 kb. It contains four exons and maps to chromosome 12q24.1.

IFNγ can be detected by sensitive immunoassays, such as an ELSA test that allows detection of individual cells producing IFNγ. Minute amounts of IFNγ can be detected indirectly by measuring IFN-induced proteins such as Mx protein. The induction of the synthesis of IP-10 has been used also to measure IFNγ concentrations. In addition, bioassays can be used to detect IFNγ, such as an assay that employs induction of indoleamine 2,3-dioxygenase activity in 2D9 cells.

Interleukin-6: IL-6 is a cytokine that is 185 amino acids in length. This polypeptide is glycosylated at positions 73 and 172, and is synthesized as a precursor protein of 212 amino acids. Monocytes express at least five different molecular forms of IL-6 with molecular masses of 21.5-28 kDa. They mainly differ by post-translational alterations such as glycosylation and phosphorylation. IL-6 isolated from various cell types shows some microheterogeneity in its N-terminus.

The human IL-6 gene has a length of approximately 5 kb and contains five exons. It maps to human chromosome 7p21-p14 between the markers D7S135 and D7S370. The murine gene maps to chromosome 5. Human IL6 is biologically active in monkeys, rats, and mice.

IL-6 has a myriad of activities and has been demonstrated to influence antigen-specific immune responses and inflammatory reactions. It is one of the major physiological mediators of an acute immune response.

Interleukin-13 (IL-13): A pleiotropic cytokine that is recognized to share many of the properties of IL-4. IL-13 has approximately 30% sequence identity with IL-4 and exhibits IL-4-like activities on monocytes/macrophages and human B cells (Minty et al., *Nature* 362:248, 1993; McKenzie et al., *Proc. Natl. Acad. Sci. USA* 90:3735, 1987). In particular, IL-1 3 appears to be a potent regulator of inflammatory and immune responses. Like IL-4, IL-13 can up-regulate the monocyte/macrophage expression of CD23 and MHC class I and class II antigens, down-regulate the expression of Fcγ, and inhibit antibody-dependent cytotoxicity. IL-13 can also inhibit nitric oxide production as well as the expression of pro-inflammatory cytokines (e.g. IL-1, IL-6, IL-8, IL-10 and IL-12) and chemokines (MIP-1, MCP), but enhance the production of IL-1ra (for example see Zurawski et al., *Immunol. Today* 15:19, 1994; de Wall Malefyt et al., *J. Immunol.* 150: 180A, 1993; de Wall Malefyt et al., *J. Immunol.* 151:6370, 1993; Doherty et al., *J. Immunol.* 151:7151, 1993; and Minty et al., *Eur. Cytokine New.* 4:99, 1993).

Recombinant IL-13 is commercially available from a number of sources (see, e.g. R & D Systems, Minneapolis, Minn., U.S.A., and Sanoff Bio-Industries, Inc., Tervose, Pa., U.S.A.). Alternatively, a gene or a cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, for example, Minty et al., 1993, supra and McKenzie, 1987, supra).

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

5' $N_1N_2N_3Q$-CpG-$WN_4N_5N_6$ 3' (SEQ ID NO: 97)

wherein the central CpG motif is unmethylated, Q is T, G or A, W is A or T, and $N_1$, $N_2$, $N_3$, $N_4$, $N_5$, and $N_6$ are any nucleotides. In one embodiment, Q is a T. Additional detailed description of K ODN sequences and their activities can be found in the description below. Generally K ODNs can stimulate a humoral response. For example, K ODNs stimulate the production of immunoglobulins, such as IgM and IgG. K ODNs can also stimulate proliferation of peripheral blood mononuclear cells and increase expression of IL-6 and/or IL-12, amongst other activities.

Leukocyte: Cells in the blood, also termed "white cells," that are involved in defending the body against infective organisms and foreign substances. Leukocytes are produced in the bone marrow. There are five main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Lipid:nucleic acid complex: The product made by mixing amphiphilic cationic lipids or liposomes with a nucleic acid. The term "CLDC," stands for "cationic lipid:DNA complex" is a convenient abbreviation for lipid:nucleic acid complex. The lipid:nucleic acid complex can also include a "helper lipid." The helper lipid is often a neutral lipid such as DOPE or cholesterol. The lipid:nucleic acid complex may also contain other compounds such as a polycation that are in contact with the nucleic acid of the complex, producing condensed nucleic acid, and hydrophilic polymers such as PEG and derivatized PEG. Derivatized forms of PEG are known to one of skill in the art, and include, but are not limited to, polyethylene glycol$_{2000}$-posphatidylethanolamine.

Mammal: This term includes both human and non-human mammals. Similarly, the term "subject" includes both human and veterinary subjects.

Maturation: The process in which an immature cell, such as dendritic cell, changes in form or function to become a functional mature cell, such as an APC.

Neoplasm: An abnormal cellular proliferation, which includes benign and malignant tumors, as well as other proliferative disorders.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxynucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phophonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligodeoxynucleotide," "immunostimulatory CpG containing oligodeoxynucleotide," "CpG ODN," refers to an oligodeoxynucleotide, which contains a cytosine, guanine dinucleotide sequence and (e.g. has a mitogenic effect or induces cytokine production) vertebrate immune cells. In one embodiment, an immunostimulatory CpG ODN stimulates a parameter of an immune response in a subject. The cytosine, guanine is unmethylated.

An "oligonucleotide delivery complex" is an oligonucleotide associated with (e.g. ionically or covalently bound to; or encapsulated within) a targeting agent (e.g. a molecule that results in a higher affinity binding to a target cell (e.g. B-cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167:3324, 2001).

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in the methods and compositions disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such a proliferative disorder, such as a cancer. An example of a person with a known predisposition is someone with a history of breast cancer in the family, or who has been exposed to factors that predispose the subject to a condition, such as melanoma. "Treatment" refers to a therapeutic intervention that ameliorates a sign or symptom of a disease or pathological condition after it has begun to develop. In one embodiment, treatment refers to a reduction in size of a tumor.

Purified: The term purified does not require absolute purity; rather, it is intended as a relative term. Thus, for example, a purified peptide preparation is one in which the peptide or protein is more enriched than the peptide or protein is in its natural environment within a cell. Preferably, in a purified preparation, the protein or peptide represents at least 50% of the total peptide or protein content of the preparation. Similarly, in a purified preparation of oligodeoxynucleotides, the oligodeoxynucleotide represents at least 50% of the total nucleic acid content of the preparation.

Self-complementary nucleic acid sequence: A nucleic acid sequence that can form Watson-Crick base pairs. The four bases characteristic of deoxyribonucleic acid unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that could form hydrogen bonds with 3, 4, 5, 6 or more bases, respectively, of the same nucleic acid sequence.

Specific binding: Binding which occurs between such paired species as enzyme/substrate, receptor/agonist, receptor/ligand, antibody/antigen, and lectin/carbohydrate which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two that produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

Targeting Molecule: A moiety capable of specifically binding to a particular target molecule and forming a bound complex as described above. Thus the ligand and its corresponding target molecule form a "specific binding pair." Examples of targeting molecules include, but are not limited to antibodies, lymphokines, cytokines, receptor proteins such as CD4 and CD8, solubilized receptor proteins such as soluble CD4, hormones, growth factors, ligands for a specific receptor, and the like which specifically bind desired target cells. In one embodiment the targeting molecule is an antibody or an antibody fragment (e.g., the Fab' fragment). In another embodiment, a targeting molecule is a ligand, such as a cytokine that specifically binds a cytokine receptor.

Sterically Stabilized Cationic Liposome (SSCL): A liposome that includes a cationic lipid, a colipid, and a stabilizing additive. In one embodiment, an SSCL includes DC-CHOL, DOPE, and PE-PEG. In one specific, non-limiting example, an SSCL includes DC-CHOL, DOPE and PE-PEG at a molar ratio of about 4:6:0.06 (see below).

Therapeutically effective dose: A dose sufficient to prevent advancement, or to cause regression of a disease, or which is capable of relieving symptoms caused by a disease, such as pain or swelling.

Vaccine: A preparation of attenuated microorganisms (including but not limited to bacteria and viruses), living microorganisms, antigen, or killed microorganisms, administered for the prevention, amelioration or treatment of infectious disease.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

K Type ODNs and Encapsulation in Sterically Stabilized Cationic Liposomes (SSCL)

An SSCL encapsulating a oligodeoxynucleotide (ODN) composition is disclosed herein. The ODN is about 10 nucleotides in length and includes an unmethylated CpG motif. In one embodiment, the oligodeoxynucleotide includes multiple CpG motifs. Specifically, the ODNs compositions disclosed herein are K type ODNs. K ODNs which exhibit the greatest immunostimulatory activity share specific characteristics. These characteristics differ from those of D ODN (Verthelyi et al., *J. Immunol.* 166:2372-2377, 2001, which is herein incorporated by reference). In addition, K ODN have specific effects on the cells of the immune system, which differ from the effects of D ODN. For example, K ODN stimulate production of IgM. It should be noted that K ODN also stimulate production of cytokines, such as interferon gamma (IFNγ), and stimulate the proliferation of B cells.

The K ODNs are at least about 10 nucleotides in length and include a sequence represented by Formula I:

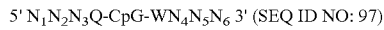

5' $N_1N_2N_3Q$-CpG-$WN_4N_5N_6$ 3' (SEQ ID NO: 97)

wherein the central CpG motif is unmethylated, Q is T, G or A, W is A or T, and $N_1$, $N_2$, $N_3$, $N_4$, $N_5$, and $N_6$ are any nucleotides.

These Formula I or K ODN can stimulate B cell proliferation and the secretion of IgM and IL-6, and processes involved in the body's humoral immunity, such as the production of antibodies against foreign antigens. In one embodiment, the K ODNs induce a humoral immune response.

In one embodiment, K type oligodeoxynucleotides include a sequence represented by the formula

5' $N_1N_2N_3T$-CpG-$WN_4N_5N_6$ 3' (SEQ ID NO: 175).

In another embodiment, K type oligodeoxynucleotides include a phosphate backbone modification. In one specific, non-limiting example, the phosphate backbone modification is a phosphorothioate backbone modification (i.e., one of the non-bridging oxygens is replaced with sulfur, as set forth in International Patent Application WO 95/26204, herein incorporated by reference). In one embodiment, K ODNs have a phophorothioate backbone, and at least one unmethylated CpG dinucleotide. Eliminating the CpG dinucleotide motif from the K ODN significantly reduces immune activation. Incorporating multiple CpGs in a single K ODN can increase immune stimulation. In one embodiment, the K ODN are at least 12 bases long. In addition, K ODN containing CpG motifs at the 5' end are the most stimulatory, although at least one base upstream of the CpG is required. More particularly, the most active K ODNs contain a thymidine immediately 5' from the CpG dinucleotide, and a TpT or a TpA in a position 3' from the CpG motif. Modifications which are greater than 2 base pairs from the CpG dinucleotide motif appear to have little effect on K ODN activity.

K-type CpG ODNs can include modified nucleotides. Any suitable modification can be used to render the ODN resistant to in vivo degradation resulting from, e.g., exo or endonuclease digestion. In one embodiment, the modification includes a phosphorothioate modification. The phosphorothioate modifications can occur at either termini, e.g., the last two or three 5' and/or 3' nucleotides can be linked with phosphorodiester bonds. The ODN also can be modified to contain a secondary structure (e.g., stem loop structure) such that it is resistant to degradation. Another modification that renders the ODN less susceptible to degradation is the inclusion of nontraditional bases such as inosine and quesine, as well as acetyl-, thio- and similarly modified forms of adenine, cytidine, guanine, thymidine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), peptide nucleic acids, phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The oligodeoxynucleotides can be synthesized de novo using any of a number of procedures well known in the art. For example, the oligodeoxynucleotides can be synthesized as set forth in U.S. Pat. No. 6,194,388, which is herein incorporated by reference in its entirety. A K type oligodeoxynucleotide including a CpG motif can be synthesized using, for example, the B-cyanoethyl phophoranidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis. These K type CpG ODNs can be synthesized to include phosphodiester (PO), phosphorothioate (PS) or mixed backbone (i.e. PO-PS, PS-PO, or PS-PO-PS) and peptide nucleic acid (PNA), and their mixed backbones.

The present disclosure relates to encapsulation of CpG ODNs including, but not limited to, the specific sequences shown in Table V (FIGS. 10A-D). As disclosed herein, sterically stabilized cationic liposomes (SSCL) compositions efficiently incorporate and deliver K type CpG ODNs (see FIG. 14) to cells in vitro and in vivo. The SSCLs are liposomes that include a cationic lipid, a colipid, and a stabilizing additive, as described below.

Cationic lipids include, but are not limited to spermidine-cholesterol, spermine-cholesterol, is dimethylaminoethae-carbomol-chlesteroc (DC-CHOL), and dioctadecylamidoglycylspermine (DOGS. In one embodiment, the cationic lipid is dimethylaminoethane-carbomol-cholesterol (DC-CHOL). Colipids include, but are not limited to, neurtal, zwitterionic, and anionic lipids. In one embodiment, the colipid is dioleoylphosphatidylethanolamine (DOPE). The colipid can be a moiety that allows the stabilizing additive (see below) to be incorporated into the complex. Without being bound by theory, derivatization of the lipid with an additive allows the moiety to anchor the stabilizing additive to the cationic lipid complex. The colipid can be conjugated to additives which prevent aggregation and precipitation of cationic lipid-nucleic acid complexes. Colipids which may be used to incorporate such additives to compositions disclosed herein include, but are not limited to, zwitterionic or other phospholipids. Preferably, the colipid is inert and biocompatible.

The ratio of cationic lipid to colipid (as a molar ratio) is from about 3:7 to about 7:3. En one embodiment, the ratio of cationic lipid to colipid (molar ratio) is about 4:6 to about 6:4. In a further embodiment the lipid to colipid (molar ratio) is about 4:6. Thus, in one specific, non-limiting example DC-CHOL and DOPE are included in the sterically stabilized cationic liposome at a molar ratio of about 4:6.

Stabilizing agents are also included in the sterically stabilized cationic liposomes disclosed herein. Without being bound by theory, it is believed that the stabilizing agent maintains the integrity of the complex, maintains stability during sizing procedures, and increases shelf life. In one embodiment, the additives are bound to a moiety capable of being incorporated into or binding to the complex, for example, a colipid. Such additives generally are selected from among hydrophilic polymers, which include, but are not limited to, polyethylene glycol, polyvinylpyrrolidine, polymethyloxazoline, polyethyl-oxazoline, polyhydroxypropyl methacrylamide, polylactic acid, polyglycolic acid, and derivatized celluloses such as hydroxymethylcellulose or hydroxyethylcellulose (see published PCT Application No. WO94/22429). Other stabilizing agents include, but are not limited to perfluorinated or partially fluorinated alkyl chains, fluorinated phospholipids, fatty acids and perfluoroalkylated phospholipids and polyglucoronic acids (Oku et al., *Critical Reviews in Therapeutic Drug Carrier Systems,* 11:231-270, 1994).

In one embodiment, the stabilizing agent is polyethylene glycol (PEG). In one specific, non-limiting example, the molecular weight of PEG that can be used ranges from 300 to 20,000 Da. In another embodiment, the molecular weight of the PEG is about 2,000 Da (PEG$_{2000}$) In yet another embodiment, the PEG is derivatized, such as, for example, polyethylene glycol phosphatidyl ethanolamine. In one specific, non-limiting example, the stabilizing agent is polyethylene glycol phosphatidyl ethanolamine (PEG-PE). In another specific, non-limiting example, the phospholipid distearoylphosphatidylethanolamine (DSPE) is derivatized with polyethylene glycol (PEG) to form the stabilizing additive PEG-DSPE. In one embodiment, the stabilizing additive is present as from about one percent to about five percent (about 0.01 to about 0.05) as a molar percent of the colipid. In one embodiment, the molar ratio of DC-CHOL to DOPE to PEG-PE is about 4:6:0.06.

Without being bound by theory it is believed that each of the three elements, the lipid, co-lipid, and the stabilizing agent, each have a specific function in the sterically stabilized cationic liposome (SSCL). Thus, in a specific non-limiting example, DC-CHOL increases liposome membrane stability while improving the uptake and encapsulation of DNA; DOPE (a pH-sensitive neutral lipid) improves the cytosolic delivery of K type CpG ODNs following internalization; and PEG-PE stabilizes the liposome and also facilitates cellular uptake.

In one embodiment, the SSCL complexes include DC-CHOL, DOPE, and PEG-PE, present at a concentration range of 2 to 30 micromoles to provide efficient encapsulation and cellular uptake of CpG ODN. In a more preferred embodiment, the molar range is 10 to 20 micromoles and contains 0.5 to 1.0 mg/ml of K type CpG ODN.

In one specific, non-limiting example, a final liposome concentration is about 10 to about 100 µM lipid/mg K type CpG ODN. In another specific, non-limiting example, a final liposome concentration is about 15 to about 50 µM lipid/mg K type CpG ODN. In a further specific, non-limiting example, a final liposome concentration is about 20 µM lipid/mg K type CpG ODN.

In one embodiment, the SSCL are of a specific particle size. In one embodiment, the SSCLs are 150 nm in diameter, or less, with the majority being approximately 150 nm. In a second embodiment, the SSCLs are about 100 nm in diameter or less. In other embodiment, the SSCL are of about 100 nm in diameter, about 50 nm in diameter, or about 25 nm in diameter. In yet another embodiment, SSCL or/and SSCL-nucleic acid complexes may be extruded through membranes having pores of about 200 nm diameter to form SSCL of about 150 nm in diameter. In a further embodiment, a membrane is utilized that has a pore diameter of about 100 nm. Particle size may be selected for optimal use in a particular application. For example, where a particular clinical application involves extravasation of the cationic lipid-nucleic acid complexes, the particle size may be about 80 nm or lower. Measurements of particle size can be made by a number of techniques including, but not limited to, dynamic laser light scattering (photon correlation spectroscopy, PCS), as well as other techniques known to those skilled in the art (see Washington, *Particle Size Analysis in Pharmaceutics and other Industries,* Ellis Horwood, New York, 1992, pp. 135-169).

In another embodiment, the SSCL contain targeting molecules that can deliver the K type CpG ODN complexes to specific tissue sites or cells in vivo. For example, cell specific monoclonal antibodies can be incorporated in the SSCL in order to target K type CpG ODN to a specific cell type or organ in vivo, including, but not limited to, cells of the immune system, lung, liver, skin, intestine, etc. Alternatively, chemical agents, cell-specific peptides, or ligands for a specific receptor, may be incorporated in the SSCLS, or used to modify one or more of the phospholipid elements. In one embodiment, a cytokine is incorporated into an SSCL to direct delivery of the K type CpG ODN to cells expressing the receptor for the cytokine.

Many ligands may be employed for this step of liposome preparation, depending on the cell type targeted for liposome delivery. For example, any cell-specific surface marker (such as CD4, CD8, CD19, etc) or specific receptor (such as CD40, transferrin, folate, mannose, or a cytokine receptor) could be targeted by attaching a specific antibody or ligand to the surface of the SSCL. Those skilled in the art would readily recognize that any ligand which is specific for immune cells, or enhances uptake in a given tissue, may be an appropriate candidate for targeting the SSCLs encapsulating the CpG ODN.

In one embodiment, the SSCLs encapsulating a CpG ODN, as disclosed herein, are conjugated to the Fab' fragment of an antibody, which acts as a targeting molecule and enables the SSCLs encapsulating a CpG ODN to specifically bind a target cell bearing the antigen. Smaller peptides from the hypervariable region or from another peptide interacting with a specific cell surface ligand may also be conjugated to the complexes. In general terms, the Fab' fragment of an antibody represents a monomer comprising the variable regions and the CH1 region of one arm of an antibody. The Fab' fragments can be derived from antibodies of animal (especially mouse or rat) or human origin or may be chimeric (Morrison et al., Proc. Natl. Acad. Sci. USA 81:6851-6855, 1984) or humanized (Jones et al., Nature 321:522-525, 1986, and published UK patent application No. 8707252). Antibodies of interest include, but are not limited to BR96 (Friedman et al., Cancer Res. 53:334-339, 1993), e23 to erbB2 (Batra et al, Proc. Natl. Acad. Sci. USA 89:5867-5871, 1992); PR1 in prostate cancer (Brinkmann et al., Proc. Natl. Acad. Sci. USA 90:547-551, 1993); and K1 in ovarian cancer (Chang et al. Int. J. Cancer 50: 373-381, 1992).

The Fab' fragment is selected to specifically bind to a molecule or marker characteristic of the surface of the cells to which it is desired to deliver the CpG ODN. A molecule is characteristic of cell, tissue, or physiological state when that molecule is typically found in association with that cell type or alternatively in a multiplicity of cell types all expressing a particular physiological condition (e.g., transformation or tumorigenesis). A specific characteristic marker is preferably found on the surfaces of cells of a particular tissue or cell type or on the surfaces of tissues or cells expressing a particular physiological condition and on no other tissue or cell type in the organism. One of skill will recognize however, that such a level of specificity of the marker is often not required. For example a characteristic cell surface marker will show sufficient tissue specificity if the only non-target tissues are not accessible to the SSCLs encapsulating a CpG ODN. Alternatively, effective specificity may be achieved by over-expression of the marker in the target tissue as compared to other tissues. This will result in preferential uptake by the target tissue leading to effective tissue specificity. Thus for example, many cancers are characterized by the over-expression of cell surface markers such as the HER2 (c-erbB-2, neu) proto-oncogene encoded receptor in the case of breast cancer.

Many cell surface markers exist that provide good characteristic markers depending on the particular tissue it is desired to target. These cell surface markers include, but are not limited to carbohydrates, proteins, glycoproteins, MHC complexes, interleukins, and receptor proteins such as HER, CD4 and CD8 receptor proteins as well as other growth factor and hormone receptor proteins.

In one embodiment, the cell surface marker is a growth factor receptor. Growth factor receptors are cell surface receptors that specifically bind growth factors and thereby mediate a cellular response characteristic of the particular growth factor. Specific, non-limiting examples of growth factors of interest include, but are not limited to, the HER family of growth factor receptors (HER1, HER2, HER3, HER4), platelet-derived growth factor (PDGF), epidermal growth factor (EGF), insulin-like growth factor (IGF), amongst others.

In one embodiment SSCL including a targeting molecule can be prepared by incorporating the Fab' fragment into the liposomes or lipids by a variety of techniques well known to those of skill in the art. The Fab' is added to the SSCLs encapsulating a CpG ODN either before or after complex formation. For example, a biotin conjugated Fab' may be bound to a liposome containing a streptavidin. Alternatively, the biotinylated Fab' may be conjugated to a biotin derivatized liposome by an avidin or streptavidin linker. Thus, for example, a biotinylated monoclonal antibody was biotinylated and attached to liposomes containing biotinylated phosphatidylethanolamine by means of an avidin linker (see, e.g., Ahmad et al., Cancer Res. 52:4817-4820, 1992). Typically about 30 to 125 and more typically about 50 to 100 Fab' fragments per SSCLs encapsulating a CpG ODN are used.

In one embodiment, the targeting moiety is directly conjugated to the liposome. Such means of direct conjugation are well known to those of skill in the art (see, e.g., Gregoriadis, Liposome Technology (1984) and Lasic, Liposomes: from Physics to Applications (1993)). Particularly preferred is conjugation through a thioether linkage. This may be accomplished by reacting the antibody or other targeting molecule with a maleimide derivatized lipid such as maleimide derivatized phosphatidylethanolamine (M-PE) or dipalinitoylethanolamine (M-DEP). This approach is described in detail by Martin et al., J. Biol. Chem. 257:286-288, 1982).

In another embodiment, after encapsulation of CpG ODN in the SSCL, ligands are added directly to the exterior surface of the SSCL complexes. The stability and net positive charge of the SSCLs allow ligands to be directly added to their exterior surface either through incorporating a modified lipid moiety that allows attachment of the ligand or to the terminus of the PEG-PE.

SSCL Preparation

A variety of methods are available for preparing liposomes as described in, e.g., Szoka et al., Ann. Rev. Biophys. Bioeng. 9:467, 1980; U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Szoka & Papahadjopoulos, Proc. Natl. Acad. Sci. USA 75: 4194-4198, 1978; Deamer & Bangham, Biochim. Biophys. Acta 443:629-634, 1976; Fraley et al., Proc. Natl. Acad. Sci. USA 76:3348-3352, 1979; Hope et al., Biochim. Biophys. Acta 812: 55-65, 1985; Mayer et al., Biochim. Biophys. Acta 858:161-168, 1986; Williams et al., Proc. Natl. Acad. Sci. USA 85:242-246, 1988, Liposomes, ch. 1 (Ostro, ed., 1983); and Hope et al., Chem. Phys. Lip. 40:89, 1986; U.S. Pat. No. 6,410,049. Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be re-dissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Unilammellar liposomes can be produced by the reverse phase evaporation method of Szoka & Papahadjopoulos, Proc. Natl. Acad. Sci. USA 75:4194-4198, 1978. Unilamellar vesicles are generally prepared by sonication or extrusion of pre-formed multilammelar vesicles. Small unilamellar vesicles are generally larger than about 0.5 nm in diameter, and less than about 100 nm in diameter, while large unilamellar vesicles are greater than about 100 nm and less than about 500 nm in diameter.

Disclosed herein is a novel method to produce a sterically stabilized cationic liposome (SSCL). In this method a multilamellar vesicle (MLV) is first prepared. The small unilamellar vesicles are then prepared from the MLVs by any method known to one of skill in the art. In one embodiment, unilamellar vesicles are prepared by sonication. In another embodiment, the unilamellar vesicles are prepared by extrusion. The unilamellar vesicles are contacted with an agent of interest, such as, but not limited to, a CpG ODN, a nucleic acid, or a protein of interest. In one embodiment, a K type CpG ODN is dehydrated or freeze-dried in the presence of the unilamellar vesicles. For example, about 0.05 mg to about 5 mg ODN in total lipids of about 1 to about 50 micromole, or about 0.1 to about 2 mg ODN in total lipids of about 2 to about 30 micromole. The unilamellar vesicles and the agent of interest are subsequently dehydrated or freeze-dried. The freeze-dried unilamellar vesicles and the agent of interest are then rehydrated using a suitable medium. Without being bound by theory, the agent of interest, such as the CpG ODN is thus encapsulated throughout the rehydration process, and not simple associated with the SSCL.

In one embodiment, SSCLs are prepared by dehydrating (e.g., by freeze drying) in the presence of K type CpG ODN (e.g., 0.1-2 mg ODN in total lipids of 2-30 micromole) then rehydrating, and extrusion of the liposome structures. Generally the method requires that the lipid components be dissolved in an organic solvent (such as chloroform), mixed in appropriate ratios, and the mixture evaporated under vacuum. This generates a dry lipid film that must be kept in an oxygen free environment. The lipids are then re-suspended in PBS and sonicated to generate small unilamellar vesicles. The appropriate concentration of CpG ODN (typically about 1 mg/ml) is then added to the liposomes, mixed, and freeze-dried overnight. When this mixture is rehydrated in distilled water, ODN encapsulation occurs. A salt solution (such as PBS) is added to the preparation, which is then extruded through polycarbonate filters to generate liposomes of appropriate size. In one embodiment, the liposomes are about 20 to about 200 nm, or about 150 nm, about 100 nm, about 50 nm, or about 25 nm.

Pharmaceutical Compositions

The SSCL encapsulating a CpG ODN (K type) can be formulated in a variety of ways depending on the location and type of disease to be treated (see below). Thus, pharmaceutical compositions are disclosed herein that include at least one SCLs encapsulating a CpG ODN formulated for use in human or veterinary medicine. Such compositions can include physiologically acceptable carriers or excipients. Acceptable carriers include, but are not limited to, glucose, saline, and phosphate buffered saline. The pharmaceutical compositions can optionally include supplementary medicinal agents. These agents include, but are not limited to, pharmaceutical compounds, chemotherapeutic agents, cytokines, and anti-angiogenic agents (see below).

Formulations for injection may be presented in unit dosage form in ampoules, or in multi-dose containers with an added preservative. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the active ingredient may be in powder form for reconstitution with a suitable vehicle, e.g. sterile water, before use.

The SSCLs encapsulating a CpG ODN can be formulated for administration in any convenient way. For example, for administration to the lung, compositions can be administered transbronchially as a spray or mist. SSCL compositions can also be administered to tissue locally during surgery. For example, the compositions can be administered into the peritoneal cavity as a mist during surgery. Alternatively, SSCLs encapsulating a CpG ODN could be given transcutaneously as in the form of a patch applied on the skin.

For oral administration, the pharmaceutical compositions may take the form of, for example, tablets, capsules, powders, solutions, syrups or suspensions prepared by conventional means with acceptable excipients.

Dosages are discussed in more detail below, and will depend on the extent to which it is possible to present CpG ODNs, as well as any other active agents, to the target tissue.

The methods of preparation described herein optimize CpG ODN encapsulation and produce SSCLs encapsulating a CpG ODN which maintain the activity and structural stability of labile co-incorporated molecules. In one embodiment, a method is provided to produce a pharmaceutical composition. The method includes encapuslating a K type ODN in a cationic liposome, and adding a pharmaceutically acceptable carrier, thereby producing the pharmaceutical composition.

As discussed below, SSCLs encapsulating CpG ODN can be administered to a mammalian host to effectively deliver CpG ODN to a target cell. Without being bound by theory, the SSCLs protect CpG ODN from degradation in vivo, and facilitate its uptake by immune cells. Thus, a liposome carrier system is disclosed herein that improves the therapeutic efficacy of CpG ODNs for the prevention and treatment of a variety of infectious diseases, cancer, allergy, and other disorders.

Methods of Inducing an Immune Response

SSCLs encapsulating a K type CpG ODN can be used to enhance an immune response. Thus, a method is disclosed herein for stimulating a cell of the immune system. The method includes contacting the cell with an effective amount of SSCLs encapsulating a K type CpG ODN, as disclosed herein, thereby stimulating the cell (see also PCT Application Nos. WO 00/61151A3, WO 99/56755A1, WO 98/40100A1, WO 98/18810A1, WO 01/22990A2; which are herein incorporated by reference in their entirety). Administration of an SSCL encapsulating a K type CpG ODN can be by any suitable method. For example, the ODN can be administered ill vivo or ex vivo.

Thus, in one embodiment, a method is also disclosed herein for producing an immune response in a subject. The subject can be any mammal, particularly a primate, such as a human. The method includes administering a therapeutically effective amount of an SSCL encapsulating a K type CpG ODN to the subject, thereby inducing the immune response. In yet one embodiment, the immune response includes a component of a cellular response. In a further embodiment, the immune response includes the production of a cytokine, such as, for example, IL-6, IL-12 or IFNγ.

In one embodiment, a method is provided for inducing an immune response in a subject wherein the method includes contacting an immune cell in vitro with a SSCLs encapsulating a K type CpG ODN. The cell can be contacted with SSCLs encapsulating a K type CpG ODN in the presence of or in the absence of antigen. The activated cell is then administered to the subject to induce an immune response.

In order to induce an immune response, a SSCLs encapsulating a K type CpG ODN is administered either alone or in conjunction with another molecule. Co-administration includes administering the molecule and the SSCLs encapsulating a K type CpG ODN at the same time, or sequentially. The other molecule can be any other agent, such as a protein, an antigenic epitope, a hydrocarbon, lipid, mitogen, an anti-infectious agent (such as antiviral, antifungal, or anti-bacterial agent) or a vaccine (such as a live, attenuated, or heat-killed vaccine).

In one embodiment, a SSCLs encapsulating a K type CpG ODN is administered to a subject, such as a subject that has an autoimmune disease. Specific, non-limiting examples of autoimmune diseases include, but are not limited to diabetes, rheumatoid arthritis, lupus erythematosus, and multiple sclerosis. In one embodiment, the subject has cancer.

Also disclosed herein are methods of use to treat, prevent, or ameliorate an allergic reaction in a subject. An allergy refers to an acquired hypersensitivity to a substance (i.e., an allergen). Allergic conditions include eczema, allergic rhinitis or coryza, hay fever, bronchial asthma, uticaria (hives), food allergies and other atopic conditions. The list of allergens is extensive and includes pollens, insect venoms, animal dander, dust, fungal spores, and drugs (e.g., penicillin). Examples of natural, animal, and plant allergens can be found in International Patent Application WO 98/18810. In one embodiment a SSCLs encapsulating a K type CpG ODN is administered to a subject to treat an allergic condition such as allergic asthma. In another embodiment, the SSCLs encapsulating a K type CpG ODN is administered in combination with any suitable anti-allergenic agent. Suitable anti-allergenic agents include those substances given in treatment of the various allergic conditions described above, examples of which can be found in the Physicians' Desk Reference (1998).

In another embodiment, a SSCLs encapsulating a K type CpG ODN is administered to a subject that has a neoplasm. The SSCLs encapsulating a K type CpG ODN is administered either alone or in combination with any suitable anti-neoplastic agent, such as a chemotherapeutic agent, a recombinant biological agent or radiation (see below). Suitable neoplasms include, but are not limited to, solid tumors such as cancers of the brain, lung (e.g., small cell and non-small cell), head and neck, AIDS-associated Kaposi's tumors, ovary, breast, prostate, and colon, as well as carcinomas and sarcomas.

In a further embodiment, a method is provided to enhance the efficacy of any suitable vaccine. Suitable vaccines include those directed against Leishmania, Hepatitis A, B, and C, examples of which can be found in the Physicians' Desk Reference (1998), and DNA vaccines directed against, for example, malaria. (See generally Klinman et al., *Vaccine* 17:19,1999; McCluskie and Davis, *J. Immun.* 161:4463, 1998).

SSCLs encapsulating a K type CpG ODN can be used to treat, prevent, or ameliorate any condition associated with an infectious agent. The SSCLs encapsulating a K type CpG ODN can be administered to a subject infected with the infectious agent alone or in combination with any suitable anti-infectious agent, such as an antiviral, anti-fungal or anti-bacterial agent (see Physicians' Desk Reference, 1998). Specific, non-limiting examples of infectious agents conditions associated with infectious agents are tularemia, francisella, schistosomiasis, tuberculosis, malaria, and leishmaniasis. Examples of infectious agents are viruses, bacteria, fungi, and other organisms (e.g., protists) can be found in International Patent Application WO 98/18810.

The SSCLs encapsulating a K type CpG ODN disclosed herein can also be used with any suitable antisense therapy. Suitable antisense agents are those that specifically bind either with a target DNA or a target RNA and inhibit expression of the target sequence (see Lonnberg et al., *Ann. Med.* 28:511, 1996; Alama et al., *Pharmacol. Res.* 36:171, 1997; Scanlon et al., *FASEB J.* 9:1288, 1995; Oberbauer, *Wien Klin Wochenschr* 109:40, 1997).

Methods of Treating of a Tumor

As disclosed herein, SSCLs encapsulating a K type CpG ODN can be used to enhance an immune response to a tumor. In one embodiment, the SSCLs encapsulating a K type CpG ODN can be administered in conjunction with a chemotherapeutic agent or a biological agent. In one embodiment, the agent is chimeric molecule comprising a targeting molecule attached to an effector molecule. The chimeric molecule specifically targets tumor cells while providing reduced binding to non-target cells. In one embodiment, the chimeric molecule is a ligand that specifically binds a receptor on the tumor, conjugated to an effector molecule, such as a cytotoxin. In one specific, non-limiting example, the targeting molecule is IL-13, or an antibody that binds the IL-13 receptor. In another specific, non-limiting example, the chimeric molecule is IL13-PE (see below). Thus, a therapeutically effective amount of an SSCL encapsulating a K type CpG ODN is administered to a subject with a tumor in conjunction with a therapeutically effective amount of IL13-PE. Administration of the SSCL encapsulating a K type CpG ODN in conjunction with IL-13 chimeric molecule results in impairment of the growth, or a decrease in the size, of the tumor. In one embodiment, the tumor is a solid tumor, such as a carcinoma. Specific, non-limiting examples of carcinomas include carcinoma of the breast and head and neck tumors.

Solid tumors, especially carcinomas, overexpress IL-13 receptors at extremely high levels. While the IL-13 receptors are overexpressed on tumor cells, expression on other cells (e.g. monocytes, B cells and T cells) appears negligible. Thus, by specifically targeting the IL-13 receptor, the chimeric molecules can be utilized that are specifically directed to solid tumors while minimizing targeting of other cells or tissues. These chimeric molecules have been described in U.S. Pat. No. 5,614,191 and U.S. Pat. No. 5,919,456, which are herein incorporated by reference in their entirety. IL-13 chimeric molecules are briefly described below.

IL-13 chimeric molecules include an effector molecule attached to a targeting molecule that specifically binds an IL-13 receptor. The effector molecule can be a cytotoxin (either a native or modified cytotoxin) such as *Pseudomonas* exotoxin (PE), Diphtheria toxin (DT), ricin, abrin, and the like. In still yet another embodiment the effector molecule can be a pharmacological agent (e.g. a drug) or a vehicle containing a pharmacological agent. This is particularly suitable where it is merely desired to invoke a non-lethal biological response. Thus the moiety that specifically binds to an IL-13 receptor may be conjugated to a drug such as vinblastine, doxorubicin, genistein (a tyrosine kinase inhibitor), an antisense molecule, and other pharmacological agents known to those of skill in the art, thereby specifically targeting the pharmacological agent to tumor cells over expressing IL-13 receptors. In a further embodiment, the effector molecule can be a ribosomal inactivating protein. Effector molecules include cytotoxins such as *Pseudomonas* exotoxin (PE) or diphtheria toxin (DT), radionuclides, ligands such as growth factors, antibodies, and therapeutic compositions such various drugs. Cytotoxins include, but are not limited to, *Pseudomonas* exotoxins, Diphtheria toxins, ricin, and abrin. *Pseudomonas* exotoxin and Diphtheria toxin are most preferred.

*Pseudomonas* exotoxin (PE) A is an extremely active monomeric protein (molecular weight 66 kD), secreted by *Pseudomonas aeruginosa,* which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2). The toxin contains three structural domains that act in concert to cause cytotoxicity. Domain Ia (amino acids 1-252) mediates cell binding. Domain II (amino acids 253-364) is responsible for translocation into the cytosol and domain m (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity (Siegall et al., *J. Biol. Chem.* 264:14256-14261, 1989).

Where the targeting molecule (e.g. IL-13, or an antibody that specifically binds IL-13) is fused to PE, one PE molecule of use is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as four glycine residues followed by a serine. In addition, the PE molecules can be further modified using site-directed mutagenesis or other techniques known in the art, to alter the molecule for a particular desired application. Maximum cytotoxic properties have been achieved using several modifications. An appropriate carboxyl terminal sequence can be added to the recombinant molecule to translocate the molecule into the cytosol of target cells. Amino acid sequences which have been found to be effective include, arginine, followed by EDL and optionally followed by lysine (as in native PE), or DEL preceded by either an arginine or a lysine repeats of those, or other sequences that function to maintain or recycle proteins into the endoplasmic reticulum, referred to here as "endoplasmic retention sequences" (Chaudhary et al, *Proc. Natl. Acad. Sci. USA* 87:308-312, 1990; Seetharam et al, *J. Biol. Chem.* 266: 17376-17381, 1991).

Deletions of amino acids 365-380 of domain Tb can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial. In one embodiment, the targeting molecule is inserted in replacement for domain Ia. One form of PE of use contains amino acids 253-364 and 381-608, and are followed by the native sequences arginine, followed by EDL and further followed by lysine (as in native PE), or the mutant sequences DEL preceded by either an arginine or a lysine. Lysines at positions 590 and 606 may or may not be mutated to glutamine.

In one embodiment, the IL-13 receptor targeted cytotoxins of use with the methods disclosed herein include the PE molecule designated PE38QQR. This PE molecule is a truncated form of PE composed of amino acids 253-364 and 381-608. The lysine residues at positions 509 and 606 are replaced by glutamine and at 613 are replaced by arginine (Debinski et al., *Bioconj. Chem.* 5:40, 1994, see also U.S. Pat. No. 5,614,191 and U.S. Pat. No. 5,919,456, which are both incorporated herein by reference in their entirety). Other PE molecules of use include PE38, PE4E, PE38KDEL (see U.S. Pat. No. 5,614,191 and U.S. Pat. No. 5,919,456).

The targeting molecule (e.g. IL13 or anti-IL-13R antibody, see below) can also be inserted at a point within domain III of the PE molecule. In one embodiment, the targeting molecule is fused between about amino acid positions 607 and 609 of the PE molecule. This means that the targeting molecule is inserted after about amino acid 607 of the molecule and an appropriate carboxyl end of PE is recreated by placing amino acids about 604-613 of PE after the targeting molecule. Thus, the targeting molecule is inserted within the recombinant PE molecule after about amino acid 607 and is followed by amino acids 604-613 of domain III. The targeting molecule xN also be inserted into domain Ib to replace sequences not necessary for toxicity (Debinski et al., *Mol. Cell. Biol.* 11:1751-1753, 1991).

Those skilled in the art will realize that additional modifications, deletions, insertions and the like may be made to the chimeric molecules or to the nucleic acid sequences encoding IL-13 receptor-directed chimeric molecules. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science* 175: 901-903, 1972; Uchida et al., *J. Biol. Chem.,* 248:3838-3844, 1973).

In one embodiment, the targeting molecule-Diphtheria toxin fusion proteins have the native receptor-binding domain removed by truncation of the Diphtheria toxin B chain. One specific non-limiting example is DT388, a DT in which the carboxyl terminal sequence beginning at residue 389 is removed (Chaudhary et al., *Bioch. Biophys. Res. Comm.,* 180:545-551, 1991).

Like the PE chimeric cytotoxins, the DT molecules may be chemically conjugated to the IL-13 receptor targeting molecule, but, in one embodiment, the targeting molecule will be fused to the Diphtheria toxin by recombinant means. The genes encoding protein chains may be cloned in cDNA or in genomic form by any cloning procedure known to those skilled in the art. Methods of cloning genes encoding DT fused to various ligands are also well known to those of skill in the art (see, for example, Williams et al., *J. Biol. Chem.* 265:11885-11889, 1990). A DT includes full length native DT or to a DT that has been modified. Modifications typically include removal of the targeting domain in the B chain and, more specifically, involve truncations of the carboxyl region of the B chain.

In another embodiment, the effector molecule can also be a ligand or an antibody. For example, ligand and antibodies can be utilized that bind to surface markers of immune cells. Chimetic molecules utilizing such antibodies as effector molecules act as bifunctional linkers establishing an association between the immune cells bearing binding partner for the ligand or antibody and the tumor cells overexpressing the IL-13 receptor. Suitable antibodies and growth factors are known to those of skill in the art and include, but are not limited to, IL-2, IL4, IL-6, IL-7, tumor necrosis factor (TNF), anti-Tac, TGF-α, urokinase, transferin, epidermal growth factor (EGF), and the like.

Other suitable effector molecules include pharmacological agents. Thus, the targeting molecule of the chimeric molecule may be attached directly to a drug that is to be delivered directly to the tumor. Such drugs are well known to those of skill in the art and include, but are not limited to, doxorubicin, vinblastine, genistein, an antisense molecule, and the like.

In one embodiment, the targeting molecule is a molecule that specifically binds to the IL-13 receptor. The term "specifically binds", as used herein, when referring to a protein or polypeptide, refers to a binding reaction which is determinative of the presence of the protein or polypeptide in a heterogeneous population of proteins and other biologics. Thus, under designated conditions (e.g. immunoassay conditions in the case of an antibody), the specified ligand or antibody binds to its particular "target" protein (e.g. an IL-13 receptor protein) and does not bind in a significant amount to other proteins present in the sample or to other proteins to which the ligand or antibody may come in contact in an organism.

In one embodiment, the targeting molecule is an antibody. A variety of immunoassay formats may be used to select antibodies specifically immunoreactive with an IL-13 receptor protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

Polyclonal and monoclonal antibodies directed against IL-13 receptors provide particularly suitable targeting molecules in the chimeric molecules. The antibody may be of animal (especially mouse or rat) or human origin or may be chimeric (Morrison et al., *Proc Nat. Acad. Sci. USA* 81:6851-6855, 1984) or humanized (Jones et al., *Nature* 321:522-525, 1986, published UK patent application No. 8707252). Methods of producing antibodies suitable for use are well known to those skilled in the art and can be found described in such publications as Harlow & Lane, *Antibodies: A Laboratory Manual*, Cold Spring Harbor Laboratory (1988), and Asai, *Methods in Cell Biology Vol. 37: Antibodies in Cell Biology*, Academic Press, Inc. New York (1993). Generally, this involves using an antigenic component of the IL-13 receptor as an antigen to induce the production of antibodies in an organism (e.g. a sheep, mouse, rabbit, etc.). Methods of isolating an antigenic component of IL-13, and methods of isolating IL-13 antibodies and producing IL-13 antibodies are disclosed, for example, in U.S. Pat. No. 5,919,456.

In another embodiment, the targeting molecule is IL-13 or an analogue or fragment of IL-13 that specifically bind to the IL-13 receptor. For example. conservative substitutions of residues (e.g., a serine for an alanine or an aspartic acid for a glutamic acid) comprising native IL-13 will provide IL-13 analogues that also specifically bind to the IL-13 receptor. In one specific, non-limiting example, a fragment, variant, or analog binds to an IL-13 receptor with higher affinity than the parent IL-13 molecule. Thus, the term "IL-13", when used in reference to a targeting molecule, also includes fragments, analogues or peptide mimetics of IL-13 that also specifically bind to the IL-13 receptor.

Other chimeric molecules comprising a targeting moiety joined to a cytotoxic effector molecules to target and kill tumor cells is known in the prior art. For example, chimeric fusion proteins which include interleukin 4 (IL-4) or transforming growth factor (TGF-α) fused to *Pseudomonas* exotoxin (PE) or interleukin 2 (IL-2) fused to Diphtheria toxin (DT) have been tested for their ability to specifically target and kill cancer cells (Pastan et al., *Ann. Rev. Biochem.* 61:331-354, 1992). As disclosed herein, SSCLs encapsulating a CpG ODN can also be used in conjunction with these chimeric molecules to inhibit the growth of a solid tumor expressing receptors for these cytokines.

One of skill in the art will appreciate that the chimeric molecules can include multiple targeting moieties bound to a single effector or conversely, multiple effector molecules bound to a single targeting moiety. In another embodiment, the chimeric molecules may include both multiple targeting moieties and multiple effector molecules. Thus, for example, "dual targeted" cytotoxic chimeric molecules can be utilized in which targeting molecule that specifically binds to IL-13 is attached to a cytotoxic molecule and another molecule (e.g. an antibody, or another ligand) is attached to the other terminus of the toxin. These dual targeted molecules are described in U.S. Pat. No. 5,919,456 and U.S. Pat. No. 5,614,191, which are herein incorporated by reference in their entirety.

Without being bound by theory, the chimeric cytotoxin is administered to an organism containing tumor cells which are then contacted by the chimeric molecule. The targeting molecule component of the chimeric molecule specifically binds to the overexpressed IL-13 receptors on the tumor cells. Once bound to the EL-13 receptor on the cell surface, the cytotoxic effector molecule mediates internalization into the cell where the cytotoxin inhibits cellular growth or kills the cell.

In one embodiment, the effector molecule (e.g. PE molecule) is fused to the targeting molecule by recombinant means. The genes encoding protein chains may be cloned in cDNA or in genomic form by any cloning procedure known to those skilled in the art (see for example Sambrook et al., *Molecular Cloning. A Laboratory Manual*, Cold Spring Harbor Laboratory, (1989). Methods of cloning genes encoding PE fused to various ligands are well known to those of skill in the art (see, for example, Siegall et al., *FASEB J.* 3:2647-2652, 1989; Chaudhary et al., *Proc. Natl. Acad. Sci. USA* 84:4538-4542, 1987).

The targeting molecule and effector molecules can be joined together in any order. Thus, where the targeting molecule is a polypeptide, the effector molecule can be joined to either the amino or carboxy termini of the targeting molecule. The targeting molecule can also be joined to an internal region of the effector molecule, or conversely, the effector molecule can be joined to an internal location of the targeting molecule, as long as the attachment does not interfere with the respective activities of the molecules.

The targeting molecule and the effector molecule can be attached by any of a number of means well known to those of skill in the art. Typically the effector molecule is conjugated, either directly or through a linker (spacer), to the targeting molecule. However, where both the effector molecule and the targeting molecule are polypeptides they can be recombinantly expressed as a single-chain fusion protein.

In one embodiment, the targeting molecule (e.g. IL-13 or anti-IL-13R antibody) is chemically conjugated to the effector molecule (e.g. a cytotoxin, a ligand, or a drug). Methods of chemically conjugating molecules are well known. The procedure for attaching an agent to an antibody or other polypeptide targeting molecule will vary according to the chemical structure of the agent. Polypeptides typically contain variety of functional groups; e.g., carboxylic acid (COOH) or free amine (—NH$_2$) groups, which are available for reaction with a suitable functional group on an effector molecule to bind the effector thereto.

Alternatively, the targeting molecule and/or effector molecule can be derivatized to expose or attach additional reactive functional groups. The derivatization can involve attachment of any of a number of linker molecules such as those available from Pierce Chemical Company, Rockford Ill.

A linker is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). In one embodiment, the linkers are joined to the alpha carbon amino and carboxyl groups of the terminal amino acids.

A bifunctional linker having one functional group reactive with a group on a particular agent, and another group reactive with an antibody, can be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto (see U.S. Pat. No. 4,671,958). Procedures for generation of free sulfhydryl groups on polypeptide, such as antibodies or antibody fragments, are also known (see U.S. Pat. No. 4,659,839).

Many procedures and linker molecules for attachment of various compounds including radionuclide metal chelates, toxins and drugs to proteins such as antibodies are known. See, for example, European patent application No. 188,256; U.S. Pat. Nos. 4,671,958; 4,659,839; 4,414,148; 4,699,148; Borlinghaus et al., *Cancer Res.* 47:4071-4075, 1987, amongst others). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168-190, 1982, Waldmann, *Science* 252:1657, 1991; U.S. Pat. Nos. 4,545, 985 and 4,894,443.

In some circumstances, it is desirable to free the effector molecule from the targeting molecule when the chimeric molecule has reached its target site. Therefore, chimeric conjugates comprising linkages which are cleavable in the vicinity of the target site can be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,225. The mechanisms for release of an agent from these linker groups include, for example, irradiation of a photolabile bond and acid-catalyzed hydrolysis. In one specific, non-limiting example, linkers can be cleaved at the target site in vivo by the proteolytic enzymes of the patient's complement system (see U.S. Pat. No. 4,671,958). Synthesis of targeting molecules, effector molecules, and linkers is described in U.S. Pat. No. 5,614,191 and U.S. Pat. No. 5,919, 456, both of which are incorporated by reference in their entirety.

The disclosure is illustrated by the following non-limiting Examples.

EXAMPLES

Example 1

Materials and Methods

Mice: Specific pathogen-free BALB/c mice (Jackson Laboratories, Bar Harbor, Me.) were housed in sterile microisolator cages.

Oligonucleotides: Immunostimulatory ODN$_{1555}$ (GCTAGA<u>CG</u>TTAGCGT, SEQ ID NO: 1) and ODN$_{1466}$ (TCAA<u>CG</u>TTGA, SEQ ID NO:2), and control ODNs in which the CpG motif was methylated or inverted, were synthesized by the CBER core facility. All ODN were free of endotoxin and protein contamination.

Liposome preparation: Cholesterol and various phospholipids (Avanti Polar lipids, AL. USA) were combined in different ratios to form liposomes that varied in charge, stability, lamellarity, and fluidity (Table I). Lipid stocks were prepared in chloroform and stored at 10 mg/ml under argon at −20° C. until use.

Liposomes were generated by evaporating phospholipid mixtures in a round-bottom flask using a rotary evaporator (Buchi, Switzerland). The solvent-free dry lipid film was purged with argon to eliminate residual chloroform and oxygen, thereby preventing lipid peroxidation. To generate empty multilamellar vesicles, 1 ml of PBS was added to each 20 μmole of dried lipid film. The mixture was shaken to form "empty" small unilamellar vesicles (SUV). These were sonicated 5 times for 30 seconds at 4° C. using a Vibra Cell Sonicator (Sonics and Materials Inc., Danbury, Conn.). The SUVs were then mixed with 1 mg/ml of ODN, frozen on dry ice, and freeze-dried overnight (Flexi-Dry, FTS Systems Inc., NY, USA) (Takeshita et al., *Eur. J. Immunol.* 30:108, 2000).

ODN encapsulation was achieved during rehydration. 100 μl of sterile dH$_2$O was added to the dehydrated liposome/ ODN powder, and vortexed for 15 seconds every 5 minutes for 30 minutes at RT. 900 μl of PBS was added to the mixture, yielding a final liposome concentration of 20 μmole lipid/mg DNA. Vesicles <150 nm in diameter were produced by 20-30 cycles of extrusion through polycarbonate filters using a Liposofast extruder (Avestin Inc. Ottawa Canada) (Klinman and Nutman, in *Current Protocols in Immunology.* 7th ed. J. E. Coligan, A. M. Kruisbeek, D. H. Margulies, E. M. Shevach and W. Strober, eds. Greene Publishing Associates, Brooklyn, N.Y.). Liposome formulations were stored at 4° C. until in use.

Assays: RAW 264.7 mouse macrophages were transiently transfected with an IL-12 p40 promoter-luciferase gene vector (pGL3 basic vector) as described (Sacks and Klinman, *Cellular Immunology* 177:162, 1997). 10$^6$ cells were transfected with 5 μg of plasmid DNA. After 24 h, cells were pooled, washed and cultured for 18 hours with 1 μM ODN in 12 well macroplates. Cells were harvested monitored for luciferase activity as recommended by the manufacturer (Promega, Madison, Wis., USA).

BALB/c spleen cells were prepared in RPMI 1640 supplemented with 5% FCS, 50 mg/ml pen/strep, 2 mM L-glutamine, 10 mM HEPES, 0.11 mg/ml sodium pyruvate and 0.5 mM 2-mercaptoethanol. The cells were cultured at 37° in a 5% CO$_2$ incubator. Single cell suspensions were serially diluted in flat bottomed 96-well microtiter plates that had been pre-coated with anti-cytokine Abs, as described (Yamamoto et al., *Microbiol. Immunol* 38:831, 1994). Cells were incubated with 1 µM ODN (unless otherwise stated) at 37° C. for 8 h, and their secretion of cytokine detected calorimetrically (Klinman et al., *Vaccine* 17:19, 1999). ELISA assays for quantifying cytokines were performed as above, except supernatant rather than cells were added to anti-cytokine coated plates.

In vivo CpG ODN binding and uptake: BALB/c mice were injected IP with 50 µg of free or liposome encapsulated FITC-labeled CpG ODN. Mice were sacrificed 2-48 hours later, and single spleen cell suspensions ($2 \times 10^6$/ml) immediately prepared. One aliquot of cells was fixed and analyzed for FITC-ODN content by FACS (Becton Dickinson, San Jose, Calif.). Another aliquot was stained with PE-labeled phenotype-specific antibodies (Pharmingen, San Diego, Calif.). These included CD11c for dendritic cells, CD11b for macrophages and B220 for B cells. Auto-fluorescence of untreated cells was used to establish assay background.

Antigen specific immune responses: Mice were immunized IP with liposome (0.2 µM lipid/mouse) containing ovalbumin (2 µg, Sigma, St. Louis, Mo.) and/or CpG ODN (10 µg/mouse) on days 0 and 14. Serum was collected on days 14 and 28. IgG, IgG1 and IgG2a anti-OVA titers in serum were determined by ELISA (Yamamoto et al., *Microbiol. Immunol.* 38:831, 1994). Mice were sacrificed on day 28, and a single spleen cell suspension ($2 \times 10^5$ cells/well) prepared in RPMI1640 supplemented with complete medium. Cells were stimulated in vitro with 5 µg of OVA for 36 h. IFNγ levels in culture supernatants were monitored by ELISA (Yamamoto et al., *Microbiol. Immunol.* 38:831, 1994).

Bacteria and growth conditions: *L. monocytogenes* strain EGD (ATCC #15313; American Type Culture Collection, Rockville, Md.) was grown in modified Mueller-Hinton (MH) broth (Difco Laboratories, Detroit, Mich.) (Elkins et al., *J Immunol* 162:2291, 1999). Mice treated with 50 µg of ODN (alone or liposome incorporated) were challenged intraperitoneally 2 or 4 wk later with $10^3$ LD$_{50}$ of *L. monocytogenes* in 500 µl PBS. Survival was monitored for >3 weeks.

Statistical analysis: All cytokine and Ig assays were conducted at least twice on at least 3 independently studied mice/group. All immunization and bacterial challenge experiments were performed on a minimum of 5-10 mice/group. Statistical significance was evaluated using Student's t-test.

Example 2

Effect of Liposome Formulation on CpG ODN Incorporation

Initial experiments evaluated the efficiency with which $^{32}$P-labeled K type CpG ODN were incorporated into various types of lipid vesicle. Anionic liposomes interacted poorly with CpG ODN, attaining encapsulation efficiencies of <40% (Table I, FIG. 6). Neutral and cationic liposomes showed progressively higher levels of encapsulation. Sterically stabilized cationic liposomes (SSCL) composed of a positively charged derivative of cholesterol, a hydrophilic derivative of polyethylene glycol, and the neutral lipid dioleyl phosphatidyl ethanolamine were the most successful in incorporating anionic CpG ODN (Table I, shown in FIG. 6). Incorporation efficiency was influenced by the charge, but not by the size or sequence of the ODNs studied.

Example 3

In vitro Activity of Liposome Encapsulated CpG ODN

Figure 2:
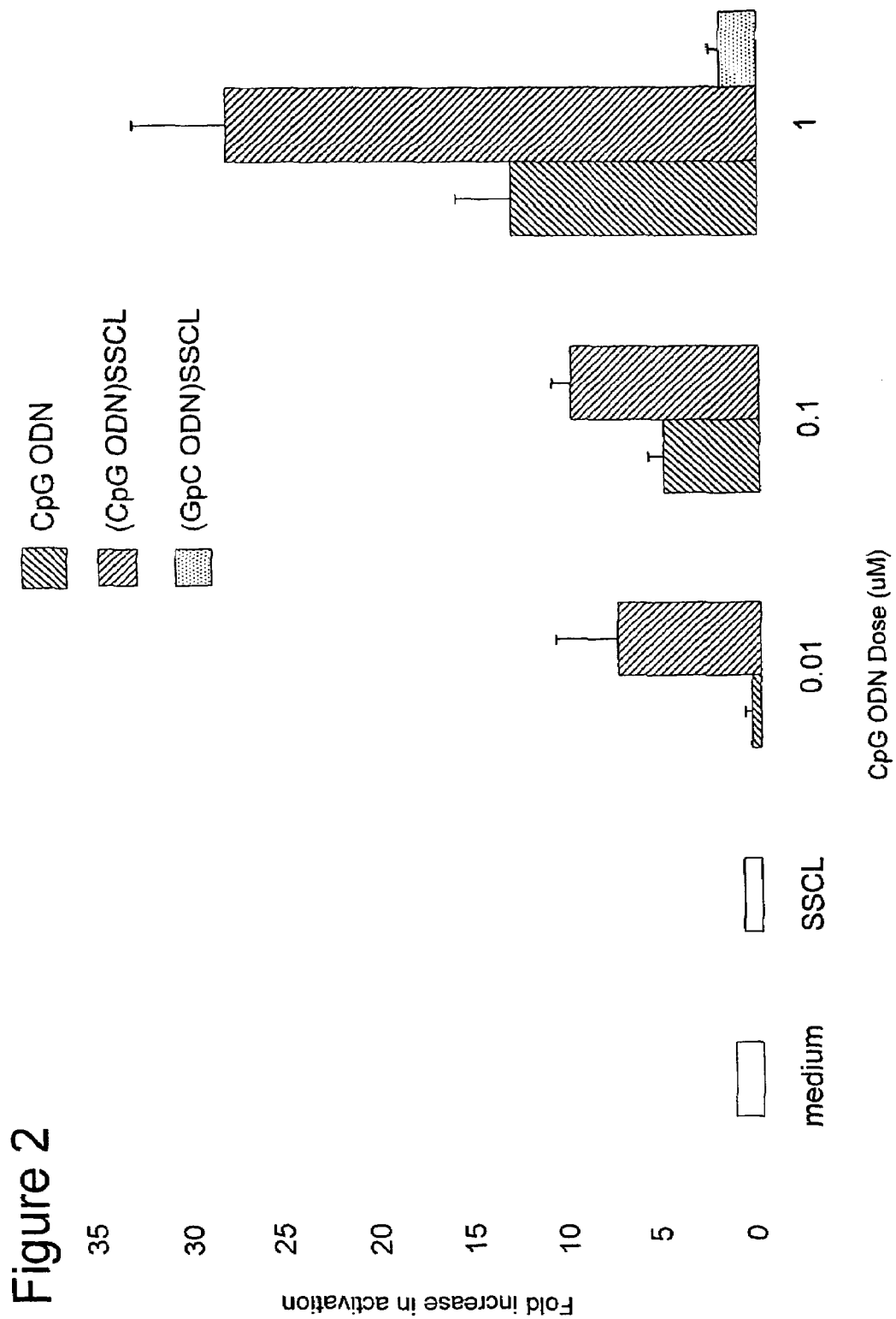
FIG. 2 is a bar graph of the effect of CpG ODN dose on IL12 p40 expression. RAW 264.7 cells were transfected as in FIG. 1 and stimulated with 0.01-1.0 μM of free or SSCL encapsulated CpG ODN. Data show the fold increase in luciferase activity at 24 hours compared to medium alone, and represent the mean+SD of 3 independent experiments. * $p<0.01$ when compared to free CpG ODN.

The ability of CpG ODN to stimulate cells and up-regulate cytokine expression was monitored by transiently transfecting RAW264.7 murine macrophages with an IL-12 p40/luciferase construct. It was previously shown that CpG ODN increase IL-12 p40 promoter activity in this cell line (24). As seen in FIG. 1, RAW264.7 cells treated with SSCL-encapsulated K type CpG ODN [hereafter (CpG ODN)$_{SCCL}$] expressed significantly more luciferase activity than cells treated with an equal amount of free ODN (or ODN in other types of liposome, p<0.01). Moreover, stimulation by (CpG ODN)$_{SSCL}$ persisted at concentrations below the effective range of free CpG ODN (p.<0.001, FIG. 2). The stimulation observed in these experiments was CpG motif dependent, since empty SSCL, or SSCL containing control ODN, did not increase luciferase expression (FIG. 2).

Figure 3:
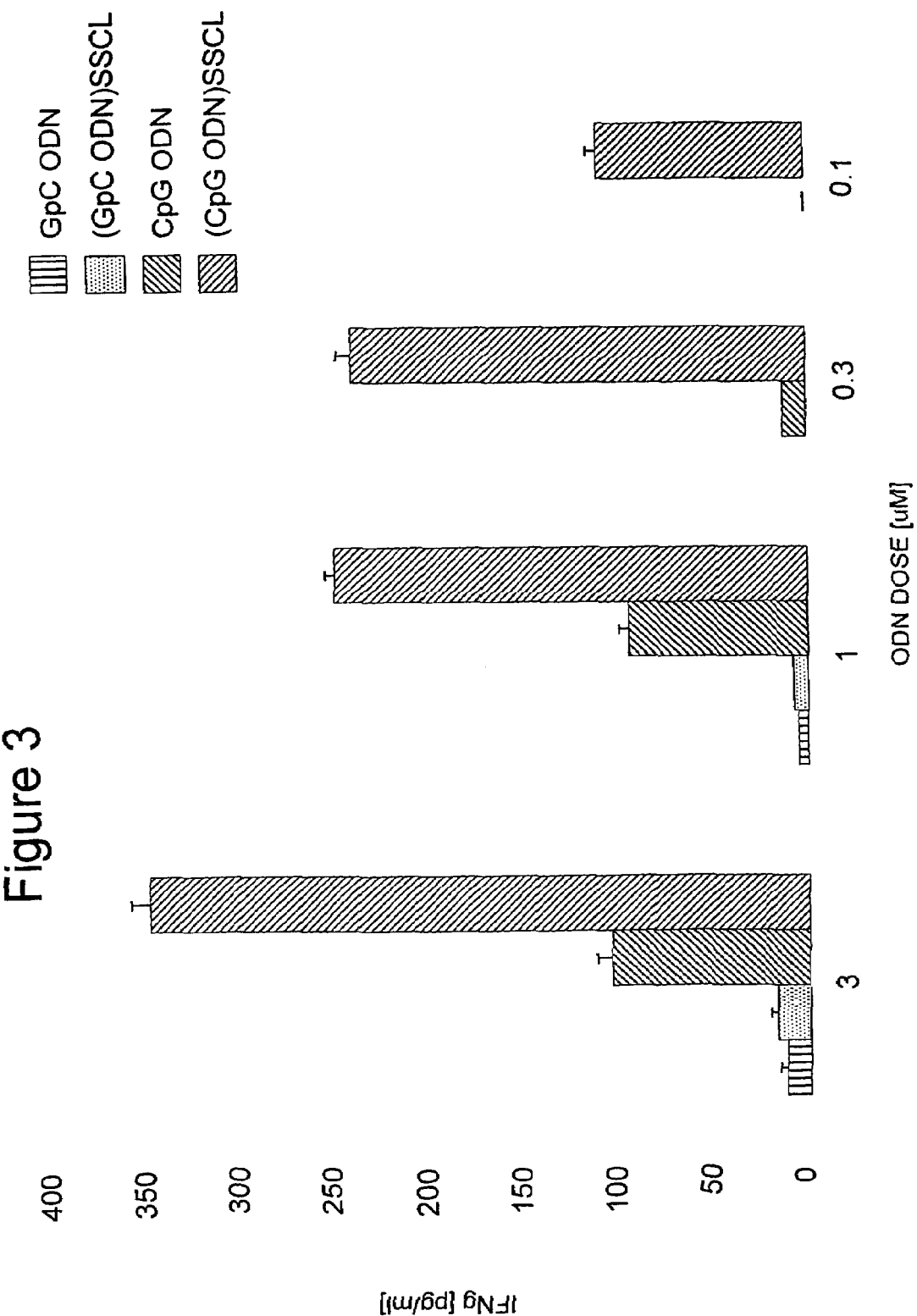
FIG. 3 is a bar graph of the effect of liposome encapsulation on CpG ODN mediated spleen cell activation. BALB/c splenocytes ($2\times10^5$/well) were stimulated with 0.1-3.0 μM ODN. Culture supernatants were collected after 36 hours and assayed for IFNγ by ELISA. Results represent the average +SD of 3 independent experiments, with each assay performed in triplicate in each experiment.* $p<0.01$ when compared to free CpG ODN.

The activity of (CpG ODN)$_{SSCL}$ was confirmed using freshly isolated BALB/c spleen cells. Consistent with previous reports (3,27), free CpG ODN elicited a dose dependent increase in IFNγ production by normal murine spleen cells (FIG. 3). CpG ODN$_{SSCL}$ stimulated significantly more IFNγ production at all concentrations examined (p<0.001). This stimulation was CpG specific, since control ODN did not induce IFNγ (FIG. 3). CpG ODN encapsulated in other types of liposomes were less stimulatory.

Example 4

Uptake of (CpG ODN)$_{SCCL}$ in vivo

Normal BALB/c mice were injected IP with 50 µg of free or SSCL-encapsulated FITC-ODN. Uptake of these ODN by spleen and peritoneal exudate cells 2 hours post injection was significantly higher in mice treated with (CpG ODN)$_{SSCL}$ than free ODN (p<0.05, both sites, Table II shown in FIG. 7). This difference persisted at 24 h, with 3-6 fold more cells incorporating label (p<0.001).

Figure 4:
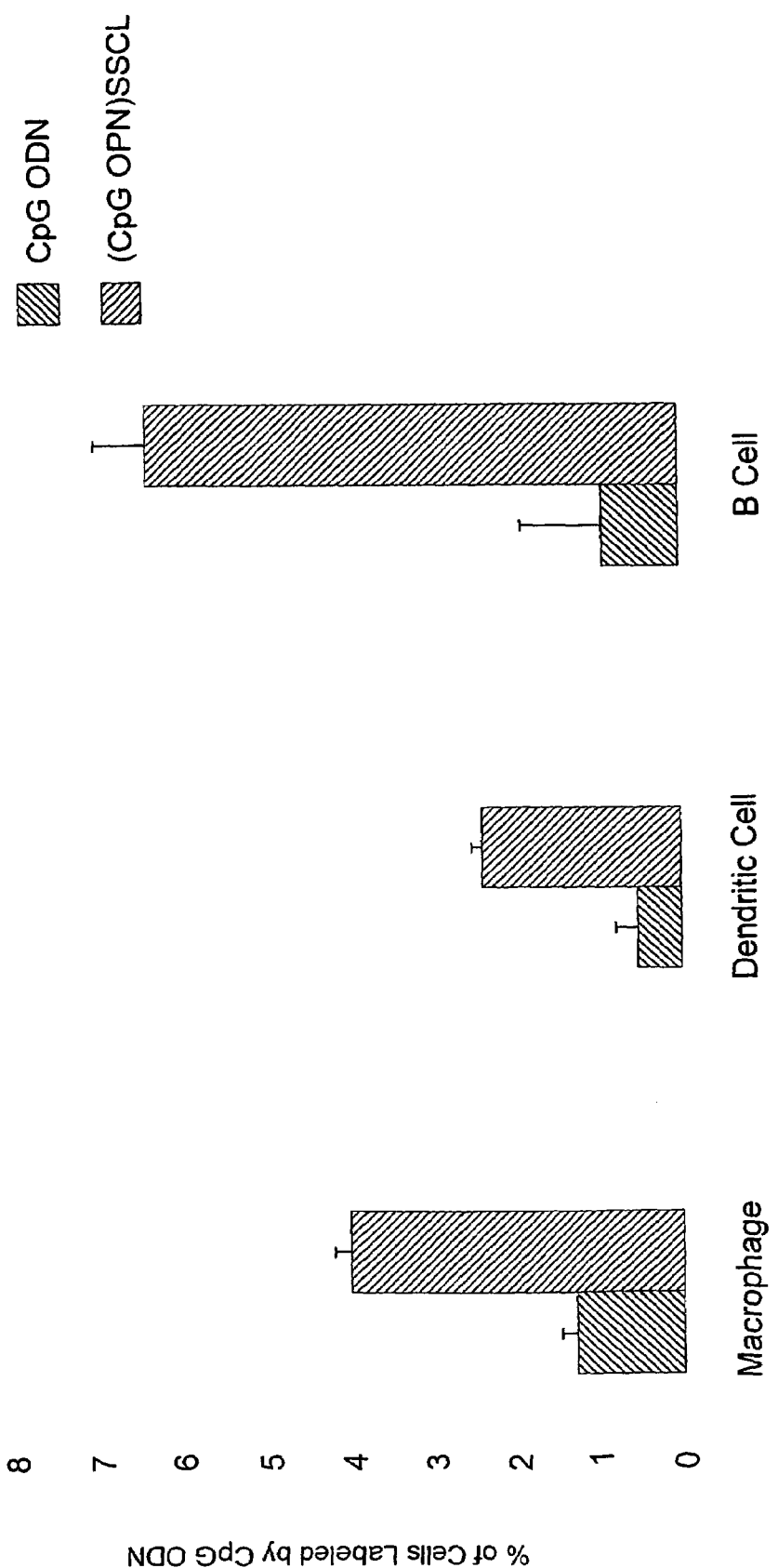
FIG. 4 is a bar graph showing the uptake of (CpG ODN)$_{SSCL}$ by spleen cells.

To determine the phenotype of the cells that bound and internalized (CpG ODN)$_{SSCL}$, spleen cells from these mice were treated with PE-labeled phenotype-specific MAbs. Results indicate that (CpG ODN)$_{SSCL}$ was taken up by significantly more CD11b$^+$ macrophages (1% vs 4%, p<0.01), CD11c$^+$ dendritic cells (0.5% vs 3.0%, p<0.01) and B220$^+$ B cells (1% vs 6%, p<0.01) than free CpG ODN (FIG. 4).

Example 5

In vivo Effects of (CpG ODN)$_{SSCL}$: Immune Cell Activation

Immune activation manifest by increased cytokine production and the up-regulation of CD40 expression was examined in BALB/c mice injected IP with 50 µg of free or SSCL-encapsulated CpG ODN. Results show that spleen cells from (CpG ODN)$_{SSCL}$ treated mice produced significantly more IL-6, IL-12 and IFNγ (p<0.001, Table III, shown in FIG. 8), and expressed higher levels of CD40 (p<0.001, Table III), than did from those mice treated with free CpG ODN. This enhanced immune activation persisted for at least 48 hours (Table III, FIG. 8, p<0.001 for all cytokines). Similar findings were obtained when LN and PEC cells from these animals were analyzed (data not shown). These findings indicate that liposome encapsulation increased both the magnitude and duration of CpG induced immune activation in vivo.

Example 6

In vivo Effects of (CpG ODN)$_{SSCL}$: Adjuvant Activity

CpG ODN can act as immune adjuvants, boosting the immune response to co-administered protein antigens (Klinman et al., *Infect Immun* 67:5658, 1999). For example, co-administering free CpG ODN with ovalbumin (OVA) increases the resultant IgG2a anti-OVA response of BALB/c mice by 6-fold (p<0.01) and IFNγ production by 1.5 fold (Table IV, shown in FIG. 9).

If CpG ODN plus OVA were co-encapsulated in SSCL, a >400-fold increase in the IgG2a anti-OVA response was obtained (p<0.01). This treatment also increased antigen-specific IFNγ production by 15-fold (p<0.01, Table IV).

Optimal immunogenicity was observed when OVA and CpG ODN were encapsulated in the same liposome. Administering free OVA with encapsulated (CpG ODN)$_{SSCL}$ elicited immune responses of significantly lower magnitude (Table IV). These findings are consistent with previous studies showing that optimal immunogenicity requires that the CpG ODN be kept in close physical proximity to antigen (Davis et al., *J. Immunol.* 160:870, 1998).

Example 7

In vivo Effects of (CpG ODN)$_{SSCL}$: Immunoprotective Activity

CpG ODN stimulate an innate immune response that promotes host survival following pathogen challenge (Gurunathan, *Annu. Rev Immunol* 18:927, 2000). While this response protects the host from a broad array of pathogens, it persists for only a short period (<2 wk) (Gurunathan, *Annu. Rev Immunol* 18:927, 2000). Since SSCL encapsulation increases the magnitude and duration of CpG induced cellular activation, its ability to extend the duration of CpG induced protection was examined.

Figure 5:
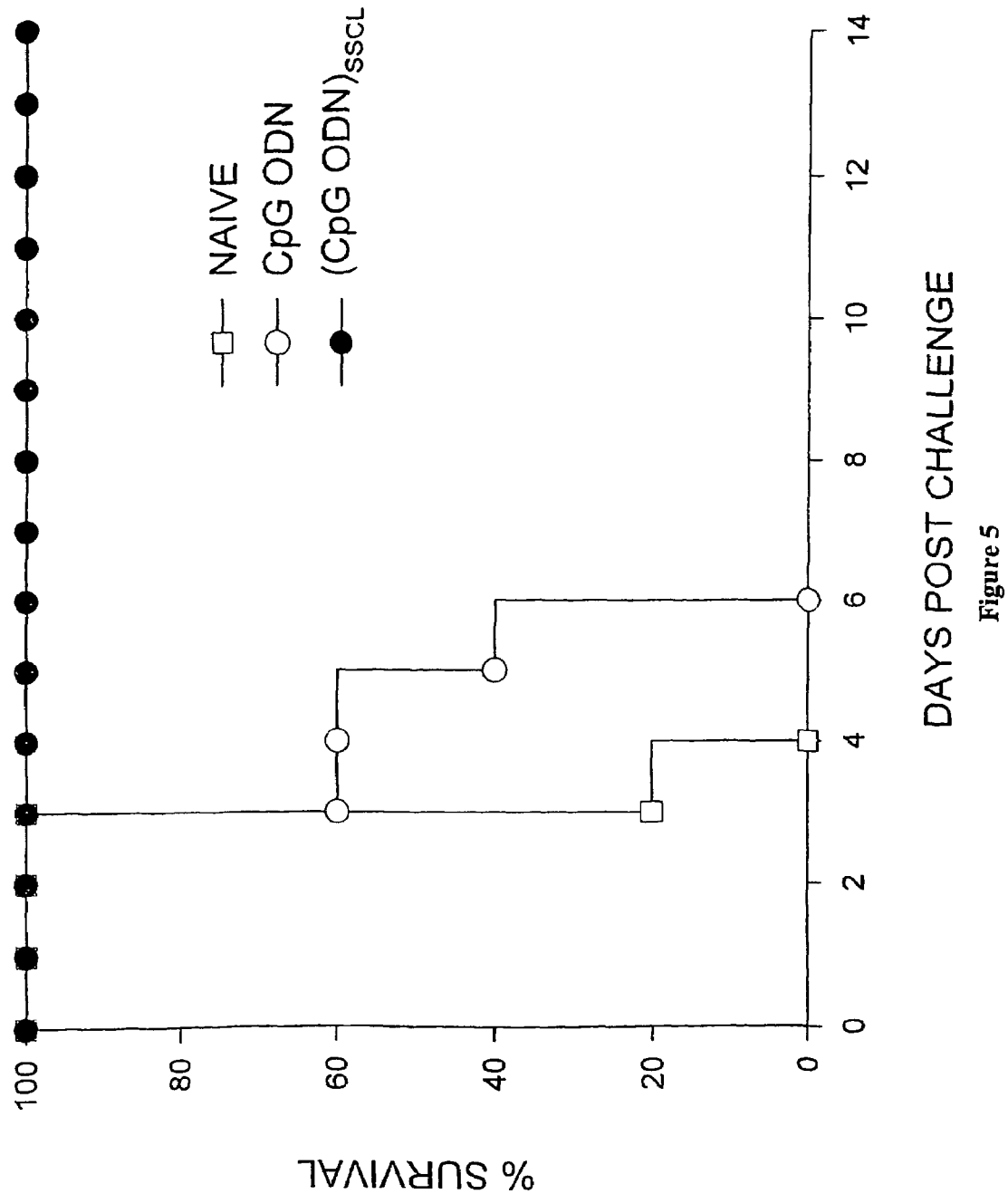
FIG. 5 is a graph demonstrating (CpG ODN)$_{SSCL}$ provide protection against lethal pathogen challenge. BALB/c mice were injected IP with 50 ug of free or (CpG ODN)$_{SSCL}$. Four weeks later, animals were challenged with $10^3$ LD$_{50}$ of L. monocytogenes and survival followed. Results represent the total experience from 2 experiments involving 10 mice/group/experiment.

BALB/c mice were injected IP with 50 μg of CpG ODN or (CpG ODN)$_{SSCL}$. Two weeks after treatment, all animals survived infection by $10^3$ LD$_{50}$ of *L. monocytogenes* (data not shown). However, when challenge was delayed until 30 days, only those animals treated with encapsulated ODN survived (p<0.0001) (FIG. 5)

Example 8

D ODN are not Effectively Delivered by SSCL

Endotoxin free ODN were synthesized by the CBER core facility. Multiple D ODN were studied with similar results. Exemplary D ODN include D35, the most commonly used ODN, had the sequence 5'-GGtgcatcgatgcagggGG (phosphodiester bases are in lower case while phosphorothioate bases are in upper case; SEQ ID NO: 61). Additional ODN studied were D19; GgtgcatcgatgcagGGGGG (SEQ ID NO: 61), D29; GgtgcaccggtgcagGGGGG (SEQ ID NO: 65) and control ODN; GgtgcatctatgcaggggGG (SEQ ID NO: 176). All antibodies were purchased from Pharmingen (San Jose, Calif.).

Normal PBMC and elutriated monocytes (>95% pure) were prepared. Approximately 4×10$^6$ cells/ml were cultured for 24-96 hours with 0.3 to 3 μM of ODN. Equivalent levels of monocyte maturation were obtained by culture in either serum-free X-VIVO 15 medium (BioWittaker, Walkersville, Md., USA) or RPMI 1640 supplemented with 5% FCS, 50 U/ml penicillin, 50 μg/ml streptomycin, 0.3 mg/ml L-glutamine, 0.1 mM non-essential amino acids, 1 mM sodium pyruvate, 10 mM HEPES and 10$^{-5}$ M 2-mercaptoethanol.

Figure 15:
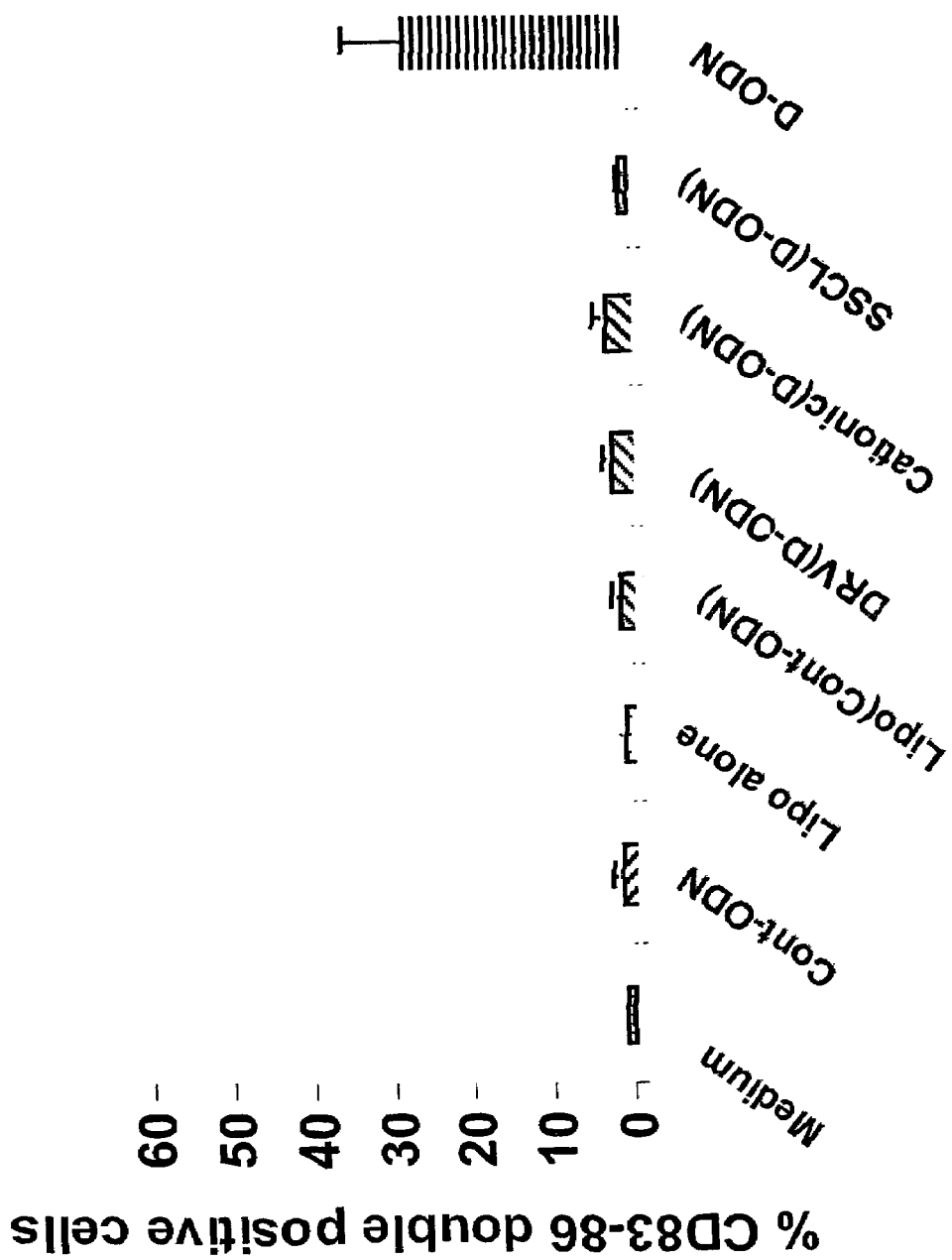
FIG. 15 is a bar graph of the maturation of dendritic cells in response to ODN. D ODN encapsulated in SSCL do not induce the maturation of dendritic cells (as measured by expression of cell surface markers). Thus, cationic liposomes are not of use with D ODN, but provide unexpectedly superior results in encapsulating and delivering K ODN.

Cells cultured for various periods with D ODN were washed and stained for surface expression of CD83, CD86, CD40, CD80 and/or CD14 using phenotype-specific MAb. Samples were analyzed (40,000 events) by FACScan (Becton Dickinson, San Jose, Calif.) after gating on live cells with proper electronic compensation. Expression of both CD83 and CD86 (CD83+CDS6+) was evaluated. The results are shown in FIG. 15. As expected, unencapsulated and SSCL encapsulated K ODN had no effect on dendritic cell maturation. In addition, as expected, exposure to unencapsulated D ODN resulted in the maturation of dendritic cells. However, encapsulation of D ODN in SSCL eliminated the effect on dendritic cell maturation. Thus SSCL effectively deliver K type CpG ODN, but not D type CpG ODN.

Example 9

Materials and Methods for IL-13-PE/K ODN Studies

Mice: Athymic nude mice and Beige mice (deficient for NK cell) were obtained from Frederick Cancer Research Center Animal Facilities (National Cancer Institute, Frederick, Md.), and were housed under pathogen-free conditions. Animal care was in accordance with the guidelines of the Center for Biologics and Evaluation Research.

Cells: A human head and neck cancer cell line KCCT873 was established in the Research Institute, Kanagawa Cancer Center (Yokohama, Japan; Kawakami *Cancer Res.* 61:6194-6200, 2001). Cells were cultured in complete RPMI 1640 media containing 10% FBS, 1 mM HEPES, 1 mM L-glutamine, 100 μg/ml penicillin and 100 μg/ml streptomycin.

Oligonucleotides: Synthetic single stranded oligodeoxynucleotides with phosphorothioate linkage (ODN) were synthesized at the CBER core facility (Bethesda, Md.). Sequences of ODNs were: CpG ODN (1555), 5'-GCTA-GACGTTAGCGT-3' (SEQ ID NO: 1); Control ODN (1612), 5'-GCTAGATGTTAGCGT-3' (SEQ ID NO: 177) (Klinman et al., *Proc. Natl. Acad. Sci. USA* 93:2879-2883, 1996). All DNA stock solutions were under detectable level of endotoxin (<0.01 U/ml) as determined by Limulus amebocyte lysate (LAL) assay (Bio-Whittaker, Walkersville, Md.).

Preparation of sterically stabilized cationic liposome (SSCL): ODN encapsulated in sterically stabilized cationic liposome were generated as described above. Liposome formulations were stored at 4° C. until use.

Preparation of IL-13 toxin: The chimeric fusion gene encoding IL-13 cytotoxin (hIL13-PE38QQR, as referred to IL13-PE) was constructed by using human IL-13 cDNA cloned from human PBMCs and the plasmid PE38QQR (pRKL438QQR) as previously described (Debinski, *J. Biol. Chem.* 270:16775-16780, 1995). Endotoxin was less than 0.01 U/mg in all preparations.

Human Head and Neck Cancer Xenografts, Treatments and Evaluations: Human head and neck tumors were established in nude or beige mice by s.c. injection of 5×10$^6$ KCCT873 cells in 150 μl of PBS plus 0.2% human serum albumin into the flank as previously described (Kawakami, *Cancer Res.* 61: 6194-6200, 2001). Palpable tumors developed within 3-4 days. The mice then received injections of excipient (0.2% HSA in PBS) or different dose of IL13-PE by intratumoral injection (IT, 30 µl) using a 27-gauge needle. (CpG ODN)$_{SSCL}$ (50 µg in 20 µl) was injected in the same manner. At various time points, tumor growth was measured by Vernier calipers in a standard manner as described elsewhere (Kawakami *Cancer Res.* 61: 6194-6200, 2001). Tumor size was calculated by multiplying the length and width of the tumor on a given day. In some experiments, mice were re-challenged with the same number of KCCT873 cells. In some experiments, NK cells were depleted by pre and post treatment with rabbit anti asialo-GM1 Ab (50 µg per injection, Wako, Osaka, Japan) at day —3, 4, 10 and 16 of tumor implantation, while the control group was treated with the same amount of normal rabbit IgG (R&D systems, Minneapolis, Minn.).

Measurement of cytokine production: Single cell suspension of spleen was prepared from untreated mice as previously described (Ishii et al., *J. Immunol.* 167, 2602-2607, 2001). The cells ($2.5 \times 10^6$/ml) were cultured in the presence or absence of various reagents including ODNs, IL13-PE in complete media for 48 hours at 37° C., 5% $CO_2$. Supernatants were immediately examined to measure cytokine concentration by ELISA.

Measurement of cytotoxicity: Mice (3 mice per group) with or without tumor implantation were injected intratumorally or s.c. with IL13-PE (50 µg/kg), with or without either (CpG ODN)$_{SSCL}$ or (Control ODN)$_{SSCL}$ (50 µg/mouse). Twenty-four hours or 10 days after injection, mice were sacrificed, spleen cells were removed and a single cell suspension was prepared. Cytotoxicities of these spleen cells against tumor cells were measured by using modified $^{51}$Cr release assay as previously described (Ishii et al., *Vaccine* 18:703-710, 1999). Briefly, KCCT873 cells ($1 \times 10^6$/ml) were labeled with 1 µCi of $^{51}$Cr (NEN, Boston, Mass.) for 18 hours prior to the assay. Tumor cells were carefully harvested and incubated with spleen cells from treated mice as described above at various effector:target (ET) ratio for 24 hours. The released $^{51}$Cr in the supernatant was measured by gamma counting (Wallace Inc., Gaithersburg, Md.).

Immunohistochemistry: Frozen sections of implanted KCCT873 tumors were prepared as previously described (Kawakami et al., *J. Exp. Med.* 194:1743-1754, 2001). Samples were fixed and washed with ice cold PBS. Prior to incubating with following Abs diluted at 1/100 dilution in PBS/10% rat serum for 1 hour in the dark at 4° C.: anti-asialo-GM1 Ab, FITC labeled anti-mouse DX-5 (pan-NK, BD Pharmingen) and PE labeled anti-mouse Gr-1 or CD11b (BD Pharmingen). For the sample stained with anti asialo-GM Ab was washed with PBS and followed by FITC labeled anti-rabbit IgG at 1/1000 dilution for additional 1 hour at 4° C. Samples were washed with PBS 5 times and mounted with Prolong anti-fade kit (Molecular Probe, Eugene, Oreg.) as recommended by the manufacturer. Photographs of the samples were taken by fluorescence microscope (Olympus America, Melville, N.Y.).

Example 10

Figure 11A:
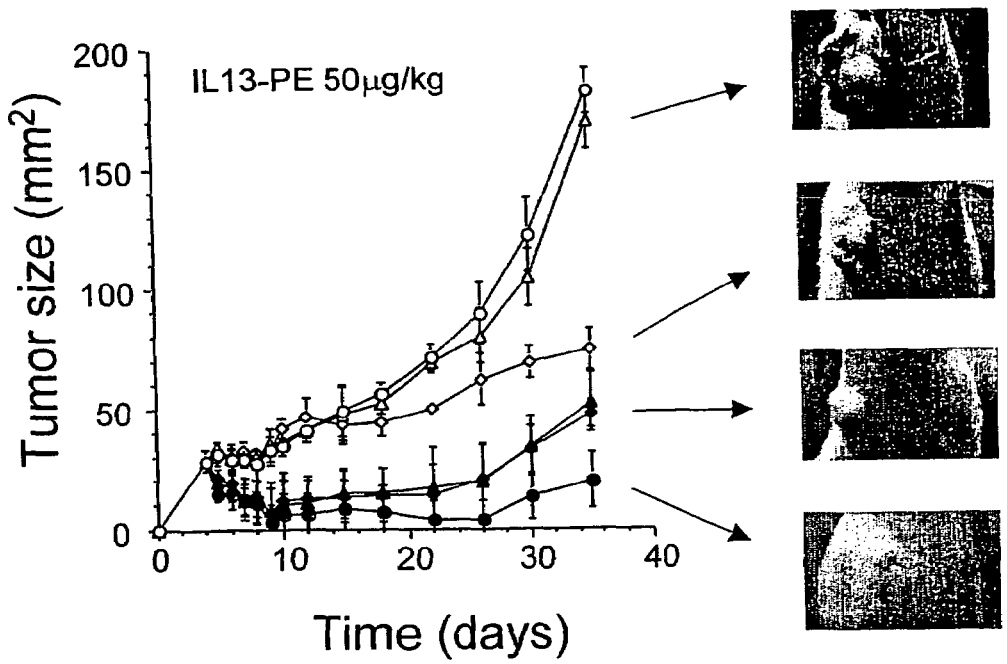
FIG. 11a shows the average and SD of tumor size (mm$^2$) and the digital image for each group is representative for that group.

Induction of Tumor Regression by the Combination of IL13-PE and (CpG ODN)$_{SSCL}$ The KCCT873 human head/neck tumor cell line was used to study the effect of various therapies on tumor growth in vivo. When KCCT873 cells were implanted in the flank of athymic nude mice, palpable tumors developed within 4 days and reached a size of >200 mm² within 4 weeks in the absence of treatment (FIG. 11a). KCCT873 cells express the IL-13 receptor alpha2, and thus are sensitive to treatment with IL13-PE (Kawakami et al., *J. Biol. Chem.* 276:25114-25120, 2001). Consistent with previous reports, intratumoral injection of 1 µg of IL13-PE to these mice (50 µg/kg) on days 4, 6, and 8 reduced the tumor growth by >75% (P<0.0005, FIG. 11a). By comparison, treating these mice with 50 µg of immunostimulatory CpG ODN encapsulated in SSCL ((CpG ODN)$_{SSCL}$) reduced tumor growth by >50% (P<0.004, FIG. 11a).

Unfortunately, neither therapy alone resulted in complete tumor regression. Since IL13-PE and (CpG ODN)$_{SSCL}$ have different modes of action (the former is directly tumoricidal, whereas the latter are immunostimulatory), the effect of combining the two treatments was examined. As seen in FIG. 11a and Table VI, the combination of (CpG ODN)$_{SCCL}$ plus low-dose IL13-PE not only reduced average tumor size by >90%, but led to a complete regression of tumors in 23% of mice (P<0.0005, Table VI). Tumor did not recur in these animals after >40 days of follow-up.

TABLE VI

IL13-PE plus (Cpg ODN)$_{SSCL}$ induce complete regression of established tumor*

| Treatments | none | IL13-PE 50 µg/kg | IL13-PE 100 µg/kg | IL13-PE 250 µg/kg |
|---|---|---|---|---|
| Control (PBS) | 1/10 (0) | 0/12 (0) | 0/6 (0) | 0/6 (0) |
| +CpG ODN 50 µg in SSCL | 0/12 | 3/13 (23) | 2/6 (33) | 5/6 (83) |

*Human head/neck cancer derived tumor was established in athymic mice and treated with IL13-PE, (CpG ODN)$_{SSCL}$, or both as described. Number of mice with complete regression/total number of mice treated (% of complete regression) is shown.

Figures 11B, 11C:
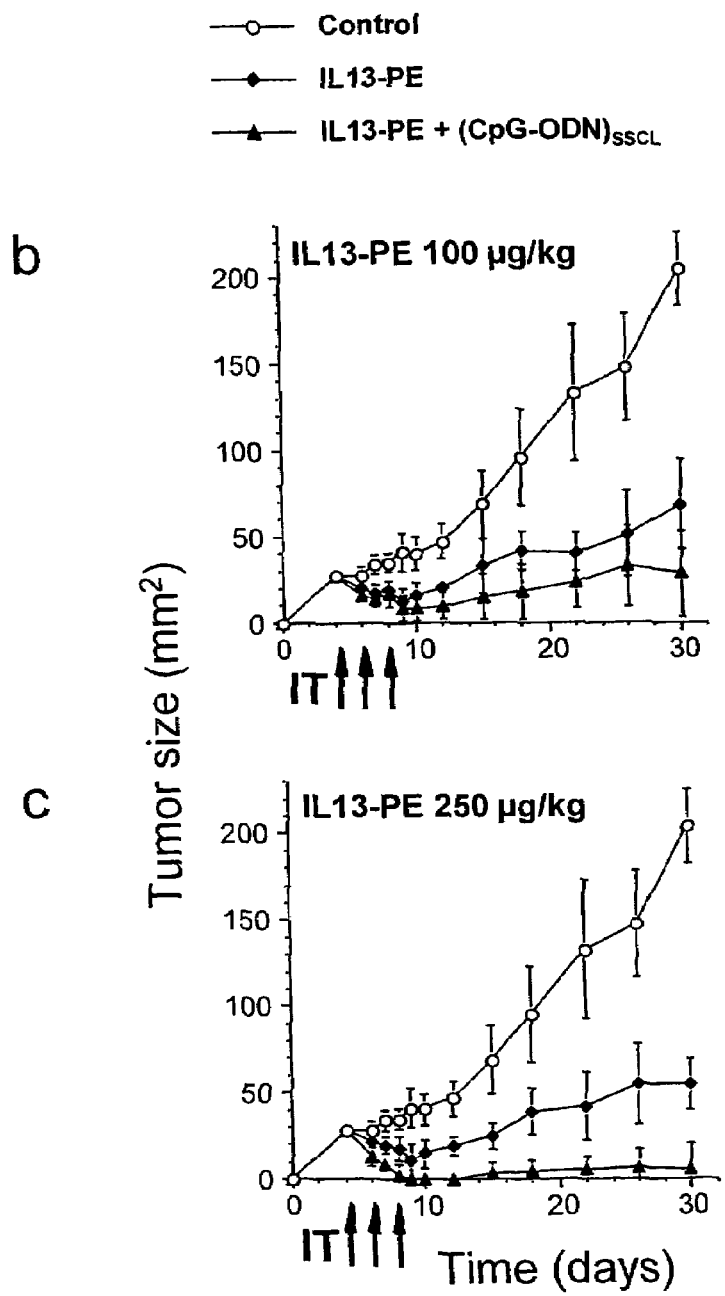
FIGS. 11b and 11c are graphs showing the dose dependent synergistic effect of IL13-PE (100, 250 μg/kg) with (CpG ODN)$_{SSCL}$ (50 μg).

The effect of increasing the dose of IL13-PE was then examined. Raising the dose of IL13-PE alone was insufficient to induce complete tumor regression. However, when 250 µg/kg of IL13-PE was combined with 50 µg of (CpG ODN)$_{SCCL}$, average tumor growth was significantly reduced, and complete remission was induced in 83% of animals (Table 1 and FIG. 11c). It is of note that the anti-tumor effect of IL13-PE alone was not as dose dependent as the combination treatment with (CpG ODN)$_{SSCL}$, indicating that IL13-PE potentiates the anti-tumor activity with (CpG ODN)$_{SSCL}$.

Although these tumor free mice did not have any recurrence for as long as observed (40 days), they accepted re-challenge of same tumor neither with regression nor with delayed growth suggesting that this anti-tumor effect of IL13-PE and (CpG ODN)$_{SSCL}$ was solely due to enhanced innate immunity.

Example 11

Histologic Analysis of Tumors Treated With (CpG ODN)$_{SSCL}$ Plus IL13-PE

To identify the cell types associated with tumor regression, KCCT873 tumors were treated on day 4 and removed for histologic analysis 5 and 10 days later. There were considerably more CD11b granulocytes and macrophages infiltrating tumors that were injected with IL13-PE plus (CpG ODN)$_{SSCL}$ than those treated with IL13-PE alone. NK cells (expressing asialo-GM1) were also present in tumors treated with combined therapy on day 5, and the number of such cells increased dramatically by day 10. In contrast, NK cells were rarely detected in untreated tumors, or tumors injected with IL13-PE alone.

These data suggest that therapy with IL13-PE plus (CpG ODN)$_{SSCL}$ induces accumulation of macrophages and granulocytes in the peripheral region of tumor at early phase followed by infiltration of NK cells into the tumor at late phase (day 10) followed by large (day 1-5). IL13-PE alone induces only accumulation of macrophage and granulocytes comparable to that of control (PBS).

Example 13

Figure 12A:
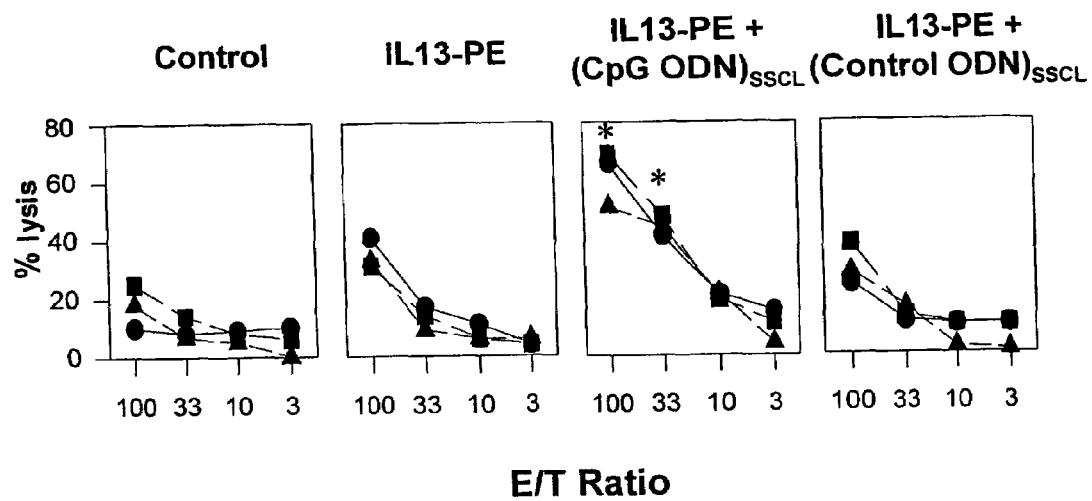
FIG. 12A is a graph of the percent lysis. Spleen cells of nude mice implanted with the KCCT873 tumor were isolated 10 days after the third injection of IL13-PE plus (CpG ODN)$_{SSCL}$. The ability of these cells to lyse tumor cells was evaluated independently in 3 mice/group (*P<0.01).

Anti-Tumor Activity of NK Cells in Mice Treated With IL13-PE Plus (CpG ODN)$_{SSCL}$ The above findings suggested that immune cells from mice treated with IL13-PE plus (CpG ODN)$_{SSCL}$ facilitated the elimination of tumor cells in vivo. To determine whether cell mediated tumor lysis was involved, spleen cells were isolated 10 days after the last treatment and incubated with $^{51}$Cr-labeled KCCT873 cells. Cells from untreated mice with the tumor mediated only low-level cytotoxicity (<20%, FIG. 12a). The spleen cells form mice treated with IL13-PE plus (CpG ODN)$_{SSCL}$ boosted tumor-specific cytotoxicity to >60% (P<0.001, FIG. 12a), which was significantly higher compared to that of the control group, IL13-PE alone, or IL13-PE plus (control ODN)$_{SSCL}$ (P<0.01). The data strongly suggest that the (CpG ODN)$_{SSCL}$ increased systemic NK activity in vivo that are able to kill implanted tumor.

Figure 12B:
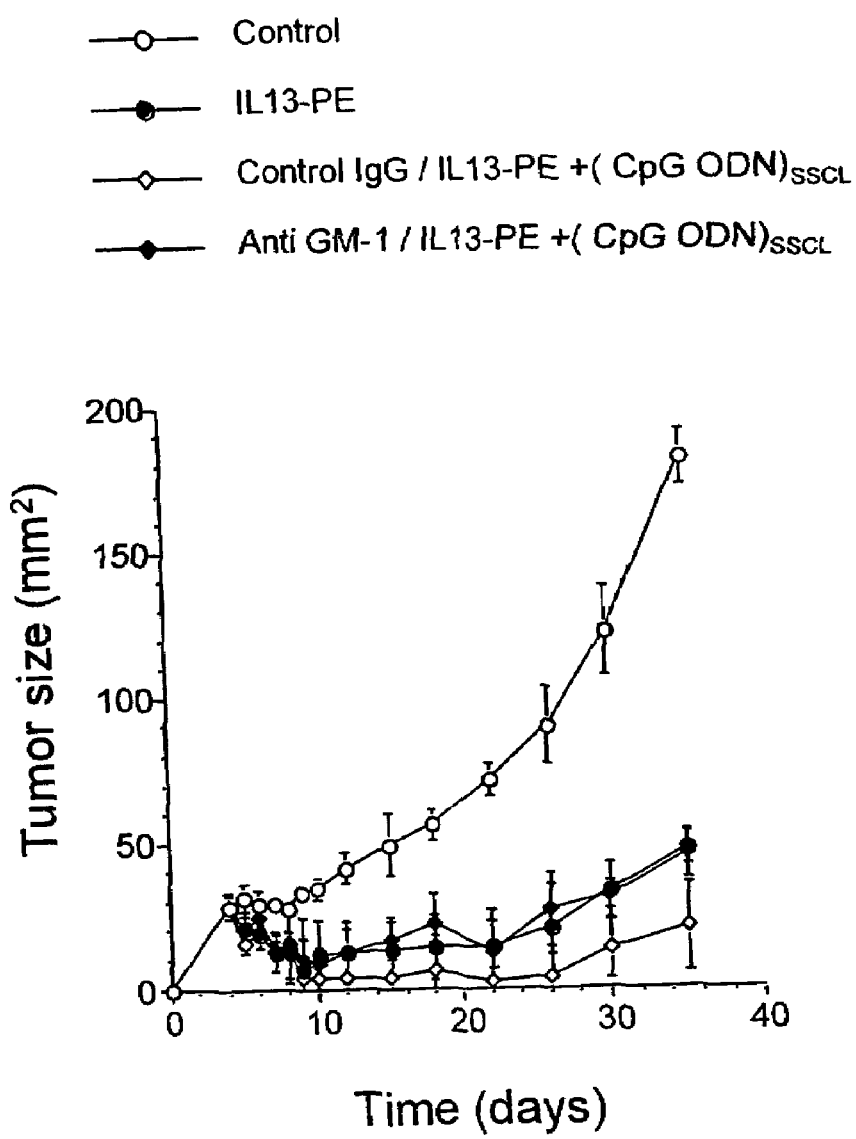
FIG. 12B is a graph of the effect of IL13-PE with or without (CpG ODN)$_{SSCL}$ on KCCT873 tumor growth in nude mice whose NK cells were depleted by repeated administration of anti asialo-GM1 Ab.

To confirm the contribution of the increased NK activity to the anti-tumor effect by (CpG ODN)$_{SSCL}$ plus IL13-PE, NK cells were depleted in vivo during the treatment. To deplete NK cells, the mice were treated IP with 50 µL of anti asialo-GM1 Ab at day —3, day 4, day 10 and day 16 after tumor implantation as previously described (Habu et al., J. Immunol. 127:34-38, 1981). The control group was treated with 50 µL of normal rabbit IgG. The treatments of tumor bearing mice with anti-asialo GM1 Ab before and after the treatment with IL13-PE and (CpG ODN)$_{SSCL}$ abrogated the additive anti-tumor effect as reduced tumor size to that of the group received IL13-PE alone (FIG. 12b and data not shown). The group treated with control Ab had no change in tumor size compared to that of mice receiving IL13-PE and (CpG ODN)$_{SSCL}$ (FIG. 12b)

Figure 12C:
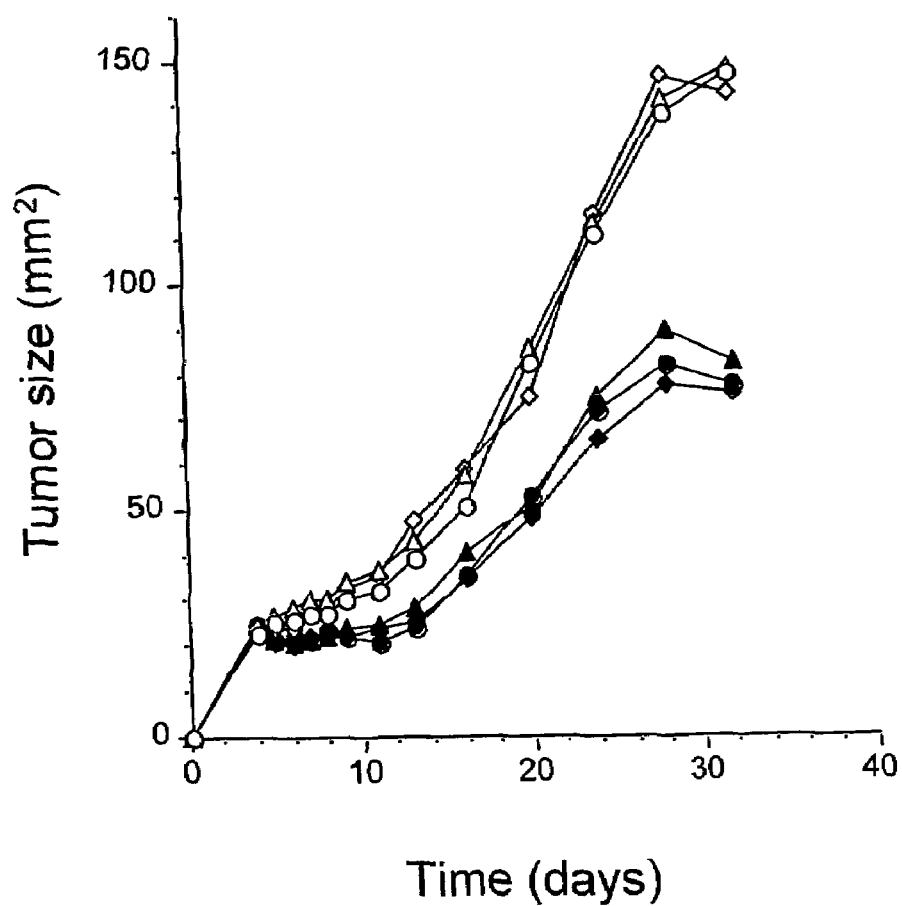
FIG. 12C is a graph of the effect of IL13-PE and (CpG ODN)$_{SCCL}$ on KCCT873 tumor in NK deficient beige mice. Results show average tumor size from 6 mice/group.

The effect of NK cells on the anti-tumor effect by (CpG ODN)$_{SSCL}$ plus IL13-PE was also tested using beige mice that lack NK cells. Beige mice allowed the tumor growth of KCCT873 similar to nude mice (FIG. 12b and c). The treatment of the tumor with IL13-PE reduced the tumor by 43%, however, (CpG ODN)$_{SSCL}$ did alter the tumor size or the number of CR by alone or with IL13-PE respectively (FIG. 12c). These data suggest that additive effect of(CpG ODN)$_{SSCL}$ on IL13-PE induced anti-tumor activity was dependent on NK activity.

Example 14

Figure 13A:
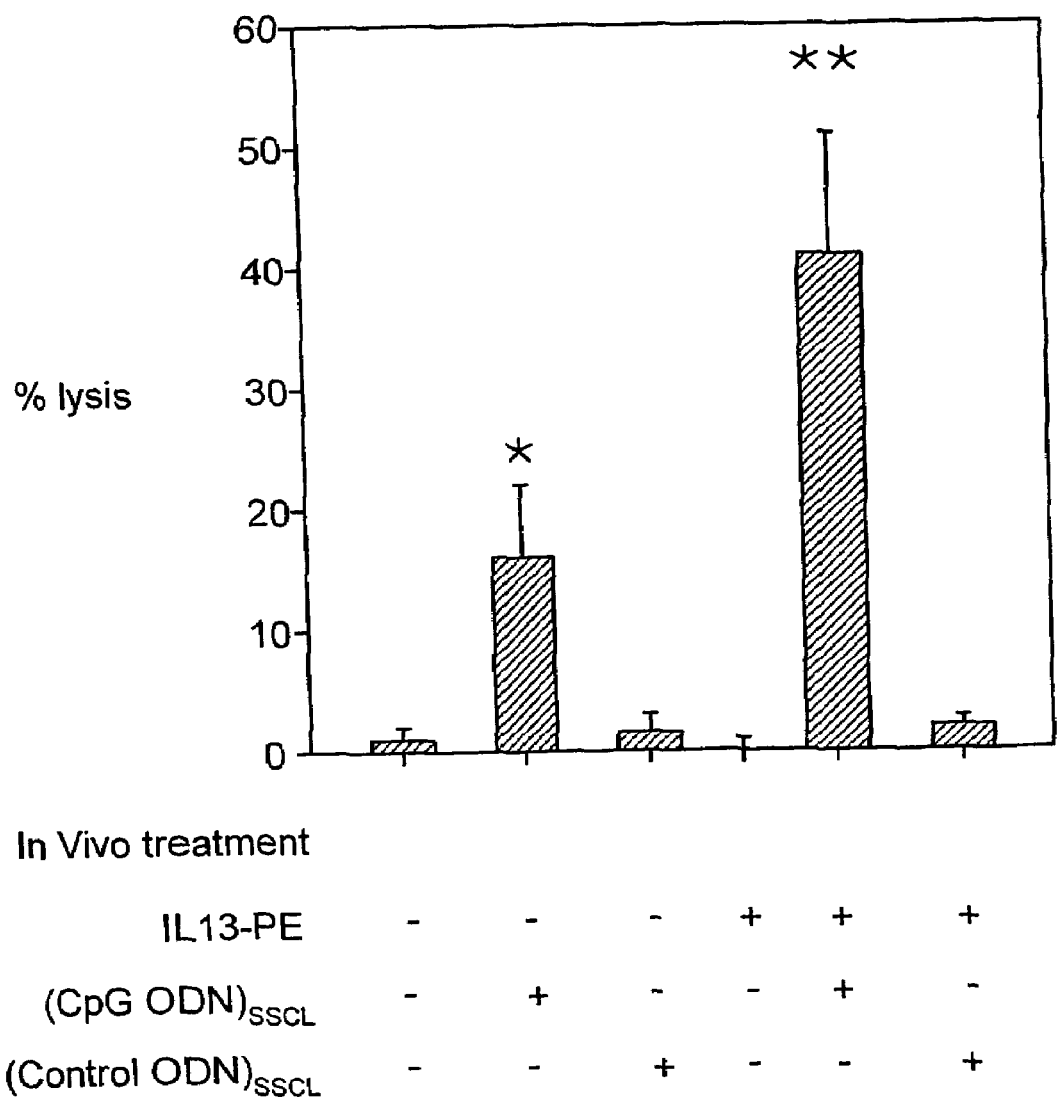
FIG. 13 is a set of graphs demonstrating that recombinant IL-13-*Pseudomonas* exotoxin (IL13-PE) synergizes (CpG ODN)$_{SSCL}$ induced cytotoxicity and cytokine productions in vivo. Nude mice were treated once with IL13-PE plus (CpG ODN)$_{SSCL}$. For FIG. 13A, one day later, spleen cells from these animals were tested for cytotoxicity against KCCT873 tumor cells. For FIG. 13B, supernatants from 3 day cultures were analyzed for cytokine production by ELISA. Data represent the mean +SD of 3 mice/group. (*P<0.05, **P<0.01 when compared to control animals).
Figure 13B:
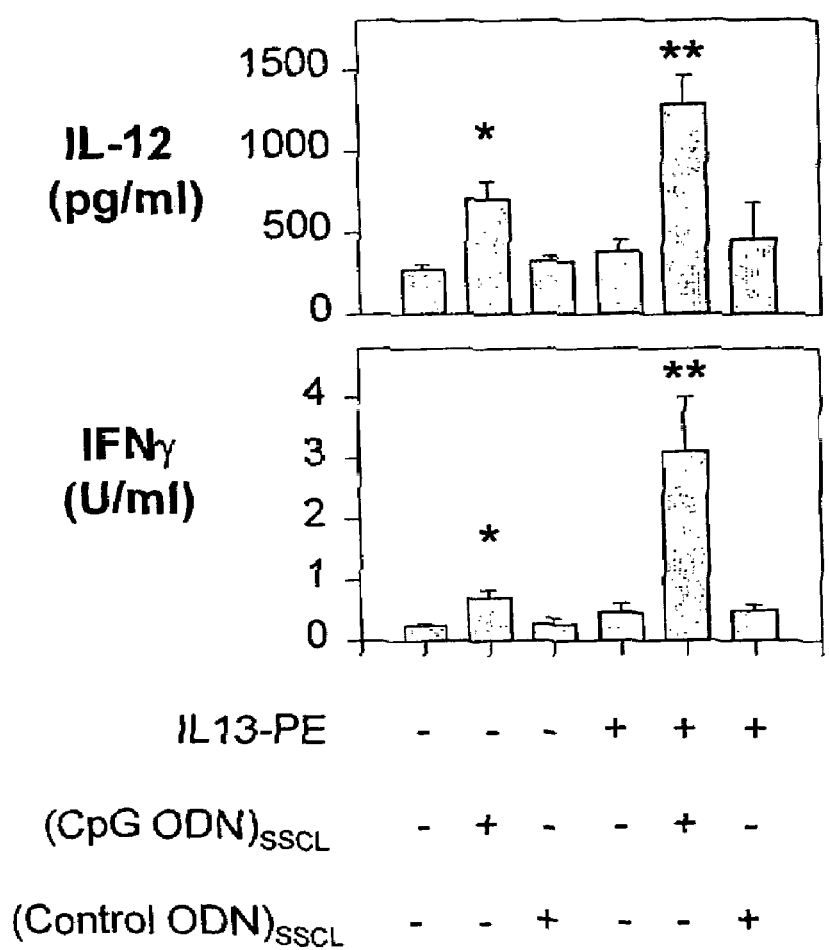

IL13-PE Synergizes Cytotoxicity and Cytokine Productions Induced by (CpG ODN)$_{SSCL}$ in vivo Studies were conducted to clarify the mechanism(s) involved in the anti-tumor effect of (CpG ODN)$_{SSCL}$ plus IL13-PE. Spleen cells were isolated from nude mice one day after treatment, and tested for cytotoxic activity against Cr$^{51}$ labeled KCCT873 cells (FIG. 13a). Of interest, cells from mice treated with (CpG ODN)$_{SSCL}$ lysed KCCT873 cells significantly more efficiently than cells from control mice, or mice treated with IL13-PE (P<0.05). Cells from animals treated with the combination of (CpG ODN)$_{SSCL}$ plus IL13-PE were even more active than those from animal injected with (CpG ODN)$_{SSCL}$ alone (P<0.01), suggesting that IL13-PE might synergistically increase the ability of (CpG ODN)$_{SSCL}$ to activate NK cells. IL-12 and IFNγ production by spleen cells from these animals was monitored ex vivo. Consistent with the increased NK activity observed above, cells from CpG ODN treated mice produced significantly more of both cytokines than those from control or IL13-PE treated animals (P<0.05). Cells from animals treated with CpG ODN plus IL13-PE were 2-3 fold higher than those from ODN treated mice (FIG. 13b, P<0.01). These results support the conclusion that IL13-PE synergizes with CpG ODN to activate cytotoxic and cytokine secreting cells in vivo. On the other hand, CpG ODN had no direct effect on viability as well as the protein synthesis of KCCT873 tumor cells in vitro confirmed by protein synthesis assay.

This work demonstrates that co-administering (CpG ODN)$_{SSCL}$ with a tumor-specific cytotoxin leads to a pronounced reduction in tumor growth. Whereas either treatment alone decreased the rate of proliferation of the KCCT873 tumor cells in vivo, when combined they were able to act synergistically to induce complete regression in most animals (Table VI and FIG. 11).

There has been considerable interest in using bacterial toxins to lyse tumor cells (Pastan, Adv. Drug Deliv. Rev. 31:53-88, 1998). By genetically modifying these "cytotoxins", their specificity has been improved and toxicity reduced (Pastan, Adv. Drug Deliv. Rev. 31:53-88, 1998). IL13-PE efficiently targets the KCCT873 tumor, which expresses IL-13 receptors. Uptake of the cytokine-toxin combination is mediated via endocytosis. The resultant inhibition of protein synthesis leads to tumor cell death by both necrosis and apoptosis (Kreitman, Curr. Opin. Immunol. 11:570-578, 1999). Although these events lead accumulation of macrophages and granulocytes to the tumor, it is not enough to clear all tumor cells leading to complete regression. IL13-PE did not induce the production of inflammatory cytokines or increased NK cell activity. Limiting the utility of such cytotoxins is their toxicity (especially to the liver and kidney), and the induction of neutralizing host Ab that lowers the efficacy of subsequent treatments (Kreitman, Curr. Opin. Immunol. 11:570-578, 1999).

By comparison, CpG motifs in bacterial DNA stimulate a broad, antigen non-specific immune response (Klinman, Proc. Natl. Acad. Sci. USA 93:2879-2883, 1996). CpG DNA stimulates the production of pro-inflammatory and Th1 cytokines (including IL-12, and IFNγ) and boosts NK cell activity (FIG. 13). By improving the activity of the innate immune system, CpG DNA may improve immune surveillance and facilitate the elimination of tumor cells via increased NK activity and IFNγ production.

As demonstrated herein, the combination of CpG ODN plus high dose IL13-PE induced long term and complete tumor regression in nude mice. Without being bound by theory, since these athymic animals lack functional T cells, the efficacy of combination therapy can be primarily attributed to tumor lysis plus enhanced activity of the innate immune system.

It will be apparent that the precise details of the methods or compositions described may be varied or modified without departing from the spirit of the described invention. We claim all such modifications and variations that fall within the scope and spirit of the claims below.

We claim:

1. A sterically stabilized cationic liposome composition, comprising a cationic lipid, a co-lipid, and a stabilizing agent encapsulating a K-type oligodeoxynucleotide of at least ten nucleotides in length comprising a CpG motif, wherein the K-type oligodeoxynucleotide comprising a CpG motif comprises a sequence represented by the formula 5'$N_1N_2N_3$Q-CpG-W$N_4N_5N_6$3'(SEQ ID NO: 97), wherein Q is a T, G, or A, W is A or T, and $N_1$, $N_2$, $N_3$, $N_4$, $N_5$, and $N_6$ are any nucleotide, and the lipid:co-lipid:stabilizing agent molar ratio is 4:6:0.06, wherein the lipid is dimethyaminoethane-carbamol-cholesterol, the co-lipid is dioleyl phosphatidyl ethanolamine, and the stabilizing agent is a polyethylene glycol: phosphatidyl ethanolamine.

2. The sterically stabilized cationic liposome composition of claim 1, further comprising an antigen.

3. The sterically stabilized cationic liposome composition of claim 2, wherein the antigen is selected from the group consisting of a protein, a polypeptide, or a polysaccharide.

4. The sterically stabilized composition of claim 1, wherein the sterically stabilized cationic liposome further comprises a targeting molecule.

5. A pharmaceutical composition comprising a therapeutically effective amount of the sterically stabilized liposome composition of claim 1 in a pharmaceutically acceptable carrier.

6. A method for stimulating an immune response in a subject, comprising administering the subject a therapeutically effective amount of the sterically stabilized cationic liposome composition of claim 1, thereby stimulating the immune response.

7. The method of claim 6, wherein the immune response is expression of a cytokine.

8. The method of claim 6, further comprising administering an antigen to the subject, thereby stimulating an antigen-specific immune response.

9. The method of claim 6, wherein the subject has a tumor and wherein the immune response is an immunotherapeutic response against the tumor.

10. A method of stimulating an immune cell, comprising contacting the immune cell with the sterically stabilized cationic liposome composition of claim 1, thereby stimulating the immune cell.

11. A method of stimulating an immune cell, comprising contacting the immune cell with the sterically stabilized cationic liposome composition of claim 1, thereby stimulating the immune cell.

12. The method of claim 7, wherein the cytokine is interferon gamma.

13. The method of claim 10, wherein the immune cell is in vitro.

14. The method of claim 10, wherein the immune cell is in vivo.

15. A method for inducing an immune response in a subject, comprising
contacting immune cells in vitro with a sterically stabilized cationic liposome encapsulating a K-type oligodeoxynucleotide of at least ten nucleotides in length comprising a CpG motif, wherein the K-type oligodeoxynucleotide comprising a CpG motif comprises a sequence represented by the formula 5'$N_1N_2N_3$Q-CpG-W$N_4N_5N_6$ 3'(SEQ ID NO: 97), wherein Q is a T, G, or A, W is A or T, and $N_1$, $N_2$, $N_3$, $N_4$, $N_5$, and $N_6$ are any nucleotide, and the lipid:co-lipid:stabilizing agent molar ratio is 4:6:0.06, wherein the lipid is dimethyaminoethane-carbamol-cholesterol, the co-lipid is dioleyl phosphatidyl ethanolamine, and the stabilizing agent is a polyethylene glycol: phosphatidyl ethanolamine;
contacting the immune cells with an antigen for a time sufficient to generate antigen specific immune cells; and
administering said antigen specific immune cells to the subject in an amount sufficient to induce an immune response.

16. The method of claim 15, further comprising administering an antigen to the subject.

17. A method of inducing an immune response against an infectious agent, comprising administering the oligonucleotide of claim 1 to a subject infected with the infectious agent, thereby inducing an immune response against the infectious agent.

18. The method of claim 16, wherein the infectious agent is a virus.

19. The method of claim 16, wherein the infectious agent is a fungus, bacteria, or a virus.

20. The method of claim 16, further comprising administering an anti-infectious agent.

21. The method of claim 20, wherein the anti-infectious agent is an antibiotic, an antiviral, or an anti-fungal agent.

22. A method for producing the sterically stabilized cationic liposome of claim 1 encapsulating an agent of interest, comprising
contacting a unilamellar vesicle with an agent of interest;
dehydrating the unilamellar vesicle and the agent of interest;
rehydrating the unilamellar vesicle and the agent of interest;
thereby producing the sterically stabilized cationic liposome encapsulating the agent of interest.

23. The sterically stabilized liposome composition of claim 1, wherein the polyethylene glycol-phosphatidyl ethanolamine has a molecular weight of 2,000 Da.

24. The sterically stabilized cationic liposome composition of claim 23, wherein the oligodeoxynucleotide comprises the nucleic acid sequence set forth in SEQ ID NO: 1.

25. The sterically stabilized cationic liposome composition of claim 23, wherein the oligodeoxynucleotide consisting of the nucleic acid sequence set forth as SEQ ID NO: 1.

* * * * *

UNITED STATES PATENT AND TRADEMARK OFFICE
CERTIFICATE OF CORRECTION

PATENT NO. : 7,666,674 B2
APPLICATION NO. : 10/484991
DATED : February 23, 2010
INVENTOR(S) : Klinman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1410 days.

Signed and Sealed this

Seventh Day of December, 2010

David J. Kappos
*Director of the United States Patent and Trademark Office*

SEQUENCE LISTING

<160> NUMBER OF SEQ ID NOS: 177

<210> SEQ ID NO 1
<211> LENGTH: 15
<212> TYPE: DNA
<213> ORGANISM: Artificial Sequence
<220> FEATURE:
<223> OTHER INFORMATION: CpG oligodeoxynucleotide

<400> SEQUENCE: 1
gctagacgtt agcgt                                                    15

<210> SEQ ID NO 2
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 2
tcaacgttga                                                          10

<210> SEQ ID NO 3
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 3
agcgtttctc gatcgacctc                                               20

<210> SEQ ID NO 4
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 4
atcgactagc gttcgttctc                                               20

<210> SEQ ID NO 5
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 5
atcgactctc gagcgttctc                                               20

<210> SEQ ID NO 6
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 6
atgcactctc gagcgttctc                                               20

<210> SEQ ID NO 7
<211> LENGTH: 20

```
<212> TYPE: DNA
<213> ORGANISM: Artificial Sequence
<220> FEATURE:
<223> OTHER INFORMATION: CpG oligodeoxynucleotide

<400> SEQUENCE: 7
atcgactctg cagcgttctc                                            20

<210> SEQ ID NO 8
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 8
atcgactctc gaggcttctc                                            20

<210> SEQ ID NO 9
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 9
atgcactctg cagcgttctc                                            20

<210> SEQ ID NO 10
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 10
atcgactctg caggcttctc                                            20

<210> SEQ ID NO 11
<211> LENGTH: 19
<212> TYPE: DNA
<213> ORGANISM: Artificial Sequence
<220> FEATURE:
<223> OTHER INFORMATION: CpG oligodeoxynucleotide

<400> SEQUENCE: 11
tcgactctcg agcgttctc                                             19

<210> SEQ ID NO 12
<211> LENGTH: 18
<212> TYPE: DNA
<213> ORGANISM: Artificial Sequence
<220> FEATURE:
<223> OTHER INFORMATION: CpG oligodeoxynucleotide

<400> SEQUENCE: 12
cgactctcga gcgttctc                                              18

<210> SEQ ID NO 13
<211> LENGTH: 17
<212> TYPE: DNA
<213> ORGANISM: Artificial Sequence
<220> FEATURE:
<223> OTHER INFORMATION: CpG oligodeoxynucleotide

<400> SEQUENCE: 13
```

```
gactctcgag cgttctc                                              17
```

<210> SEQ ID NO 14
<211> LENGTH: 16
<212> TYPE: DNA
<213> ORGANISM: Artificial Sequence
<220> FEATURE:
<223> OTHER INFORMATION: CpG oligodeoxynucleotide

<400> SEQUENCE: 14

```
actctcgagc gttctc                                               16
```

<210> SEQ ID NO 15
<211> LENGTH: 15
<212> TYPE: DNA
<213> ORGANISM: Artificial Sequence
<220> FEATURE:
<223> OTHER INFORMATION: CpG oligodeoxynucleotide

<400> SEQUENCE: 15

```
ctctcgagcg ttctc                                                15
```

<210> SEQ ID NO 16
<211> LENGTH: 14
<212> TYPE: DNA
<213> ORGANISM: Artificial Sequence
<220> FEATURE:
<223> OTHER INFORMATION: CpG oligodeoxynucleotide

<400> SEQUENCE: 16

```
tctcgagcgt tctc                                                 14
```

<210> SEQ ID NO 17
<211> LENGTH: 13
<212> TYPE: DNA
<213> ORGANISM: Artificial Sequence
<220> FEATURE:
<223> OTHER INFORMATION: CpG oligodeoxynucleotide

<400> SEQUENCE: 17

```
ctcgagcgtt ctc                                                  13
```

<210> SEQ ID NO 18
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 18

```
tcgagcgttc tc                                                   12
```

<210> SEQ ID NO 19
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 19

```
tcgaggcttc tc                                                   12
```

<210> SEQ ID NO 20
<211> LENGTH: 12
<212> TYPE: DNA
<213> ORGANISM: Artificial Sequence

```
<220> FEATURE:
<223> OTHER INFORMATION: CpG oligodeoxynucleotide

<400> SEQUENCE: 20
gtcgacgttg ac                                                          12

<210> SEQ ID NO 21
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 21
gtcggcgttg ac                                                          12

<210> SEQ ID NO 22
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 22
gtcggcgtcg ac                                                          12

<210> SEQ ID NO 23
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 23
gtcggcgctg ac                                                          12

<210> SEQ ID NO 24
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 24
gtcaacgccg ac                                                          12

<210> SEQ ID NO 25
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 25
gtcagcgccg ac                                                          12

<210> SEQ ID NO 26
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 26
gtcgacgccg ac                                                          12
```

```
<210> SEQ ID NO 27
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 27
gtcggcgccg ac                                                              12

<210> SEQ ID NO 28
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 28
gtcgacgctg ac                                                              12

<210> SEQ ID NO 29
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 29
gtcgacgtcg ac                                                              12

<210> SEQ ID NO 30
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 30
tcagcgttga                                                                 10

<210> SEQ ID NO 31
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 31
tcgacgttga                                                                 10

<210> SEQ ID NO 32
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 32
tcaacgtcga                                                                 10

<210> SEQ ID NO 33
<211> LENGTH: 10
<212> TYPE: DNA
<213> ORGANISM: Artificial Sequence
<220> FEATURE:
<223> OTHER INFORMATION: CpG oligodeoxynucleotide
```

```
<400> SEQUENCE: 33
tcaacgctga                                                           10

<210> SEQ ID NO 34
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 34
tcagcgtcga                                                           10

<210> SEQ ID NO 35
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 35
tcagcgctga                                                           10

<210> SEQ ID NO 36
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 36
tcggcgttga                                                           10

<210> SEQ ID NO 37
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 37
tcggcgtcga                                                           10

<210> SEQ ID NO 38
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 38
tcggcgctga                                                           10

<210> SEQ ID NO 39
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 39
tcaacgccga                                                           10

<210> SEQ ID NO 40
```

```
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 40
tcagcgccga                                                                 10

<210> SEQ ID NO 41
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 41
tcgacgccga                                                                 10

<210> SEQ ID NO 42
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 42
tcggcgccga                                                                 10

<210> SEQ ID NO 43
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 43
tcgacgctga                                                                 10

<210> SEQ ID NO 44
<211> LENGTH: 10
<212> TYPE: DNA
<213> ORGANISM: Artificial Sequence
<220> FEATURE:
<223> OTHER INFORMATION: CpG oligodeoxynucleotide

<400> SEQUENCE: 44
tcgacgtcga                                                                 10

<210> SEQ ID NO 45
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 45
gtggcgttcg ac                                                              12

<210> SEQ ID NO 46
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 46
```
gtcgggcgtt ac                                          12

<210> SEQ ID NO 47
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 47
gtcgggcttg ac                                          12

<210> SEQ ID NO 48
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 48
gtcggtgttg ac                                          12

<210> SEQ ID NO 49
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 49
gtcggcgttg ac                                          12

<210> SEQ ID NO 50
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 50
gggggcgttg gg                                          12

<210> SEQ ID NO 51
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 51
tttggcgttt tt                                          12

<210> SEQ ID NO 52
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 52
aaaggcgtta aa                                          12

<210> SEQ ID NO 53
<211> LENGTH: 12
<212> TYPE: DNA

```
<213> ORGANISM: Artificial Sequence
<220> FEATURE:
<223> OTHER INFORMATION: CpG oligodeoxynucleotide

<400> SEQUENCE: 53
cccggcgttc cc                                                           12

<210> SEQ ID NO 54
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 54
gtcatcgatg ca                                                           12

<210> SEQ ID NO 55
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 55
gtcgtcgatg ac                                                           12

<210> SEQ ID NO 56
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 56
gggaacgttg gg                                                           12

<210> SEQ ID NO 57
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 57
tttaacgttt tt                                                           12

<210> SEQ ID NO 58
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 58
aaaaacgtta aa                                                           12

<210> SEQ ID NO 59
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 59
cccaacgttc cc                                                           12
```

```
<210> SEQ ID NO 60
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 60
ggggtcaacg ttgagggggg                                          20

<210> SEQ ID NO 61
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 61
ggtgcatcga tgcagggggg                                          20

<210> SEQ ID NO 62
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 62
ggtgcatcga tgcagggggg                                          20

<210> SEQ ID NO 63
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 63
ggtgcaccga tgcagggggg                                          20

<210> SEQ ID NO 64
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 64
ggtgcgtcga tgcagggggg                                          20

<210> SEQ ID NO 65
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 65
ggtgcaccgg tgcagggggg                                          20

<210> SEQ ID NO 66
<211> LENGTH: 20
<212> TYPE: DNA
<213> ORGANISM: Artificial Sequence
<220> FEATURE:
```

<223> OTHER INFORMATION: CpG oligodeoxynucleotide

<400> SEQUENCE: 66
ggtgcatcga cgcagggggg                                          20

<210> SEQ ID NO 67
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 67
ggtgcgtcga cgcagggggg                                          20

<210> SEQ ID NO 68
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 68
ggtgcatcga tgcagggggg                                          20

<210> SEQ ID NO 69
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 69
aaggtcaacg ttgaaaaaaa                                          20

<210> SEQ ID NO 70
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 70
ggtgcgtcgg tgcagggggg                                          20

<210> SEQ ID NO 71
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 71
ggtgcgtcga tgcagggggg                                          20

<210> SEQ ID NO 72
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 72
ggtgcatcgg tgcagggggg                                          20

```
<210> SEQ ID NO 73
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 73
ggtgcatcgg tgcagggggg                                               20

<210> SEQ ID NO 74
<211> LENGTH: 18
<212> TYPE: DNA
<213> ORGANISM: Artificial Sequence
<220> FEATURE:
<223> OTHER INFORMATION: CpG oligodeoxynucleotide

<400> SEQUENCE: 74
tcgatcgatg caggggggg                                                18

<210> SEQ ID NO 75
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 75
ggtgcatcga tgcagggggg tcgagcgttc tc                                 32

<210> SEQ ID NO 76
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 76
tcgagcgttc tcggtgcatc gatgcagggg gg                                 32

<210> SEQ ID NO 77
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 77
ggtgcatcga tgcagggggg tgcaggcttc tc                                 32

<210> SEQ ID NO 78
<211> LENGTH: 32
<212> TYPE: DNA
<213> ORGANISM: Artificial Sequence
<220> FEATURE:
<223> OTHER INFORMATION: CpG oligodeoxynucleotide

<400> SEQUENCE: 78
ggtgcatgca tgcagggggg tcgagcgttc tc                                 32

<210> SEQ ID NO 79
<211> LENGTH: 32
<212> TYPE: DNA
<213> ORGANISM: Artificial Sequence
<220> FEATURE:
<223> OTHER INFORMATION: CpG oligodeoxynucleotide
```

```
<400> SEQUENCE: 79
ggtgcatgca tgcagggggg tgcaggcttc tc                                    32

<210> SEQ ID NO 80
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 80
tgcttcgagc tc                                                          12

<210> SEQ ID NO 81
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 81
tgcagcgagc tc                                                          12

<210> SEQ ID NO 82
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 82
tgcaccgttc tc                                                          12

<210> SEQ ID NO 83
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 83
tcgccgcttc tc                                                          12

<210> SEQ ID NO 84
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 84
tgctgcgttc tc                                                          12

<210> SEQ ID NO 85
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 85
tcgatgcttc tc                                                          12

<210> SEQ ID NO 86
<211> LENGTH: 12
```

```
<212> TYPE: DNA
<213> ORGANISM: Artificial Sequence
<220> FEATURE:
<223> OTHER INFORMATION: CpG oligodeoxynucleotide

<400> SEQUENCE: 86
gcgaggcttc tc                                                              12

<210> SEQ ID NO 87
<211> LENGTH: 12
<212> TYPE: DNA
<213> ORGANISM: Artificial Sequence
<220> FEATURE:
<223> OTHER INFORMATION: CpG oligodeoxynucleotide

<400> SEQUENCE: 87
ccgaggcttc tc                                                              12

<210> SEQ ID NO 88
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 88
ggtatatcga tataggggggg                                                     20

<210> SEQ ID NO 89
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 89
ggtggatcga tccaggggggg                                                     20

<210> SEQ ID NO 90
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 90
ggtgcatgta tgcaggggggg                                                     20

<210> SEQ ID NO 91
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 91
ggtgcacgcg tgcaggggggg                                                     20

<210> SEQ ID NO 92
<211> LENGTH: 24
<212> TYPE: DNA
<213> ORGANISM: Artificial Sequence
<220> FEATURE:
<223> OTHER INFORMATION: CpG oligodeoxynucleotide

<400> SEQUENCE: 92
```

-continued

```
tcgagcgttc tctgcaggct tctc                                        24

<210> SEQ ID NO 93
<211> LENGTH: 24
<212> TYPE: DNA
<213> ORGANISM: Artificial Sequence
<220> FEATURE:
<223> OTHER INFORMATION: CpG oligodeoxynucleotide

<400> SEQUENCE: 93
tcgagcgttc tcttgagtgt tctc                                        24

<210> SEQ ID NO 94
<211> LENGTH: 20
<212> TYPE: DNA
<213> ORGANISM: Artificial Sequence
<220> FEATURE:
<223> OTHER INFORMATION: CpG oligodeoxynucleotide

<400> SEQUENCE: 94
ggtgcattaa tgcagggggg                                             20

<210> SEQ ID NO 95
<211> LENGTH: 22
<212> TYPE: DNA
<213> ORGANISM: Artificial Sequence
<220> FEATURE:
<223> OTHER INFORMATION: CpG oligodeoxynucleotide

<400> SEQUENCE: 95
ggtcgagcgt tctcgggggg gg                                          22

<210> SEQ ID NO 96
<211> LENGTH: 22
<212> TYPE: DNA
<213> ORGANISM: Artificial Sequence
<220> FEATURE:
<223> OTHER INFORMATION: CpG oligodeoxynucleotide

<400> SEQUENCE: 96
ggtcgagcgt tctcgggggg gg                                          22

<210> SEQ ID NO 97
<211> LENGTH: 10
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 97 nnndcgwnnn                                                        10

<210> SEQ ID NO 98
<211> LENGTH: 16
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
```

```
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 98
nnnrycgryn nnggggg                                                    16

<210> SEQ ID NO 99
<211> LENGTH: 17
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 99
nnnrycgryn nnngggg                                                    17

<210> SEQ ID NO 100
<211> LENGTH: 18
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 100
nnnrycgryn nnnngggg                                                   18

<210> SEQ ID NO 101
<211> LENGTH: 19
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 101
nnnrycgryn nnnnngggg                                                  19

<210> SEQ ID NO 102
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
```

<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 102
nnnrycgryn nnnnnnggggg    20

<210> SEQ ID NO 103
<211> LENGTH: 21
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 103
nnnrycgryn nnnnnnnggg g    21

<210> SEQ ID NO 104
<211> LENGTH: 22
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 104
nnnrycgryn nnnnnnnngg gg    22

<210> SEQ ID NO 105
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 105
nnnrycgryn nnnnnnnnng ggg    23

<210> SEQ ID NO 106
<211> LENGTH: 24
<212> TYPE: DNA
<213> ORGANISM: Artificial Sequence
<220> FEATURE:
<223> OTHER INFORMATION: CpG oligodeoxynucleotide

```
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 106
nnnrycgryn nnnnnnnnnn gggg                                      24

<210> SEQ ID NO 107
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 107
nnnrycgryn nnnnnnnnnn nggggg                                    25

<210> SEQ ID NO 108
<211> LENGTH: 26
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 108
nnnrycgryn nnnnnnnnnn nnggggg                                   26

<210> SEQ ID NO 109
<211> LENGTH: 17
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 109
nnnrycgryn nnggggg                                              17

<210> SEQ ID NO 110
<211> LENGTH: 18
<212> TYPE: DNA
<213> ORGANISM: Artificial Sequence
<220> FEATURE:
```

```
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 110
nnnrycgryn nnngggg                                              18

<210> SEQ ID NO 111
<211> LENGTH: 19
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 111
nnnrycgryn nnngggg                                              19

<210> SEQ ID NO 112
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 112
nnnrycgryn nnnnngggg                                            20

<210> SEQ ID NO 113
<211> LENGTH: 21
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 113
nnnrycgryn nnnnnngggg g                                         21

<210> SEQ ID NO 114
<211> LENGTH: 22
<212> TYPE: DNA
<213> ORGANISM: Artificial Sequence
```

```
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 114
nnnrycgryn nnnnnnnggg gg                                                   22

<210> SEQ ID NO 115
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 115
nnnrycgryn nnnnnnnngg ggg                                                  23

<210> SEQ ID NO 116
<211> LENGTH: 24
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 116
nnnrycgryn nnnnnnnnng gggg                                                 24

<210> SEQ ID NO 117
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 117
nnnrycgryn nnnnnnnnnn ggggg                                                25

<210> SEQ ID NO 118
<211> LENGTH: 26
<212> TYPE: DNA
```

```
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 118
nnnrycgryn nnnnnnnnnn ngggggg                                       26

<210> SEQ ID NO 119
<211> LENGTH: 28
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(23)
<223> OTHER INFORMATION: n is a, c, g, or t

<400> SEQUENCE: 119
nnnrycgryn nnnnnnnnnn nnnggggg                                      28

<210> SEQ ID NO 120
<211> LENGTH: 18
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 120
nnnrycgryn nngggggg                                                 18

<210> SEQ ID NO 121
<211> LENGTH: 19
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 121
nnnrycgryn nnngggggg                                                19

<210> SEQ ID NO 122
<211> LENGTH: 20
```

```
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 122
nnnrycgryn nnnnggggg                                              20

<210> SEQ ID NO 123
<211> LENGTH: 21
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 123
nnnrycgryn nnnnggggg g                                            21

<210> SEQ ID NO 124
<211> LENGTH: 22
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 124
nnnrycgryn nnnnnggggg gg                                          22

<210> SEQ ID NO 125
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 125
nnnrycgryn nnnnnnggg ggg                                          23

<210> SEQ ID NO 126
```

```
<211> LENGTH: 24
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 126
nnnrycgryn nnnnnnnngg gggg                                               24

<210> SEQ ID NO 127
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 127
nnnrycgryn nnnnnnnnng ggggg                                              25

<210> SEQ ID NO 128
<211> LENGTH: 26
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 128
nnnrycgryn nnnnnnnnnn gggggg                                             26

<210> SEQ ID NO 129
<211> LENGTH: 27
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 129
nnnrycgryn nnnnnnnnnn nggggggg                                           27
```

```
<210> SEQ ID NO 130
<211> LENGTH: 28
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 130
nnnrycgryn nnnnnnnnnn nnggggggg                                    28

<210> SEQ ID NO 131
<211> LENGTH: 19
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 131
nnnrycgryn nngggggggg                                              19

<210> SEQ ID NO 132
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 132
nnnrycgryn nnnggggggg                                              20

<210> SEQ ID NO 133
<211> LENGTH: 21
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 133
nnnrycgryn nnnnggggggg g                                           21
```

```
<210> SEQ ID NO 134
<211> LENGTH: 22
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 134
nnnrycgryn nnnnngggggg gg                                              22

<210> SEQ ID NO 135
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 135
nnnrycgryn nnnnnngggg ggg                                              23

<210> SEQ ID NO 136
<211> LENGTH: 24
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 136
nnnrycgryn nnnnnnnggg gggg                                             24

<210> SEQ ID NO 137
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 137
nnnrycgryn nnnnnnnngg ggggg                                            25
```

<210> SEQ ID NO 138
<211> LENGTH: 26
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 138
nnnrycgryn nnnnnnnnng gggggg                                              26

<210> SEQ ID NO 139
<211> LENGTH: 27
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 139
nnnrycgryn nnnnnnnnnn ggggggg                                             27

<210> SEQ ID NO 140
<211> LENGTH: 28
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 140
nnnrycgryn nnnnnnnnnn nggggggg                                            28

<210> SEQ ID NO 141
<211> LENGTH: 29
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 141
nnnrycgryn nnnnnnnnnn nngggggggg                    29

<210> SEQ ID NO 142
<211> LENGTH: 20
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 142
nnnrycgryn nngggggggg                               20

<210> SEQ ID NO 143
<211> LENGTH: 21
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 143
nnnrycgryn nnngggggggg g                            21

<210> SEQ ID NO 144
<211> LENGTH: 22
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 144
nnnrycgryn nnnngggggg gg                            22

<210> SEQ ID NO 145
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 145
nnnrycgryn nnnnngggg ggg                                          23

<210> SEQ ID NO 146
<211> LENGTH: 24
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 146
nnnrycgryn nnnnnngggg gggg                                         24

<210> SEQ ID NO 147
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 147
nnnrycgryn nnnnnnnggg ggggg                                        25

<210> SEQ ID NO 148
<211> LENGTH: 26
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 148
nnnrycgryn nnnnnnnngg gggggg                                       26

<210> SEQ ID NO 149
<211> LENGTH: 27
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

```
<400> SEQUENCE: 149
nnnrycgryn nnnnnnnnng gggggggg                                    27

<210> SEQ ID NO 150
<211> LENGTH: 28
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 150
nnnrycgryn nnnnnnnnnn gggggggg                                    28

<210> SEQ ID NO 151
<211> LENGTH: 29
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 151
nnnrycgryn nnnnnnnnnn ngggggggg                                   29

<210> SEQ ID NO 152
<211> LENGTH: 30
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 152
nnnrycgryn nnnnnnnnnn nngggggggg                                  30

<210> SEQ ID NO 153
<211> LENGTH: 21
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
```

<400> SEQUENCE: 153
nnnrycgryn nngggggggg g                                                    21

<210> SEQ ID NO 154
<211> LENGTH: 22
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 154
nnnrycgryn nnngggggg gg                                                    22

<210> SEQ ID NO 155
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 155
nnnrycgryn nnnngggggg ggg                                                  23

<210> SEQ ID NO 156
<211> LENGTH: 24
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 156
nnnrycgryn nnnnnggggg gggg                                                 24

<210> SEQ ID NO 157
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)

-continued

```
<223> OTHER INFORMATION: n is a, c, g, or t

<400> SEQUENCE: 157
nnnrycgryn nnnnnnggggg ggggg                                          25

<210> SEQ ID NO 158
<211> LENGTH: 26
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 158
nnnrycgryn nnnnnnnggg gggggg                                          26

<210> SEQ ID NO 159
<211> LENGTH: 27
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 159
nnnrycgryn nnnnnnnngg ggggggg                                         27

<210> SEQ ID NO 160
<211> LENGTH: 28
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 160
nnnrycgryn nnnnnnnnng ggggggg                                         28

<210> SEQ ID NO 161
<211> LENGTH: 29
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
```

```
<222> LOCATION: (10)..(20)
<223> OTHER INFORMATION: n is a, c, g, or t

<400> SEQUENCE: 161
nnnrycgryn nnnnnnnnnn gggggggggg                                      29

<210> SEQ ID NO 162
<211> LENGTH: 30
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 162
nnnrycgryn nnnnnnnnnn nggggggggg                                      30

<210> SEQ ID NO 163
<211> LENGTH: 31
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 163
nnnrycgryn nnnnnnnnnn nnggggggggg g                                   31

<210> SEQ ID NO 164
<211> LENGTH: 22
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 164
nnnrycgryn nngggggggg gg                                              22

<210> SEQ ID NO 165
<211> LENGTH: 23
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
```

```
<221> NAME/KEY: misc_feature
<222> LOCATION: (10)..(13)
<223> OTHER INFORMATION: n is a, c, g, or t

<400> SEQUENCE: 165
nnnrycgryn nnngggggg ggg                                          23

<210> SEQ ID NO 166
<211> LENGTH: 24
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 166
nnnrycgryn nnnngggggg gggg                                        24

<210> SEQ ID NO 167
<211> LENGTH: 25
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 167
nnnrycgryn nnnnnggggg ggggg                                       25

<210> SEQ ID NO 168
<211> LENGTH: 26
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 168
nnnrycgryn nnnnnngggg gggggg                                      26

<210> SEQ ID NO 169
<211> LENGTH: 27
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
```

```
<220> FEATURE:
<221> NAME/KEY: misc_feature
<222> LOCATION: (10)..(17)
<223> OTHER INFORMATION: n is a, c, g, or t

<400> SEQUENCE: 169
nnnrycgryn nnnnnnnggg ggggggg                                            27

<210> SEQ ID NO 170
<211> LENGTH: 28
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 170
nnnrycgryn nnnnnnnngg gggggggg                                           28

<210> SEQ ID NO 171
<211> LENGTH: 29
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 171
nnnrycgryn nnnnnnnnng ggggggggg                                          29

<210> SEQ ID NO 172
<211> LENGTH: 30
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 172
nnnrycgryn nnnnnnnnnn gggggggggg                                         30

<210> SEQ ID NO 173
<211> LENGTH: 31
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
```

```
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 173
nnnrycgryn nnnnnnnnnn ngggggggggg g                                   31

<210> SEQ ID NO 174
<211> LENGTH: 32
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 174
nnnrycgryn nnnnnnnnnnn nngggggggg gg                                  32

<210> SEQ ID NO 175
<211> LENGTH: 10
<212> TYPE: DNA
<213> ORGANISM: Artificial Sequence
<220> FEATURE:
<223> OTHER INFORMATION: CpG oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 175 nnntcgwnnn                                                            10

<210> SEQ ID NO 176
<211> LENGTH: 20
<212> TYPE: DNA
<213> ORGANISM: Artificial Sequence
<220> FEATURE:
<223> OTHER INFORMATION: control ODN

<400> SEQUENCE: 176
ggtgcatcta tgcagggggg                                                 20

<210> SEQ ID NO 177
<211> LENGTH: 15
<212> TYPE: DNA
<213> ORGANISM: Artificial Sequence
<220> FEATURE:
<223> OTHER INFORMATION: control ODN (1612)

<400> SEQUENCE: 177
gctagatgtt agcgt                                                      15
```